United States Patent
Belhocine et al.

(10) Patent No.: US 10,131,939 B2
(45) Date of Patent: *Nov. 20, 2018

(54) NUCLEIC ACID AMPLIFICATION

(71) Applicant: Theranos IP Company, LLC, Newark, CA (US)

(72) Inventors: Kamila Belhocine, Palo Alto, CA (US); Josephine Lee, Palo Alto, CA (US); Pranav Patel, Palo Alto, CA (US); Aaron Richardson, Palo Alto, CA (US); Scott Tabakman, Palo Alto, CA (US)

(73) Assignee: Theranos IP Company, LLC, Palo Alto, CA (US)

(*) Notice: Subject to any disclaimer, the term of this patent is extended or adjusted under 35 U.S.C. 154(b) by 281 days.

This patent is subject to a terminal disclaimer.

(21) Appl. No.: 14/850,608

(22) Filed: Sep. 10, 2015

(65) Prior Publication Data

US 2016/0068895 A1    Mar. 10, 2016

Related U.S. Application Data

(63) Continuation of application No. PCT/US2014/030034, filed on Mar. 15, 2014.

(60) Provisional application No. 61/800,606, filed on Mar. 15, 2013.

(51) Int. Cl.
| | | |
|---|---|---|
| *C12Q 1/68* | (2018.01) | |
| *C12Q 1/6844* | (2018.01) | |
| *C12P 19/34* | (2006.01) | |
| *C12Q 1/686* | (2018.01) | |
| *C07H 1/00* | (2006.01) | |

(52) U.S. Cl.
CPC ............. *C12Q 1/6844* (2013.01); *C07H 1/00* (2013.01); *C12P 19/34* (2013.01); *C12Q 1/686* (2013.01)

(58) Field of Classification Search
CPC .................................................. C12Q 1/6844
See application file for complete search history.

(56) References Cited

U.S. PATENT DOCUMENTS

| | | |
|---|---|---|
| 5,834,252 A | 11/1998 | Stemmer et al. |
| 5,874,260 A | 2/1999 | Cleuziat et al. |
| 5,928,905 A | 7/1999 | Stemmer et al. |
| 6,033,881 A | 3/2000 | Himmler et al. |
| 6,090,552 A | 7/2000 | Nazarenko et al. |
| 6,194,179 B1 | 2/2001 | Werner et al. |
| 6,235,502 B1 | 5/2001 | Weissman et al. |
| 6,620,597 B1 | 9/2003 | Chen et al. |
| 6,743,605 B1 | 6/2004 | Rabbani et al. |
| 6,764,821 B1 | 7/2004 | Rabbani et al. |
| 6,916,634 B2 | 7/2005 | Kopreski |
| 6,977,148 B2 | 12/2005 | Dean et al. |
| 7,264,930 B2 | 9/2007 | Rabbani et al. |
| 7,297,485 B2 | 11/2007 | Bornarth et al. |
| 7,468,245 B2 | 12/2008 | Rabbani et al. |
| 7,485,417 B2 | 2/2009 | Rabbani et al. |
| 7,713,691 B2 | 5/2010 | Rabbani et al. |
| 7,803,579 B2 | 9/2010 | Mitani et al. |
| 7,955,795 B2 | 6/2011 | Kumar |
| 7,993,839 B2 | 8/2011 | Nelson et al. |
| 8,133,989 B2 | 3/2012 | Rabbani et al. |
| 8,206,902 B2 | 6/2012 | Mitani et al. |
| 8,236,499 B2 | 8/2012 | Patel et al. |
| 8,288,092 B2 | 10/2012 | Rabbani et al. |
| 8,420,323 B2 | 4/2013 | Miyoshi et al. |
| 8,435,741 B2 | 5/2013 | Miyoshi et al. |
| 8,445,664 B2 | 5/2013 | Rabbani et al. |
| 8,486,633 B2 | 7/2013 | Rabbani et al. |
| 8,709,724 B2 | 4/2014 | Tabor et al. |
| 9,725,760 B2 * | 8/2017 | Belhocine ............ C12Q 1/6844 |
| 2001/0049125 A1 | 12/2001 | Stemmer et al. |
| 2003/0032016 A1 | 2/2003 | Barany et al. |
| 2004/0170968 A1 | 9/2004 | Lizardi |
| 2004/0209272 A1 | 10/2004 | Ben-Asouli et al. |
| 2005/0037393 A1 | 2/2005 | Gunderson et al. |
| 2005/0084894 A1 | 4/2005 | Brow et al. |
| 2005/0112631 A1 | 5/2005 | Piepenburg et al. |
| 2005/0202490 A1 | 9/2005 | Makarov et al. |
| 2005/0277146 A1 | 12/2005 | Shigemori et al. |
| 2006/0040300 A1 | 2/2006 | Dapprich et al. |
| 2006/0188893 A1 | 8/2006 | Kumar et al. |
| 2006/0194214 A1 | 8/2006 | Church et al. |
| 2007/0031857 A1 | 2/2007 | Makarov et al. |
| 2007/0054301 A1 | 3/2007 | Becker et al. |
| 2007/0128635 A1 | 6/2007 | Macevicz |
| 2007/0141048 A1 | 6/2007 | Oleksiewicz et al. |
| 2008/0227160 A1 | 9/2008 | Kool |
| 2008/0305535 A1 | 12/2008 | Auerbach |
| 2009/0098566 A1 | 4/2009 | Notomi et al. |
| 2009/0098612 A1 | 4/2009 | Rhee et al. |
| 2009/0143235 A1 | 6/2009 | Drmanac et al. |
| 2009/0155856 A1 | 6/2009 | Miyoshi et al. |
| 2009/0170096 A1 | 7/2009 | Miyoshi et al. |
| 2009/0233277 A1 | 9/2009 | Murakami |
| 2010/0029505 A1 | 2/2010 | Payan et al. |
| 2010/0075384 A1 | 3/2010 | Kong et al. |

(Continued)

FOREIGN PATENT DOCUMENTS

| | | |
|---|---|---|
| CA | 1340121 E | 11/1998 |
| CN | 101906488 A | 12/2010 |

(Continued)

OTHER PUBLICATIONS

Advisory Action dated Jan. 29, 2016 for U.S. Appl. No. 14/546,998.

(Continued)

*Primary Examiner* — David C Thomas

(57) ABSTRACT

Methods and compositions for the amplification of nucleic acids and generation of concatemers are disclosed. Amplification methods provided herein may be performed under isothermal conditions. Methods and compositions may include reagents such as nucleic acid polymerases and primers.

18 Claims, 16 Drawing Sheets

Specification includes a Sequence Listing.

(56) References Cited

U.S. PATENT DOCUMENTS

| | | |
|---|---|---|
| 2010/0151471 A1 | 6/2010 | Faham et al. |
| 2010/0184154 A1 | 7/2010 | Miyoshi et al. |
| 2011/0123991 A1 | 5/2011 | Hoser |
| 2012/0157326 A1 | 6/2012 | Tisi et al. |
| 2012/0315642 A1 | 12/2012 | Kankia |
| 2013/0005585 A1 | 1/2013 | Anderson et al. |
| 2013/0296535 A1 | 11/2013 | Church et al. |
| 2014/0113839 A1 | 4/2014 | Wu et al. |
| 2014/0295439 A1 | 10/2014 | Patel |
| 2014/0295440 A1 | 10/2014 | Belhocine et al. |
| 2014/0295447 A1 | 10/2014 | Hayashizaki et al. |
| 2014/0295498 A1 | 10/2014 | Turner et al. |
| 2014/0302504 A1 | 10/2014 | Belhocine et al. |
| 2014/0364764 A1 | 12/2014 | Jung et al. |
| 2015/0140567 A1 | 5/2015 | Belhocine et al. |
| 2016/0032357 A1 | 2/2016 | Barany et al. |
| 2016/0060673 A1 | 3/2016 | Belhocine et al. |
| 2016/0060674 A1 | 3/2016 | Patel |
| 2016/0076069 A1 | 3/2016 | Belhocine et al. |
| 2016/0281155 A1 | 9/2016 | Patel |
| 2018/0094306 A1 | 4/2018 | Belhocine et al. |

FOREIGN PATENT DOCUMENTS

| | | |
|---|---|---|
| EP | 0833942 B1 | 8/2000 |
| EP | 2048248 A1 | 4/2009 |
| EP | 0971039 B1 | 3/2011 |
| EP | 2692870 A1 | 2/2014 |
| GB | 2332516 A | 6/1999 |
| JP | 04131099 | 5/1992 |
| JP | 07016094 | 1/1995 |
| JP | 07067646 A2 | 3/1995 |
| WO | 1992001813 A1 | 2/1992 |
| WO | 1994003624 A1 | 2/1994 |
| WO | 1996001327 A1 | 1/1996 |
| WO | 1997004131 A1 | 2/1997 |
| WO | 2000079009 A2 | 12/2000 |
| WO | 02068683 A2 | 9/2002 |
| WO | 03072805 A2 | 9/2003 |
| WO | 2004061119 A2 | 7/2004 |
| WO | 2004070053 A2 | 8/2004 |
| WO | 2005030983 A2 | 4/2005 |
| WO | 2005059178 A1 | 6/2005 |
| WO | 2006095169 A1 | 9/2006 |
| WO | 2006119066 A2 | 11/2006 |
| WO | 2008012529 A1 | 1/2008 |
| WO | 2008032058 A2 | 3/2008 |
| WO | 2009120374 A2 | 10/2009 |
| WO | 2010117817 A2 | 10/2010 |
| WO | 2012017210 A1 | 2/2012 |
| WO | 2013003585 A2 | 1/2013 |
| WO | 2013035875 A1 | 3/2013 |
| WO | 2014025337 A1 | 2/2014 |

OTHER PUBLICATIONS

Advisory Action dated Dec. 24, 2015 for U.S. Appl. No. 14/546,998.
Notice of Allowance dated Mar. 4, 2016 for U.S. Appl. No. 14/214,848.
Horton et al. Engineering hybrid genes without the use of restriction enzymes: gene splicing byoverlap extension. Gene, Elsevier, Amsterdam, NL, vol. 77, No. 1, Apr. 15, 1989, pp. 61-68.
Sharbati-Tehrani et al. Concatameric cloning of porcine microRNA molecules after assembly PCR. Biochemical and Biophysical Research Communications, Elsevier, Amsterdam, NL, vol. 375, No. 3, Oct. 24, 2008, pp. 484-489.
Fire et al. Rolling replication of short DNA circles, Proceedings of the National Academy of Sciences, National Academy of Sciences, US, vol. 92, No. 10, May 1995.
Liu et al. Rolling Circle DNA Synthesis: Small Circular Oligonucleotides as Efficient Templates for DNA Polymerases, Journal of the American Chemical Society, American Chemical Society, US, vol. 118, No. 7, 1996.
Lizardi et al. Mutation detection and single-molecule counting using isothermal rolling-circle amplification, Nature Genetics, Nature Publishing Group, New York, US, vol. 19, No. 3, Jul. 1998.
Marciniak et al. Coupled rolling circle amplification loop-mediated amplification for rapid detection of short DNA sequences, Biotechniques, 2008, 45:275-280.
Office Action dated Nov. 25, 2016 for U.S. Appl. No. 14/214,854.
White et al. Concatemer Chain Reaction: a Taq DNA Polymerase-Mediated Mechanism for Generating Long Tandemly Repetitive DNA Sequences. Analytical Biochemistry, Academic Press Inc, New York, vol. 199, No. 2, Dec. 1, 1991, pp. 184-190.
Notice of Allowance dated Sep. 7, 2016 for U.S. Appl. No. 14/546,998.
Office Action dated Jul. 6, 2016 for U.S. Appl. No. 14/546,998.
Office Action dated Sep. 27, 2016 for U.S. Appl. No. 14/214,850.
Dean et al. Rapid Amplification of Plasmid and Phase DNA Using Phi29 DNA Polymerase and Multiply-Primed Rolling Circle Amplification.
G.J Hafner, et al. Isothermal Amplification and Multimerization of DNA by Bst DNA Polymerase. BioTechniques 30:852-867; Apr. 2001.
International Search Report and Written Opinion dated Aug. 14, 2014 for Application No. PCT/US2014/030028.
International Search Report and Written Opinion dated Aug. 14, 2014 for Application No. PCT/US2014/030036.
International Search Report and Written Opinion dated Sep. 18, 2014 for PCT/US2014/030034.
Lee et al. Versatile PCR-mediated insertion or deletion mutagenesis.
Merriam-Webster, definition of "analogous", available at http://www.merriam-webster.com/dictionary/analogous, accessed May 18, 2015.
Merriam-Webster, definition of "partner", available at http://www.merriam-webster.com/dictionary/partner, accessed May 18, 2015.
Merriam-Webster, definition of "portion", available at http://www.merriam-webster.com/dictionary/portion, accessed May 18, 2015.
Merriam-Webster, definition of "represent", available at http://www.merriam-webster.com/dictionary/represent, accessed May 18, 2015.
Notomi et al. Loop-medicated isothermal amplification of DNA, Nucleic Acids Res. Jun. 15, 2000;28(12):E63.
Office Action dated Oct. 26, 2015 for U.S. Appl. No. 14/546,998.
Office Action dated Oct. 30, 2015 for U.S. Appl. No. 14/214,848.
Office Action dated Jun. 8, 2015 for U.S. Appl. No. 14/546,998.
Ohshima K and Wells RD. Hairpin formation during DNA synthesis primer realignment in vitro in triplet repeat sequences from human hereditary disease genes. Journal of Biological Chemistry 272:16798-16806; Jul. 1997.
Patel R et al. Formation of chimeric DNA primer extension products by template switching onto an annealed downstream oligonucleotide. PNAS 93:2969-2974; Apr. 1996.
Wang et al. Rolling circle amplification-mediated hairpin RNA (RMHR) library construction in plants.
Wilton SD et al. Snapback SSCP analysis: Engineered conformation changes for the rapid typing of known mutations. Human Mutation 11:252-258; Mar. 1998.
Written Opinion and International Search Report dated Dec. 25, 2014 for PCT/US2014/056151.
Ashford. PATH using TwistDx's Amplification Tech in Minimally Instrumented HIV Test for Infants, GenomeWeb, Aug. 25, 2011.
Euler et al. Recombinase polymerase amplification assay for rapid detection of Rift Valley fever virus. J Clin Virol. Aug. 2012;54(4):308-12. Epub Jun. 9, 2012.
Office Action dated May 11, 2016 for U.S. Appl. No. 14/546,998.
Rohrman et al. A Paper and Plastic Device for Performing Recombinase Polymerase Amplification of HIV DNA. Lab Chip, Sep. 7, 2012;12(17):3082-8. Epub Jun. 26, 2012.
Notice of Allowance dated Jun. 20, 2017 for U.S. Appl. No. 14/214,850.
Office Action dated Oct. 19, 2017 for U.S. Appl. No. 14/850,697.
Prithiviraj et al. Rapid detection of microbial DNA by a novel isothermal genome exponential amplification reaction (GEAR) assay, Biochemical and Biophysical Research Communications, vol. 420, No. 4, Mar. 12, 2012, pp. 738-742.

(56) References Cited

OTHER PUBLICATIONS

Xu et al. Cross Priming Amplification: Mechanism and Optimization for Isothermal DNA Amplification, Scientific Reports, vol. 2, Feb. 2, 2012.

* cited by examiner

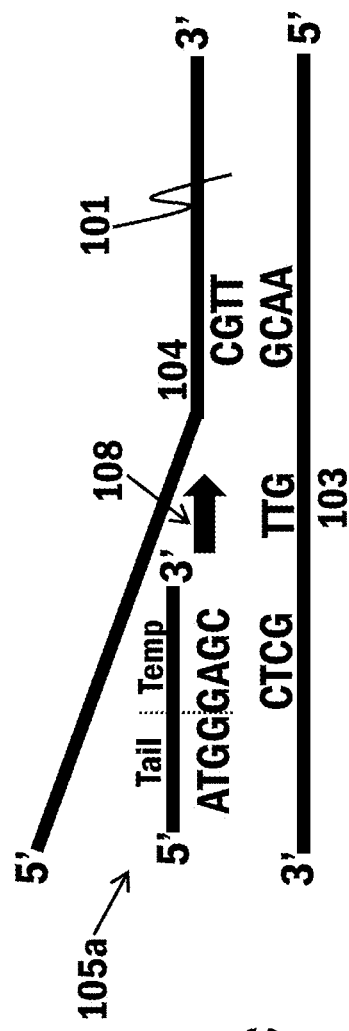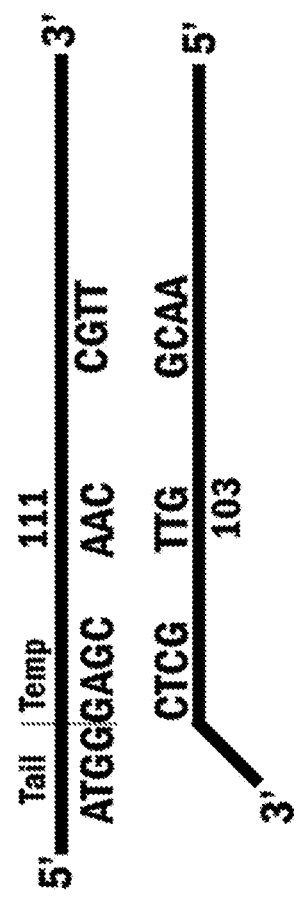
Fig. 1C
Fig. 1D

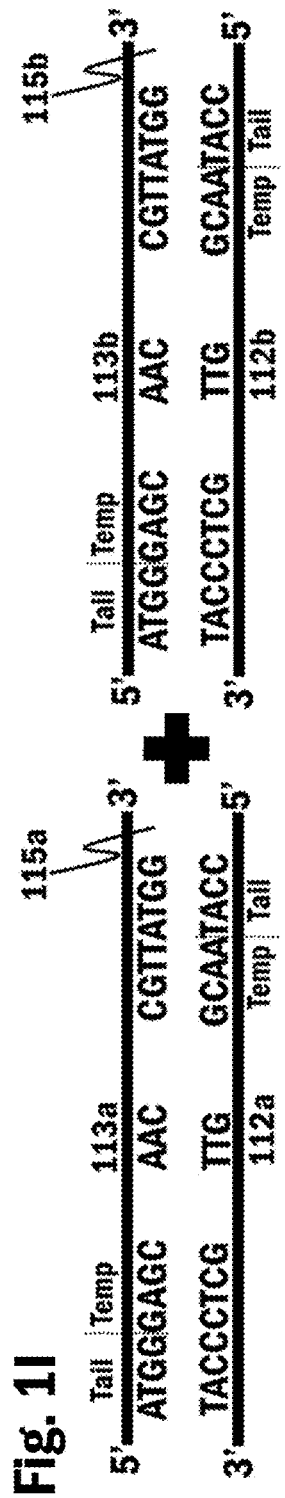
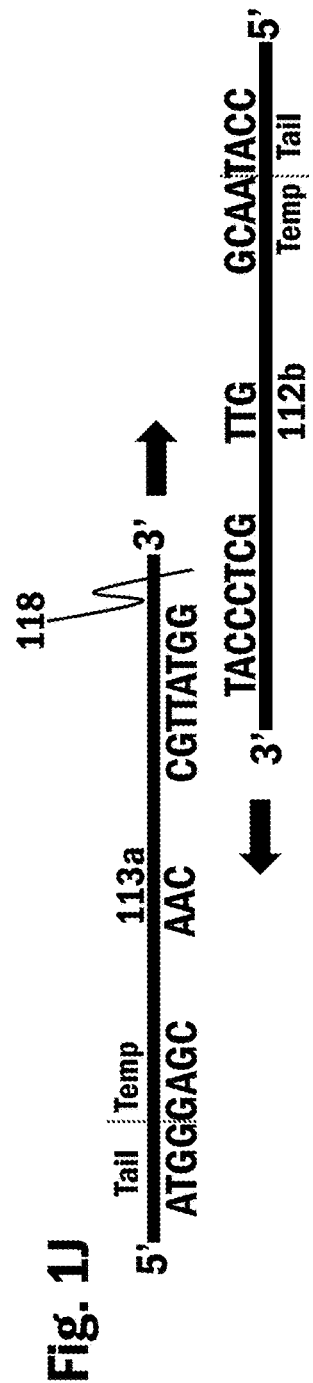

| T-Primer 1 (P1) | Length | Tail Length | T*-Primer 2 (P2) | Length | Tail Length |
|---|---|---|---|---|---|
| CGCCGGATGGCTCTTGGGAAACCAAACCGTACCAACC | 37 | 22 | GTTTCCCAAGAGCCATCGGCGATGCGGAATGTACC | 36 | 22 |
| CCGGATGGCTCTTGGGAAACCAAACCGTACCAACC | 35 | 20 | GTTTCCCAAGAGCCATCGGCGATGCGGAATGTACC | 34 | 20 |
| GGATGGCTCTTGGGAAACCAAACCGTACCAACC | 33 | 18 | GTTTCCCAAGAGCCATCCATGCGGAATGTACC | 32 | 18 |
| ATGGCTCTTGGGAAACCAAACCGTACCAACC | 31 | 16 | GTTTCCCAAGAGCCATATGCGGAATGTACC | 30 | 16 |
| TGGCTCTTGGGAAACCAAACCGTACCAACC | 30 | 15 | GTTTCCCAAGAGCCAATGCGGAATGTACC | 29 | 15 |
| GGCTCTTGGGAAACCAAACCGTACCAACC | 29 | 14 | GTTTCCCAAGAGCCATGCGGAATGTACC | 28 | 14 |
| GCTCTTGGGAAACCAAACCGTACCAACC | 28 | 13 | GTTTCCCAAGAGCATGCGGAATGTACC | 27 | 13 |
| CTCTTGGGAAACCAAACCGTACCAACC | 27 | 12 | GTTTCCCAAGAGATGCGGAATGTACC | 26 | 12 |
| TCTTGGGAAACCAAACCGTACCAACC | 26 | 11 | GTTTCCCAAGAATGCGGAATGTACC | 25 | 11 |
| CTTGGGAAACCAAACCGTACCAACC | 25 | 10 | GTTTCCCAAGATGCGGAATGTACC | 24 | 10 |
| TTGGGAAACCAAACCGTACCAACC | 24 | 9 | GTTTCCCAAATGCGGAATGTACC | 23 | 9 |
| TGGGAAACCAAACCGTACCAACC | 23 | 8 | GTTTCCCAATGCGGAATGTACC | 22 | 8 |

Fig. 2A

| | Tail | Primer (16nt) | |
|---|---|---|---|
| C5 | ATGGTCTTGGAAAC | | Forward Primer |
| D5 | GTTTCCAAGACCAT | | Reverse Primer |
| C6 | GGCTTTGGAAAC | | Forward Primer |
| D6 | GTTTCCAAGCC | | Reverse Primer |
| C7 | CTCTTGGAAAC | | Forward Primer |
| D7 | GTTTCCAAGAG | | Reverse Primer |
| C8 | TCTTGGAAAC | | Forward Primer |
| D8 | GTTTCCAAGA | | Reverse Primer |
| C9 | CTTGGAAAC | | Forward Primer |
| D9 | GTTTCCAAG | | Reverse Primer |
| C10 | TTGGAAAC | | Forward Primer |
| D10 | GTTTCCAA | | Reverse Primer |
| C11 | TGGAAAC | | Forward Primer |
| D11 | GTTTCCA | | Reverse Primer |
| C12 | GGAAAC | | Forward Primer |
| D12 | GTTTCC | | Reverse Primer |

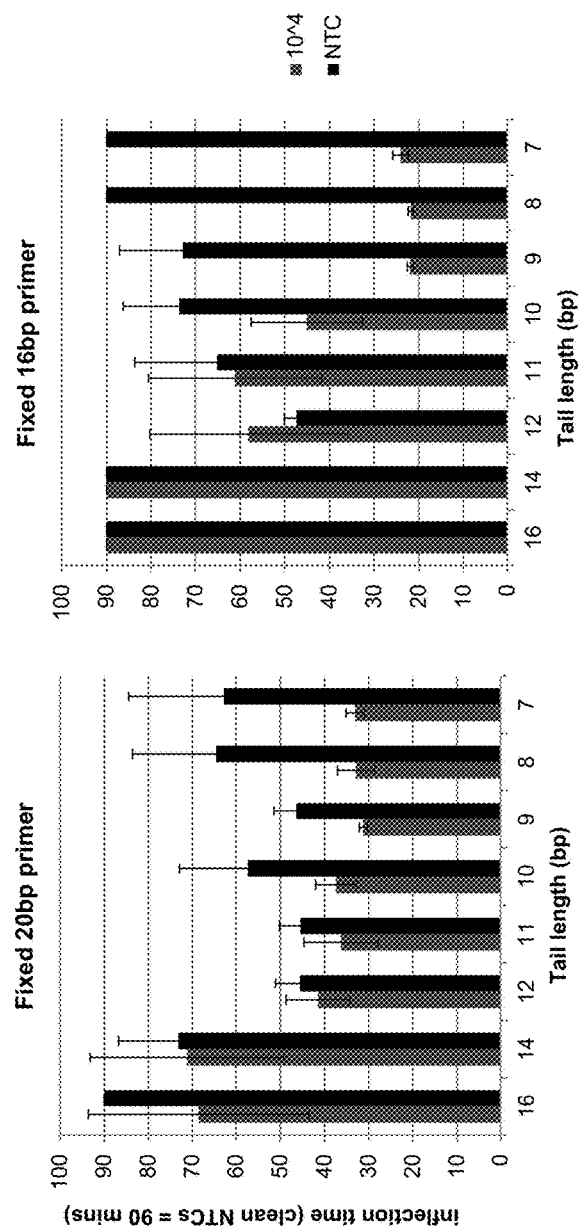

NUCLEIC ACID AMPLIFICATION

BACKGROUND

There is an increasing need for methods and reagents for the amplification of nucleic acids. Generation of multiple copies of a particular nucleic acid is often necessary or helpful in order for the nucleic acid to be used for a given application. For example, in order to analyze the nucleotide sequence of a nucleic acid of interest, frequently, the nucleic acid is replicated to increase its copy number before the sequence is analyzed. In another example, in order to determine the presence or absence of a particular nucleic acid in a sample, a sample may be treated under conditions such that if the particular nucleic acid is present in the sample, it may be amplified. In another example, a nucleic acid for use as a probe may be copied repeatedly to generate a large number of nucleic acids containing the same sequence as the original nucleic acid template, thereby generating many copies of the nucleic which may be used as a probe.

A variety of methods for the amplification of nucleic acids are known. For example, polymerase chain reaction ("PCR") (see, e.g. U.S. Pat. No. 4,683,202) is a popular method for the amplification of nucleic acids. To successfully perform a PCR reaction, the reaction must be performed at multiple different temperatures, which are repeated for multiple cycles. This requires hardware or other mechanisms for repeatedly changing the temperature of the PCR reaction. Another method for amplification of nucleic acids is referred to as loop-mediated isothermal amplification ("LAMP") (see, e.g. U.S. Pat. No. 6,410,278). LAMP reactions may be performed isothermally, but typically involve the use of four different primers which recognize a total of six distinct sequences on the target nucleic acid.

To facilitate the generation of amplified nucleic acids for the many and growing number of applications which use amplified nucleic acids, new methods and reagents for the amplification of nucleic acids are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, in the event of a conflict between the content of the present express disclosure and the content of a document incorporated by reference herein, the content of the present express disclosure controls.

SUMMARY

Provided herein are methods and compositions relating to the amplification of nucleic acids and the generation of concatemers.

In some embodiments, provided herein is a method for generating a concatemer comprising two or more copies of a double-stranded nucleic acid template, the method comprising: (A) treating a primary double-stranded nucleic acid comprising the double-stranded nucleic acid template with a first copy of a first primer and a polymerase under conditions such that an extension product of the first copy of the first primer is synthesized which is annealed to a first strand of the double-stranded nucleic acid template, wherein the first primer comprises a 5' terminal nucleotide, a 3' terminal nucleotide, and two regions: (i) a tail region comprising: (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, and the template-binding region of the first copy of the first primer anneals to the first strand of the double-stranded nucleic acid template, (B) treating the extension product of the first copy of the first primer of step (A) with a second primer and a polymerase under conditions such that an extension product of the second primer is synthesized which is annealed to the extension product of the first copy of the first primer of step (A), wherein the second primer comprises a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, the tail region of the second primer contains a nucleotide sequence which is complementary to the nucleotide sequence of the tail region of the first primer, if the sequences are aligned such that the 5' terminal nucleotide of the second primer is aligned with the innermost nucleotide of the tail region of the first primer and the 5' terminal nucleotide of the first primer is aligned with the innermost nucleotide of the tail region of the second primer, the template-binding region of the second primer anneals to the extension product of the first copy of the first primer of step (A), and the extension product of the second primer contains a 5' terminal nucleotide, a 3' terminal nucleotide, and a 3' terminal region comprising the 3' terminal nucleotide, wherein the 3' terminal region contains the same nucleotide sequence as the nucleotide sequence of the tail region of the second primer read in the 5' to 3' direction, and the final nucleotide of the 3' terminal region is the 3' terminal nucleotide of the extension product of the second primer, (C) treating the extension product of the second primer of step (B) with a second copy of the first primer and a polymerase under conditions such that an extension product of the second copy of the first primer is synthesized which is annealed to the extension product of the second primer of step (B), to produce a first copy of a secondary nucleic acid comprising the extension product of the second primer of step (B) and the extension product of the second copy of the first primer, wherein the extension product of the second copy of the first primer contains a 5' terminal nucleotide, a 3' terminal nucleotide, and a 3' terminal region comprising the 3' terminal nucleotide, wherein the 3' terminal region contains the same nucleotide sequence as the nucleotide sequence of the tail region of the first primer read in the 5' to 3' direction, and the final nucleotide of the 3' terminal region is the 3' terminal nucleotide of the extension product of the second primer, (D) repeating at least step (C) one or more addition times to generate at least a second copy of the secondary nucleic acid of step (C), (E) treating the first copy of the secondary nucleic acid of step (C) and the second copy of the secondary nucleic acid of step (D) under conditions such that the 3' terminal region of the extension product of the second copy of the first primer of the first copy of the secondary nucleic acid anneals to the 3' terminal region of the extension product of the second primer of the second copy of the secondary nucleic acid, to produce a cross-over structure comprising the extension product of the second copy of the first primer of the first copy of the secondary nucleic acid and the extension product of the second primer of the second copy of the secondary nucleic acid, (F) treating the cross-over structure of step (E) with a polymerase under conditions such that an extension product of the extension product of the second copy of the first primer of the first copy of the secondary nucleic acid is synthesized and an extension product of the extension product of the second primer of the second copy of the secondary nucleic acid is synthesized, to produce a concatemer comprising two copies of the double-stranded nucleic acid template of step (A), wherein the concatemer comprises the extension product of the extension product of the second copy of the first primer of the first copy of the secondary nucleic acid and the extension product of the extension product of the second primer of the second copy of the secondary nucleic acid.

In some embodiments, provided herein is a method for generating a concatemer comprising two or more copies of a polynucleotide template or an analogous sequence thereof, the method comprising, (A) treating a primary nucleic acid comprising the polynucleotide template with a first copy of a first primer and a polymerase under conditions such that an extension product of the first copy of the first primer is synthesized which is annealed to the polynucleotide template, wherein the first primer comprises a 5' terminal nucleotide, a 3' terminal nucleotide, and two regions: (i) a tail region comprising (a) the 5' terminal nucleotide of the primer, (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, and the template-binding region of the first copy of the first primer anneals to the polynucleotide template, (B) treating the extension product of the first copy of the first primer of step (A) with a second primer and a polymerase under conditions such that an extension product of the second primer is synthesized which is annealed to the extension product of the first copy of the first primer of step (A), wherein the second primer comprises a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, the tail region of the second primer contains a nucleotide sequence which is complementary to the nucleotide sequence of the tail region of the first primer, if the sequences are aligned such that the 5' terminal nucleotide of the second primer is aligned with the innermost nucleotide of the tail region of the first primer and the 5' terminal nucleotide of the first primer is aligned with the innermost nucleotide of the tail region of the second primer, the template-binding region of the second primer anneals to the extension product of the first copy of the first primer of step (A), and the extension product of the second primer contains a 5' terminal nucleotide, a 3' terminal nucleotide, and a 3' terminal region comprising the 3' terminal nucleotide, wherein the 3' terminal region contains the same nucleotide sequence as the nucleotide sequence of the tail region of the second primer read in the 5' to 3' direction, and the final nucleotide of the 3' terminal region is the 3' terminal nucleotide of the extension product of the second primer, (C) treating the extension product of the second primer of step (B) with a second copy of the first primer and a polymerase under conditions such that an extension product of the second copy of the first primer is synthesized which is annealed to the extension product of the second primer of step (B), to produce a first copy of a secondary nucleic acid comprising the extension product of the second primer of step (B) and the extension product of the second copy of the first primer, wherein the extension product of the second copy of the first primer contains a 5' terminal nucleotide, a 3' terminal nucleotide, and a 3' terminal region comprising the 3' terminal nucleotide, wherein the 3' terminal region contains the same nucleotide sequence as the nucleotide sequence of the tail region of the first primer read in the 5' to 3' direction, and the final nucleotide of the 3' terminal region is the 3' terminal nucleotide of the extension product of the second primer, (D) repeating at least step (C) one or more additional times to generate at least a second copy of the secondary nucleic acid comprising the extension product of the second primer of step (B) and the extension product of the second copy of the first primer of step (C), (E) treating the first copy of the secondary nucleic acid of step (C) and the second copy of the secondary nucleic acid of step (D) under conditions such that the 3' terminal region of the extension product of the second copy of the first primer of the first copy of the secondary nucleic acid anneals to the 3' terminal region of the extension product of the second primer of the second copy of the secondary nucleic acid, to produce a cross-over structure comprising the extension product of the second copy of the first primer of the first copy of the secondary nucleic acid and the extension product of the second primer of the second copy of the secondary nucleic acid, (F) treating the cross-over structure of step (E) with a polymerase under conditions such that an extension product of the extension product of the second copy of the first primer of the first copy of the secondary nucleic acid is synthesized and an extension product of the extension product of the second primer of the second copy of the secondary nucleic acid is synthesized, to produce a concatemer comprising two copies of the polynucleotide template of step (A), wherein the concatemer comprises the extension product of the extension product of the second copy of the first primer of the first copy of the secondary nucleic acid and the extension product of the extension product of the second primer of the second copy of the secondary nucleic acid. In some embodiments, the nucleic acid polymerase of step (A) is a DNA polymerase. In some embodiments, the nucleic acid polymerase of step (A) is a reverse transcriptase.

In some embodiments, provided herein is a method for generating a concatemer comprising two or more copies of a double-stranded nucleic acid template, the method comprising, (A) preparing a reaction mixture comprising: (i) a primary nucleic acid comprising the double-stranded nucleic acid template (ii) an isolated nucleic acid polymerase, (iii) a first primer comprising a 5' terminal nucleotide, a 3' terminal nucleotide, and two regions: (a) a tail region comprising (1) the 5' terminal nucleotide of the primer (2) an innermost nucleotide, wherein the innermost nucleotide is downstream from the 5' terminal nucleotide (3) a middle section between the 5' terminal nucleotide and the innermost nucleotide, comprising one or more nucleotides, and (b) a template-binding region comprising (1) the 3' terminal nucleotide of the primer (2) an innermost nucleotide, wherein the innermost nucleotide is upstream from the 3' terminal nucleotide (3) a middle section between the 3' terminal nucleotide and the innermost nucleotide, comprising one or more nucleotides, wherein the template-binding region is complementary to a first strand of the nucleic acid template, (iv) a second primer comprising a 5' terminal nucleotide, a 3' terminal nucleotide, and two regions: (a) a tail region comprising (1) the 5' terminal nucleotide of the primer (2) an innermost nucleotide, wherein the innermost nucleotide is downstream from the 5' terminal nucleotide (3) a middle section between the 5' terminal nucleotide and the innermost nucleotide, comprising one or more nucleotides, and (b) a template-binding region comprising (1) the 3' terminal nucleotide of the primer (2) an innermost nucleotide, wherein the innermost nucleotide is upstream from the 3' terminal nucleotide (3) a middle section between the 3' terminal nucleotide and the innermost nucleotide, comprising one or more nucleotides, and wherein the template-binding region is complementary to a second strand of the nucleic acid template, and wherein the tail region of the second primer contains a nucleotide sequence which is complementary to the nucleotide sequence of the tail region of the first primer, if the sequences are aligned such that the 5' terminal nucleotide of the second primer is aligned with the innermost nucleotide of the tail region of the first primer and the 5' terminal nucleotide of the first primer is aligned with the innermost nucleotide of the tail region of the second primer, and (B) incubating the reaction mixture for at least 3 minutes without thermocycling.

In some embodiments, provided herein is a method for generating a concatemer comprising two or more copies of a polynucleotide template, the method comprising, (A) preparing a reaction mixture comprising: (i) a nucleic acid comprising the polynucleotide template (ii) an isolated nucleic acid polymerase, (iii) a first primer comprising a 5' terminal nucleotide, a 3' terminal nucleotide, and two regions: (a) a tail region comprising (1) the 5' terminal nucleotide of the primer (2) an innermost nucleotide, wherein the innermost nucleotide is downstream from the 5' terminal nucleotide (3) a middle section between the 5' terminal nucleotide and the innermost nucleotide, comprising one or more nucleotides, and (b) a template-binding region comprising (1) the 3' terminal nucleotide of the primer (2) an innermost nucleotide, wherein the innermost nucleotide is upstream from the 3' terminal nucleotide (3) a middle section between the 3' terminal nucleotide and the innermost nucleotide, comprising one or more nucleotides, and wherein the template-binding region is complementary to the polynucleotide template, (iv) a second primer comprising a 5' terminal nucleotide, a 3' terminal nucleotide, and two regions: (a) a tail region comprising (1) the 5' terminal nucleotide of the primer (2) an innermost nucleotide, wherein the innermost nucleotide is downstream from the 5' terminal nucleotide (3) a middle section between the 5' terminal nucleotide and the innermost nucleotide, comprising one or more nucleotides, and (b) a template-binding region comprising (1) the 3' terminal nucleotide of the primer (2) an innermost nucleotide, wherein the innermost nucleotide is upstream from the 3' terminal nucleotide (3) a middle section between the 3' terminal nucleotide and the innermost nucleotide, comprising one or more nucleotides, and wherein the template-binding region is complementary to a nucleotide sequence complementary to the polynucleotide template, and wherein the tail region of the second primer contains a nucleotide sequence which is complementary to the nucleotide sequence of the tail region of the first primer, if the sequences of the primers are aligned such that the 5' terminal nucleotide of the second primer is aligned with the innermost nucleotide of the tail region of the first primer and the 5' terminal nucleotide of the first primer is aligned with the innermost nucleotide of the tail region of the second primer, and (B) incubating the reaction mixture at a temperature of no greater than 80 C for at least 3 minutes.

In some embodiments, provided herein is a method for generating a concatemer comprising two or more copies of a double-stranded nucleic acid template, the method comprising incubating together a first copy and a second copy of a double-stranded nucleic acid molecule comprising the double-stranded nucleic acid template and a polymerase, wherein the double-stranded nucleic acid molecule comprises a first strand and a second strand, each containing a plurality of nucleotides, the first strand comprises a 5' terminal nucleotide and a 3' terminal nucleotide and contains the general format of regions in the 5' to 3' direction: A1-B-A2, the second strand comprises a 5' terminal nucleotide and a 3' terminal nucleotide and contains the general format of regions in the 5' to 3' direction: C1-D-C2, region B comprises the nucleotide sequence a first strand of the double-stranded nucleic acid template, region D comprises the nucleotide sequence of a second strand of the double-stranded nucleic acid template, in the double-stranded nucleic acid molecule, region A1 is annealed to C2, B is annealed to D, and A2 is annealed to C1, a cross-over structure comprising the first strand of the first copy of the double-stranded nucleic acid molecule and the second strand of the second copy of the double-stranded nucleic acid molecule is generated, wherein the A2 region of the first strand is annealed to the C2 region of the second strand, an extension product of the first strand of the cross-over structure is synthesized and an extension product of the second strand of the cross-over structure is synthesized, to produce a concatemer comprising the extension product of the first strand of the cross-over structure annealed to the extension product of the second strand of the cross-over structure, wherein the concatemer contains two copies of the double-stranded nucleic acid template.

In embodiments, provided herein is a method of copying a polynucleotide template, the method comprising: incubating the polynucleotide template in a reaction mixture comprising multiple copies of a first primer and multiple copies of a second primer, wherein: the first primer comprises a first region and a second region, wherein the second region of the first primer comprises a nucleotide sequence which is complementary to a first portion of the polynucleotide template; the second primer comprises a first region and a second region, wherein the second region of the second primer comprises a nucleotide sequence which is complementary to a partner nucleotide sequence, wherein the partner nucleotide sequence is complementary to a second portion of the polynucleotide template; and upon incubation of the polynucleotide template with the multiple copies of the first primer and the multiple copies of the second primer, at least one concatemer strand is formed, wherein the concatemer strand comprises a 5' end and a 3' end, and comprises a nucleotide sequence having the general structure in the 5' to 3' direction of C'-T-C'-T-X-C', wherein: C' represents the nucleotide sequence of the first region of the second primer, T represents the nucleotide sequence of the polynucleotide template or an analogous sequence thereof, and X represents any number and sequence of nucleotides.

In some embodiments, in a method provided herein involving the formation of a concatemer strand which comprises a nucleotide sequence having the general structure in the 5' to 3' direction of: C'-T-C'-T-X-C', the concatemer strand is a first concatemer strand, and a second concatemer strand is also formed, wherein the second concatemer strand comprises a 5' end and a 3' end, and comprises a nucleotide sequence having the general structure in the 5' to 3' direction of: C-X'-T'-C-T'-C, wherein: C represents the nucleotide sequence of the first region of the first primer, T' represents a nucleotide sequence which is complementary to the polynucleotide template, and X' represents a nucleotide sequence which is complementary to the nucleotide sequence of X.

In embodiments, provided herein is method of assaying for a target polynucleotide template in a biological sample, the method comprising: A) incubating the biological sample or portion thereof in a reaction mixture comprising multiple copies of a first primer and multiple copies of a second primer, wherein: the first primer comprises a first region and a second region, wherein the second region of the first primer comprises a nucleotide sequence which is complementary to a first portion of the polynucleotide template; the second primer comprises a first region and a second region, wherein the second region of the second primer comprises a nucleotide sequence which is complementary to a partner nucleotide sequence, wherein the partner nucleotide sequence is complementary to a second portion of the polynucleotide template; and upon incubation of the polynucleotide template with the multiple copies of the first primer and the multiple copies of the second primer, at least one concatemer strand is formed, wherein the concatemer strand comprises a 5' end and a 3' end, and comprises a nucleotide sequence having the general structure in the 5' to 3' direction of: C'-T-C'-T-X-C', wherein: C' represents the nucleotide sequence of the first region of the second primer, T represents the nucleotide sequence of the polynucleotide template or an analogous sequence thereof, and X represents any number and sequence of nucleotides; and B) measuring an amount of amplified nucleic acid in the reaction mixture of A) at one or more points after the initiation of the incubating step of A). In embodiments, the measuring an amount of amplified nucleic acid in the reaction mixture may comprise determining a level of fluorescence in the reaction mixture. In embodiments, the method may further comprise determining an inflection time of nucleic acid amplification in the reaction mixture.

In embodiments, in a method, reaction mixture, vessel, or kit provided herein involving a concatemer strand which comprises a nucleotide sequence having the general structure in the 5' to 3' direction of: C'-T-C'-T-X-C', X may contain a sequence having the general structure in the 5' to 3' direction of $[(C'-T)_N]$ wherein C' represents the nucleotide sequence of the first region of the second primer, T represents the nucleotide sequence of the polynucleotide template or an analogous sequence thereof, and N is any integer between 0 and 2000. In embodiments, N may be any integer between 0 and 10, 0 and 100, 0 and 1000, 0 and 5000, 0 and 10,000 1 and 10, 1 and 100, 1 and 1000, 1 and 2000, 1 and 5000, or 1 and 10,000.

In embodiments, in 'a method, reaction mixture, vessel, or kit provided herein involving a concatemer strand which comprises a nucleotide sequence having the general structure in the 5' to 3' direction of: C'-T-C'-T-X-C', X may contain no more than 0, 1, 2, 3, 4, 5, 6, 7, 8, 9, 10, 15, 20, 25, 50, 100, 500, 1000, 10,000, 50,000, 100,000, or 500,000 nucleotides. In embodiments, in a method, vessel, or kit provided herein involving a concatemer strand which comprises a nucleotide sequence having the general structure in the 5' to 3' direction of: C'-T-C'-T-X-C', X may contain at least 1, 2, 3, 4, 5, 6, 7, 8, 9, 10, 15, 20, 25, 50, 100, 500, 1000, 10,000, 50,000, 100,000, or 500,000 nucleotides. In embodiments, in a method, vessel, or kit provided herein involving a concatemer strand which comprises a nucleotide sequence having the general structure in the 5' to 3' direction of: C'-T-C'-T-X-C', X may contain at least 1, 2, 3, 4, 5, 6, 7, 8, 9, 10, 15, 20, 25, 50, 100, 500, 1000, 10,000, 50,000, 100,000, nucleotides, and no more than 2, 3, 4, 5, 6, 7, 8, 9, 10, 15, 20, 25, 50, 100, 500, 1000, 10,000, 50,000, 100,000, or 500,000 nucleotides.

In embodiments, in a method, reaction mixture, vessel, or kit provided herein involving a concatemer strand which comprises a nucleotide sequence having the general structure in the 5' to 3' direction of: C'-T-C'-T-X-C', between at least one C' and T, one or more extra nucleotides are present which are not part of the C' or T sequence. The one or more extra nucleotides may be, for example, between 1 and 10, 1 and 20, 1 and 100, or 1 and 1000 nucleotides.

In embodiments, in a method, reaction mixture, vessel, or kit provided herein involving a concatemer strand which comprises a nucleotide sequence having the general structure in the 5' to 3' direction of: C'-T-C'-T-X-C', at least one C' or T sequence may be missing one or more nucleotides. In the event that 2 or more nucleotides are missing, the missing nucleotides may be contiguous, or may be at separate locations. The one or more missing nucleotides may be, for example, between 1 and 10, 1 and 20, 1 and 100, or 1 and 1000 nucleotides.

In embodiments, in a method, reaction mixture, vessel, or kit provided herein involving a concatemer strand which comprises a nucleotide sequence having the general structure in the 5' to 3' direction of: C'-T-C'-T-X-C', at least one C' or T sequence may have one or more point mutations. In the event that two or more point mutations are present, the point mutations may be contiguous, or may be at separate locations. The one or more point mutations may be, for example, between 1 and 10, 1 and 20, 1 and 100, or 1 and 1000 point mutations.

In embodiments, in a method, reaction mixture, vessel, or kit provided herein involving a concatemer strand which comprises a nucleotide sequence having the general structure in the 5' to 3' direction of: C'-T-C'-T-X-C', the nucleotide sequence has two or all three of the following characteristics: i) between at least one C' and T, one or more extra nucleotides are present which are not part of the C' or T sequence; ii) at least one C' or T sequence is missing one or more nucleotides; and iii) at least one C' or T sequence contains one or more point mutations.

In embodiments, in a method, reaction mixture, vessel, or kit provided herein involving a concatemer strand which comprises a nucleotide sequence having the general structure in the 5' to 3' direction of: C'-T-C'-T-X-C', in embodiments which the polynucleotide template is an RNA molecule, the T may represent the nucleotide sequence of a DNA sequence which is analogous to the RNA sequence of the polynucleotide template.

In embodiments, in a method, reaction mixture, vessel, or kit provided herein involving a concatemer strand which comprises a nucleotide sequence having the general structure in the 5' to 3' direction of: C'-T-C'-T-X-C', the concatemer strand further comprises one or more nucleotides to the 5' of the 5'-most situated C' sequence. The one or more nucleotides may be, for example, between 1 and 10, 1 and 20, 1 and 100, or 1 and 1000 nucleotides.

In embodiments, in a method, reaction mixture, vessel, or kit provided herein involving a concatemer strand which comprises a nucleotide sequence having the general structure in the 5' to 3' direction of: C'-T-C'-T-X-C', the concatemer strand further comprises one or more nucleotides to the 3' of the 3'-most situated C' sequence. The one or more nucleotides may be, for example, between 1 and 10, 1 and 20, 1 and 100, or 1 and 1000 nucleotides.

In embodiments, provided herein is a method of generating a concatemer comprising at least two copies of a double stranded nucleic acid template, the method comprising: incubating in a reaction mixture at least a first template molecule and a second template molecule, wherein: the first template molecule comprises a first nucleic acid strand and a second nucleic acid strand, wherein: the first nucleic acid strand of the first template molecule comprises a nucleotide sequence having the general structure in the 5' to 3' direction of: H'-S-$Y_1$-H', wherein: H' represents the nucleotide sequence of a first homology sequence, S represents the nucleotide sequence of a first strand of the double stranded nucleic acid template, and $Y_1$ represents any number and sequence of nucleotides; and the second nucleic acid strand of the first template molecule comprises a nucleotide sequence having the general structure in the 5' to 3' direction of: H-$Y_1$'-S'-H, wherein: H represents the nucleotide sequence of a second homology sequence, wherein the first homology sequence and second homology sequence are complementary to each other, $Y_1$' represents a nucleotide sequence which is complementary to the nucleotide sequence of $Y_1$, and S' represents the nucleotide sequence of a second strand of the double stranded nucleic acid template, wherein the first strand and second strand of the double stranded nucleic acid template are complementary to each other; and the second template molecule comprises a first nucleic acid strand and a second nucleic acid strand, wherein: the first nucleic acid strand of the second template molecule comprises a nucleotide sequence having the general structure in the 5' to 3' direction of: H'-S-$Y_2$-H', wherein: H' represents the nucleotide sequence of the first homology sequence, S represents the nucleotide sequence of the first strand of the double stranded nucleic acid template, and $Y_2$ represents any number and sequence of nucleotides; and the second nucleic acid strand of the first template molecule comprises a nucleotide sequence having the general structure in the 5' to 3' direction of: H-$Y_2$'-S'-H, wherein: H represents the nucleotide sequence of the second homology sequence, $Y_2$' represents a nucleotide sequence which is complementary to the nucleotide sequence of $Y_2$, and S' represents the nucleotide sequence of the second strand of the double stranded nucleic acid template; and upon incubation of the first template molecule with the second template molecule in the reaction mixture, at least one concatemer comprising at least two copies of the double stranded nucleic acid template is formed, wherein the concatemer comprises a first concatemer strand and a second concatemer strand, wherein the first concatemer strand comprises a 5' end and a 3' end, and comprises a nucleotide sequence having the general structure in the 5' to 3' direction of H'-S-$Y_2$-H'-S—$Y_1$-H', wherein each of H', $Y_1$, S, and $Y_2$ represent nucleotide sequences as described above; and wherein the second concatemer strand comprises a 5' end and a 3' end, and comprises a sequence having the general structure in the 5' to 3' direction of: H-$Y_1$'-S'-H-$Y_2$'-S'-H, wherein each of H', $Y_1$, S, and $Y_2$ represent nucleotide sequences as described above.

In embodiments, in a method, reaction mixture, vessel, or kit provided herein involving a first concatemer strand which comprises a nucleotide sequence having the general structure in the 5' to 3' direction of: H'-S-$Y_2$-H'-S—$Y_1$-H', at least one of or both $Y_1$ and $Y_2$ may represent 0 nucleotides.

In embodiments, in a method, reaction mixture, vessel, or kit provided herein involving a first concatemer strand which comprises a nucleotide sequence having the general structure in the 5' to 3' direction of: H'-S-$Y_2$-H'-S-$Y_1$-H', $Y_1$ may contain a sequence having the general structure in the 5' to 3' direction of [(H'-S)$_{N1}$] wherein H' and S represent nucleotide sequences as described above, and N1 is any integer between 0 and 2000.

In embodiments, in a method, reaction mixture, vessel, or kit provided herein involving a first concatemer strand which comprises a nucleotide sequence having the general structure in the 5' to 3' direction of: H'-S-$Y_2$-H'-S-$Y_1$-H', $Y_2$ may contain a sequence having the general structure in the 5' to 3' direction of [(H'-S)$_{N2}$] wherein H' and S represent nucleotide sequences as described above, and N2 is any integer between 0 and 2000.

In embodiments, in a method, reaction mixture, vessel, or kit provided herein involving a first template molecule and a second template molecule, the first template molecule and second template molecule are both double-stranded DNA molecules.

In embodiments, in a method, reaction mixture, vessel, or kit provided herein involving a first nucleic acid strand of a first template molecule comprises, wherein the first nucleic acid strand comprises a nucleotide sequence having the general structure in the 5' to 3' direction of: H'-S-$Y_1$-H', wherein H' represents the nucleotide sequence of a first homology sequence, the first homology sequence may contain no more than 4, 5, 6, 7, 8; 9, 10, 11, 12, 13, 14, 15, 20, 25, 30, 40, 50, 60, 70, 80, 90, or 100 nucleotides. In embodiments, the first homology sequence may contain at least 4, 5, 6, 7, 8, 9, 10, 11, 12, 13, 14, 15, 20, 25, 30, 40, 50, 60, 70, 80, 90, or 100 nucleotides. In embodiments, the first homology sequence may contain at least 4, 5, 6, 7, 8, 9, 10, 11, 12, 13, 14, 15, 20, 25, 30, 40, 50, 60, 70, 80, 90, or 100 and no more than 5, 6, 7, 8, 9, 10, 11, 12, 13, 14, 15, 20, 25, 30, 40, 50, 60, 70, 80, 90, 100, or 200 nucleotides.

In embodiments, a reaction mixture, vessel, or kit provided herein comprises a nucleic acid polymerase. In embodiments, a nucleic acid polymerase is a DNA polymerase having strand-displacement activity. In embodiments, a nucleic acid polymerase is an RNA polymerase. In embodiments, a nucleic acid polymerase is a reverse transcriptase. In embodiments, a reaction mixture, vessel, or kit comprises more than one kind of nucleic acid polymerase, such as both a DNA polymerase having strand displacement activity and a reverse transcriptase. In embodiments, a reaction mixture, vessel, or kit provided herein comprises nucleotides and buffer.

In embodiments, in a method, reaction mixture, vessel, or kit provided herein involving a polynucleotide template, the polynucleotide template is a single-stranded molecule. In embodiments, in a method, reaction mixture, vessel, or kit provided herein involving a polynucleotide template, the polynucleotide template comprises one strand of a double-stranded nucleic acid template. In embodiments, in a method, reaction mixture, vessel, or kit provided herein involving a polynucleotide template, the polynucleotide template is a DNA or RNA molecule.

In embodiments, in a method, reaction mixture, vessel, or kit provided herein involving a nucleic acid template, the nucleic acid template is an RNA or DNA molecule. In embodiments, a nucleic acid template may be a single-stranded or double-stranded molecule.

In embodiments, in a method provided herein involving incubation of a reaction mixture, during the incubation of the reaction mixture, the temperature of the reaction mixture does not exceed 90, 85, 80, 75, 70, 65, 60, 55, 50, 45, 40, 37, 35, 30, 25, or 20 C. In embodiments, in a method provided herein, all steps of the method are performed at a temperature of no greater than 90, 85, 80, 75, 70, 65, 60, 55, 50, 45, 40, 37, 35, 30, 25, or 20 C. In embodiments, a reaction mixture, vessel, or kit provided herein is maintained at a temperature of no greater than 90, 85, 80, 75, 70, 65, 60, 55, 50, 45, 40, 37, 35, 30, 25, or 20 C. In embodiments, a method provided herein is performed without thermocycling.

In embodiments, in a method, reaction mixture, vessel, or kit provided herein involving a polynucleotide template comprising a first portion, the first portion contains no more than 5, 10, 15, 20, 25, 30, 35, 40, 50, 60, 70, 80, 90, 100, or 200 nucleotides. In embodiments, in a method, reaction mixture, vessel, or kit provided herein involving a polynucleotide template comprising a first portion, the first portion contains at least 5, 10, 15, 20, 25, 30, 35, 40, 50, 60, 70, 80, 90, 100, or 200 nucleotides. In embodiments, in a method, reaction mixture, vessel, or kit provided herein involving a polynucleotide template comprising a first portion, the first portion contains at least 5, 10, 15, 20, 25, 30, 35, 40, 50, 60, 70, 80, 90, or 100 and no more than 10, 15, 20, 25, 30, 35, 40, 50, 60, 70, 80, 90, 100, or 200 nucleotides.

In embodiments, in a method, reaction mixture, vessel, or kit provided herein involving a primer comprising a first region, the first region contains at least 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a first region, the first region contains no more than 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a first region, the first region contains at least 4, 5, 6, 7, 8, 9, 10, 11, 12, 13, 14, 15, 20, 25, 30, 35, 40, 50, 60, 70, 80, or 90 and no more than 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a first primer comprising a first region and a second primer comprising a first region, both the first primer and second primer may have any of the features described above. In embodiments, in a method, reaction mixture, vessel, or kit provided herein involving a first primer comprising a first region and a second primer comprising a first region, the first region of the first primer and the first region of the second primer may contain the same number of nucleotides. In embodiments, in a method, reaction mixture, vessel, or kit provided herein involving a first primer comprising a first region and a second primer comprising a first region, the first region of the first primer and the first region of the second primer may contain a different number of nucleotides.

In embodiments, in a method, reaction mixture, vessel, or kit provided herein involving a primer comprising a second region, the second region contains at least 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a second region, the second region contains no more than 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a second region, the second region contains at least 4, 5, 6, 7, 8, 9, 10, 11, 12, 13, 14, 15, 20, 25, 30, 35, 40, 50, 60, 70, 80, or 90 and no more than 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a first primer comprising a second region and a second primer comprising a second region, both the first primer and second primer may have any of the features described above. In embodiments, in a method, reaction mixture, vessel, or kit provided herein involving a first primer comprising a second region and a second primer comprising a second region, the second region of the first primer and the second region of the second primer may contain the same number of nucleotides. In embodiments, in a method, reaction mixture, vessel, or kit provided herein involving a first primer comprising a second region and a second primer comprising a second region, the second region of the first primer and the second region of the second primer may contain a different number of nucleotides.

In embodiments, in a method, reaction mixture, vessel, or kit provided herein involving a second primer containing a second region and a polynucleotide template comprising a second portion, the nucleotide sequence of the second region of the second primer is the same as the nucleotide sequence of the second portion of the polynucleotide template.

In embodiments, in a method, reaction mixture, vessel, or kit provided herein involving a primer comprising a tail region, the tail region contains at least 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a tail region, the tail region contains no more than 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a tail region, the tail region contains at least 4, 5, 6, 7, 8, 9, 10, 11, 12, 13, 14, 15, 20, 25, 30, 35, 40, 50, 60, 70, 80, or 90 and no more than 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a first primer comprising a tail region and a second primer comprising a tail region, both the first primer and second primer may have any of the features described above. In embodiments, in a method, reaction mixture, vessel, or kit provided herein involving a first primer comprising a tail region and a second primer comprising a tail region, the tail region of the first primer and the tail region of the second primer may contain the same number of nucleotides. In embodiments, in a method, reaction mixture, vessel, or kit provided herein involving a first primer comprising a tail region and a second primer comprising a tail region, the tail region of the first primer and the tail region of the second primer may contain a different number of nucleotides.

In embodiments, in a method, reaction mixture, vessel, or kit provided herein involving a primer comprising a template-binding region, the second region contains at least 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a template-binding region, the template-binding region contains no more than 4, 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a primer comprising a template-binding region, the template-binding region contains at least 4, 5, 6, 7, 8, 9, 10, 11, 12, 13, 14, 15, 20, 25, 30, 35, 40, 50, 60, 70, 80, or 90 and no more than 5, 6, 7, 8, 9, 10, 11, 12, 13, 14, 15, 20, 25, 30, 35, 40, 50, 60, 70, 80, 90, or 100 nucleotides. In embodiments, in a method, reaction mixture, vessel, or kit provided herein involving a first primer comprising a template-binding region and a second primer comprising a template-binding region, both the first primer and second primer may have any of the features described above. In embodiments, in a method, reaction mixture, vessel, or kit provided herein involving a first primer comprising a template-binding region and a second primer comprising a template-binding region, the template-binding region of the first primer and the template-binding region of the second primer may contain the same number of nucleotides. In embodiments, in a method, reaction mixture, vessel, or kit provided herein involving a first primer comprising a template-binding region and a second primer comprising a template-binding region, the template-binding region of the first primer and the template-binding region of the second primer may contain a different number of nucleotides.

In embodiments, in a method, reaction mixture, vessel, or kit provided herein involving a polynucleotide template, the polynucleotide template may contain at least 8, 9, 10, 11, 12, 13, 14, 15, 20, 25, 30, 35, 40, 50, 60, 70, 80, 90, 100, 200, 500, 1000, 2000, or 5000 nucleotides. In embodiments, in a method, reaction mixture, vessel, or kit provided herein involving a polynucleotide template, the polynucleotide template may contain no more than 8, 9, 10, 11, 12, 13, 14, 15, 20, 25, 30, 35, 40, 50, 60, 70, 80, 90, 100, 200, 500, 1000, 2000, 5000, or 10,000 nucleotides. In embodiments, in a method, reaction mixture, vessel, or kit provided herein involving a polynucleotide template, the polynucleotide template may contain at least 8, 9, 10, 11, 12, 13, 14, 15, 20, 25, 30, 35, 40, 50, 60, 70, 80, 90, 100, 200, 500, 1000, 2000, or 5000, and no more than 9, 10, 11, 12, 13, 14, 15, 20, 25, 30, 35, 40, 50, 60, 70, 80, 90, 100, 200, 500, 1000, 2000, 5000, or 10,000 nucleotides.

In embodiments, in a method, reaction mixture, vessel, or kit provided herein involving a double-stranded nucleic acid template, each strand of the double-stranded nucleic acid template may contain at least 8, 9, 10, 11, 12, 13, 14, 15, 20, 25, 30, 35, 40, 50, 60, 70, 80, 90, 100, 200, 500, 1000, 2000, or 5000 nucleotides. In embodiments, in a method, reaction mixture, vessel, or kit provided herein involving a double-stranded nucleic acid template, each strand of the double-stranded nucleic acid template may contain no more than 8, 9, 10, 11, 12, 13, 14, 15, 20, 25, 30, 35, 40, 50, 60, 70, 80, 90, 100, 200, 500, 1000, 2000, 5000, or 10,000 nucleotides. In embodiments, in a method, reaction mixture, vessel, or kit provided herein involving a double-stranded nucleic acid template, each strand of the double-stranded nucleic acid template may contain at least 8, 9, 10, 11, 12, 13, 14, 15, 20, 25, 30, 35, 40, 50, 60, 70, 80, 90, 100, 200, 500, 1000, 2000, or 5000, and no more than 9, 10, 11, 12, 13, 14, 15, 20, 25, 30, 35, 40, 50, 60, 70, 80, 90, 100, 200, 500, 1000, 2000, 5000, or 10,000 nucleotides.

In embodiments, a reaction mixture, vessel, or kit provided herein does not contain a recombinase enzyme.

In embodiments, in a method, reaction mixture, vessel, or kit provided herein may contain or involve multiple copies of a primer. The multiple copies may be, for example, at least 5, 10, 15, 20, 50, 100, 500, 1000, 10,000, 100,000, or 1,000,000 copies of the primer.

In embodiments, a reaction mixture or vessel provided herein may comprise at least a portion of a biological sample from a subject. The biological sample may be, for example, saliva, blood, urine, a cheek swab, or a nasal swab. The subject may be a human.

In some embodiments, all of the steps of a method provided herein are performed at a temperature of no greater than 70, 65, 60, 65, 60, 55, 50, 45, 40, 35, 30, 25, 20, 15, or 10 C. In some embodiments, some of the steps of a method provided herein are performed at a temperature of no greater than 70, 65, 60, 65, 60, 55, 50, 45, 40, 35, 30, 25, 20, 15, or 10 C.

In some embodiments, two or more steps of a method provided herein are performed simultaneously in the same reaction mixture. In some embodiments, all of the steps of a method provided herein are performed simultaneously in the same reaction mixture.

In some embodiments, in a method provided herein, a nucleic acid template is amplified at least 10, 100, 1000, 10,000, 100,000, or 1,000,000-fold within 5, 10, 15, 20, 30, 40, 50, 60, 70, 80, 90, 120, or 180 minutes of initiation of the method. In some embodiments, in a method provided herein, the number of copies of a nucleic acid template in a reaction mixture is increased least 10, 100, 1000, 10,000, 100,000, or 1,000,000-fold within 5, 10, 15, 20, 30, 40, 50, 60, 70, 80, 90, 120, or 180 minutes of initiation of the method.

In embodiments, a nucleic acid template provided herein may be a single-stranded or a double-stranded nucleic acid template.

In embodiments, provided herein is a vessel, comprising in fluid communication therein: a first primer, wherein the first primer comprises a first region and a second region, and wherein the second region of the first primer comprises a nucleotide sequence which is complementary to a first portion of a polynucleotide template; a second primer, wherein the second primer comprises a first region and a second region, and wherein the second region of the second primer comprises a nucleotide sequence which is complementary to a partner nucleotide sequence, wherein the partner nucleotide sequence is complementary to a second portion of the polynucleotide template; and at least one concatemer strand, wherein the concatemer strand comprises a 5' end and a 3' end, and comprises a nucleotide sequence having the general structure in the 5' to 3' direction of: C'-T-C'-T-X-C', wherein: C' represents the nucleotide sequence of the first region of the second primer, T represents the nucleotide sequence of the polynucleotide template or an analogous sequence thereof, and X represents any number and sequence of nucleotides.

In some embodiments, provided herein is a vessel, comprising in fluid communication therein: (A) an isolated nucleic acid polymerase, (B) a nucleic acid template comprising at least a first strand, (C) a first primer comprising a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, wherein the template-binding region is complementary to a first strand of the nucleic acid template, and (D) a second primer comprising a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, and wherein the template-binding region is complementary to a nucleotide sequence complementary to first strand of the nucleic acid template, and wherein the tail region of the second primer contains a nucleotide sequence which is complementary to the nucleotide sequence of the tail region of the first primer, if the sequences of the primers are aligned such that the 5' terminal nucleotide of the second primer is aligned with the innermost nucleotide of the tail region of the first primer and the 5' terminal nucleotide of the first primer is aligned with the innermost nucleotide of the tail region of the second primer.

In embodiments, provided herein is a kit comprising two or more fluidically isolated containers, the containers collectively comprising: a first primer, wherein the first primer comprises a first region and a second region, and wherein the second region of the first primer comprises a nucleotide sequence which is complementary to a first portion of a polynucleotide template; a second primer, wherein the second primer comprises a first region and a second region, and wherein the second region of the second primer comprises a nucleotide sequence which is complementary to a partner nucleotide sequence, wherein the partner nucleotide sequence is complementary to a second portion of the polynucleotide template; and an isolated DNA polymerase having strand-displacement activity; wherein: the first region of the first primer and the first region of the second primer are complementary.

In some embodiments, provided herein is a kit for detecting a target nucleic acid of interest comprising at least a first strand, the kit comprising two or more fluidically isolated containers, the containers collectively comprising: (A) an isolated nucleic acid polymerase, (B) a first primer comprising a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, wherein the template-binding region is complementary to the first strand of the target nucleic acid, and (C) a second primer comprising a 5' terminal nucleotide, a 3' terminal nucleotide, and two regions: (i) a tail region comprising (a) the 5' terminal nucleotide of the primer (b) an innermost nucleotide, wherein the innermost nucleotide is downstream from the 5' terminal nucleotide (c) a middle section between the 5' terminal nucleotide and the innermost nucleotide, comprising one or more nucleotides, and (ii) a template-binding region comprising (a) the 3' terminal nucleotide of the primer (b) an innermost nucleotide, wherein the innermost nucleotide is upstream from the 3' terminal nucleotide (c) a middle section between the 3' terminal nucleotide and the innermost nucleotide, comprising one or more nucleotides, and wherein the template-binding region is complementary to a nucleotide sequence complementary to the first strand of the target nucleic acid, and wherein the tail region of the second primer contains a nucleotide sequence which is complementary to the nucleotide sequence of the tail region of the first primer, if the sequences of the primers are aligned such that the 5' terminal nucleotide of the second primer is aligned with the innermost nucleotide of the tail region of the first primer and the 5' terminal nucleotide of the first primer is aligned with the innermost nucleotide of the tail region of the second primer.

In some embodiments, a kit provided herein comprises a nucleic acid having the nucleotide sequence of the target nucleic acid of interest.

In some embodiments, a reaction mixture, vessel or kit provided herein comprises a nucleic acid dye.

In some embodiments, in a vessel or kit provided herein comprising an isolated nucleic acid polymerase, the isolated nucleic acid polymerase is a DNA polymerase. In some embodiments, in a vessel or kit provided herein comprising an isolated nucleic acid polymerase, the isolated nucleic acid polymerase is a reverse transcriptase. In some embodiments, in a vessel or kit provided herein comprising an isolated nucleic acid polymerase, the vessel or kit comprises both a DNA polymerase and a reverse transcriptase.

In some embodiments, in a method, vessel, or kit provided herein comprising a nucleic acid polymerase, the nucleic acid polymerase has strand displacement activity.

In some embodiments, a method provided herein comprises treating one or more of the reaction components or steps of the method with a nucleic acid dye.

In some embodiments, in a method, vessel, or kit provided herein comprising a nucleic acid template, the template is a DNA molecule. In some embodiments, in a method, vessel, or kit provided herein comprising a nucleic acid template, the template is an RNA molecule.

In some embodiments, in a method, vessel, or kit provided herein comprising a first primer, the tail region of the first primer comprises at least 4, 5, 6, 7, 8, 9, 10, 11, 12, 13, 14, 15, 16, 17, 18, 19, or 20 nucleotides. In some embodiments, in a method, vessel, or kit provided herein comprising a first primer, the tail region of the first primer comprises no more than 4, 5, 6, 7, 8, 9, 10, 11, 12, 13, 14, 15, 16, 17, 18, 19, 20, 30, 40, 50, or 60 nucleotides.

In some embodiments, in a method, vessel, or kit provided herein comprising a second primer, the tail region of the second primer comprises at least 4, 5, 6, 7, 8, 9, 10, 11, 12, 13, 14, 15, 16, 17, 18, 19, or 20 nucleotides. In some embodiments, in a method, vessel, or kit provided herein comprising a second primer, the tail region of the second primer comprises no more than 4, 5, 6, 7, 8, 9, 10, 11, 12, 13, 14, 15, 16, 17, 18, 19, 20, 30, 40, 50, or 60 nucleotides.

In some embodiments, in a method, vessel, or kit provided herein comprising a first primer, the template-binding region of the first primer comprises at least 4, 5, 6, 7, 8, 9, 10, 11, 12, 13, 14, 15, 16, 17, 18, 19, or 20 nucleotides. In some embodiments, in a method, vessel, or kit provided herein comprising a first primer, the template-binding region of the first primer comprises no more than 4, 5, 6, 7, 8, 9, 10, 11, 12, 13, 14, 15, 16, 17, 18, 19, 20, 30, 40, 50, or 60 nucleotides.

In some embodiments, in a method, vessel, or kit provided herein comprising a second primer, the template-binding region of the second primer comprises at least 4, 5, 6, 7, 8, 9, 10, 11, 12, 13, 14, 15, 16, 17, 18, 19, or 20 nucleotides. In some embodiments, in a method, vessel, or kit provided herein comprising a second primer, the template-binding region of the second primer comprises no more than 4, 5, 6, 7, 8, 9, 10, 11, 12, 13, 14, 15, 16, 17, 18, 19, 20, 30, 40, 50, or 60 nucleotides.

In some embodiments, in methods and compositions provided herein wherein an RNA molecule is the template molecule or primary nucleic acid, amplification of the template may refer to generation of copies of DNA strands corresponding to the RNA molecule.

In some embodiments, a method provided herein comprises measuring a fluorescent signal from an assay comprising the method.

In some embodiments, a nucleic acid ligase may be included with a method or composition provided herein. In some embodiments, a nucleic acid template may be amplified more rapidly with a method provided herein when a ligase is included in a reaction mixture for a method provided herein, as compared to if a nucleic acid ligase is not included in the reaction. In embodiments, a reaction mixture, vessel, or kit provided herein may contain an enzyme having ligase activity.

In embodiments, provided herein is a method of assaying for a pathogen in a sample, the method comprising performing a method as provided herein to amplify nucleic acid from the pathogen. In embodiments, the target nucleic acid used in a composition or method provided herein may be nucleic acid from a pathogen. In embodiments, the first and second primer used in a method provided herein may each contain regions which are complementary to a sequence in the nucleic acid of the pathogen, or which are complementary to a sequence which is complementary to a sequence in the nucleic acid of the pathogen. In embodiments, the nucleic acid of the pathogen may be DNA or RNA. Pathogens may include, without limitation, viruses, bacteria, fungi, and protists. A sample may be from a subject, and may have any of the sample characteristics described elsewhere herein.

In embodiments, a method provided herein for amplification of a nucleic acid may be used for a diagnostic method externally of a human or animal body. For example, a sample may be obtained from a human or animal, and the sample may be assayed for a target nucleic acid of interest with a method provided herein for amplification of nucleic acid.

In embodiments, a method provided herein may include: a) providing one or more reagents for performing a method as provided herein (e.g. one or more of first primer, second primer, nucleic acid template, nucleic acid polymerase, nucleotides, buffer, water, etc.) in a reaction mixture, and b) incubating the reaction mixture at a substantially isothermal temperature, wherein the temperature of the reaction mixture does not diverge from a central temperature by more or less than 20, 15, 10, 9, 8, 7, 6, 5, 4, 3, 2, or 1 degree Celsius during the incubation. In embodiments, a central temperature may be, for example, 30, 35, 40, 45, 50, 55, 60, 65, 70, 75, or 80 degrees Celsius.

In embodiments, a method provided herein may be performed at a substantially isothermal temperature. In embodiments, a substantially isothermal temperature may be any of 30, 35, 40, 45, 50, 55, 60, 65, 70, 75, or 80 degrees Celsius, plus or minus 20, 15, 10, 9, 8, 7, 6, 5, 4, 3, 2, or 1 degree Celsius.

In embodiments, a method provided herein may be performed at one or more temperatures, none or which exceed 90, 85, 80, 75, 70, 65, 60, 55, 50, 45, 40, 35, 30, or 25 degrees Celsius.

In compositions and methods provided herein involving a first primer comprising a first region and a second primer comprising a first region, wherein the first region of the first primer is complementary to the first region of the second primer, in embodiments, the first region of the first primer and the first region of the second primer contain nucleotide sequences such that a double stranded structure which would be formed by the annealing of the first region of the first primer to the first region of the second primer according to Watson-Crick base pairing rules would not form a restriction enzyme recognition sequence.

In compositions and methods provided herein involving a nucleic acid polymerase, in embodiments, the nucleic acid polymerase has 3' to 5' exonuclease activity.

References herein to generating a copy of or amplifying a polynucleotide template or nucleic acid template include generating a copy which contains the sequence of the polynucleotide template/nucleic acid template, as well as generating a copy which contains an analogous sequence of the polynucleotide template/nucleic acid template, unless the context clearly dictates otherwise. For instance, if a polynucleotide template is RNA, generating a copy of the template can include generating a copy which is a DNA molecule which contains the DNA version of the RNA sequence of the polynucleotide template (i.e. in the DNA sequence, contains Ts instead of Us).

BRIEF DESCRIPTION OF THE DRAWINGS

In the drawings,

FIGS. 1A-1K depict a general schematic of a method provided herein. FIGS. 1A-1K include the following nucleotide sequences: 103: AACGGTTGCTC (SEQ ID NO: 1); 104: GAGCAACCGTT (SEQ ID NO: 2); 105: ATGGGAGC (SEQ ID NO: 3); 106: CCATAACG (SEQ ID NO: 4); 111: ATGGGAGCAACCGTT (SEQ ID NO: 5); 112: CCATAACGGTTGCTCCCAT (SEQ ID NO: 6); 113: ATGGGAGCAACCGTTATGG (SEQ ID NO: 7); 121: CCATAACGGTTGCTCCCATAACGGTTGCTCCCAT (SEQ ID NO: 8); 122: ATGGGAGCAACCGT-TATGGGAGCAACCGTTATGG (SEQ ID NO: 9).

FIG. 2A includes the following nucleotide sequences:

```
P1 primer, 37 nucleotides:
                                    (SEQ ID NO: 10)
CGCCGGATGGCTCTTGGGAAACCAAACCGTACCAACC;

P1 primer, 35 nucleotides:
                                    (SEQ ID NO: 11)
CCGGATGGCTCTTGGGAAACCAAACCGTACCAACC;

P1 primer, 33 nucleotides:
                                    (SEQ ID NO: 12)
GGATGGCTCTTGGGAAACCAAACCGTACCAACC;

P1 primer, 31 nucleotides:
                                    (SEQ ID NO: 13)
ATGGCTCTTGGGAAACCAAACCGTACCAACC;
```

-continued

P1 primer, 30 nucleotides:
(SEQ ID NO: 14)
TGGCTCTTGGGAAACCAAACCGTACCAACC;

P1 primer, 29 nucleotides:
(SEQ ID NO: 15)
GGCTCTTGGGAAACCAAACCGTACCAACC;

P1 primer, 28 nucleotides:
(SEQ ID NO: 16)
GCTCTTGGGAAACCAAACCGTACCAACC;

P1 primer, 27 nucleotides:
(SEQ ID NO: 17)
CTCTTGGGAAACCAAACCGTACCAACC;

P1 primer, 26 nucleotides:
(SEQ ID NO: 18)
TCTTGGGAAACCAAACCGTACCAACC;

P1 primer, 25 nucleotides:
(SEQ ID NO: 19)
CTTGGGAAACCAAACCGTACCAACC;

P1 primer, 24 nucleotides:
(SEQ ID NO: 20)
TTGGGAAACCAAACCGTACCAACC;

P1 primer, 23 nucleotides:
(SEQ ID NO: 21)
TGGGAAACCAAACCGTACCAACC;

P2 primer, 36 nucleotides:
(SEQ ID NO: 22)
GTTTCCCAAGAGCCATCCGGCGATGCGGAATGTACC;

P2 primer, 34 nucleotides:
(SEQ ID NO: 23)
GTTTCCCAAGAGCCATCCGGATGCGGAATGTACC;

P2 primer, 32 nucleotides:
(SEQ ID NO: 24)
GTTTCCCAAGAGCCATCCATGCGGAATGTACC;

P2 primer, 30 nucleotides:
(SEQ ID NO: 25)
GTTTCCCAAGAGCCATATGCGGAATGTACC;

P2 primer, 29 nucleotides:
(SEQ ID NO: 26)
GTTTCCCAAGAGCCAATGCGGAATGTACC;

P2 primer, 28 nucleotides:
(SEQ ID NO: 27)
GTTTCCCAAGAGCCATGCGGAATGTACC;

P2 primer, 27 nucleotides:
(SEQ ID NO: 28)
GTTTCCCAAGAGCATGCGGAATGTACC;

P2 primer, 26 nucleotides:
(SEQ ID NO: 29)
GTTTCCCAAGAGATGCGGAATGTACC;

P2 primer, 25 nucleotides:
(SEQ ID NO: 30)
GTTTCCCAAGAATGCGGAATGTACC;

P2 primer, 24 nucleotides:
(SEQ ID NO: 31)
GYTTCCCAAGATGCGGAATGTACC;

P2 primer, 23 nucleotides:
(SEQ ID NO: 32)
GTTTCCCAAATGCGGAATGTACC;
and

P2 primer, 22 nucleotides:
(SEQ ID NO: 33)
GTTTCCCAATGCGGAATGTACC.

Figure 2B:
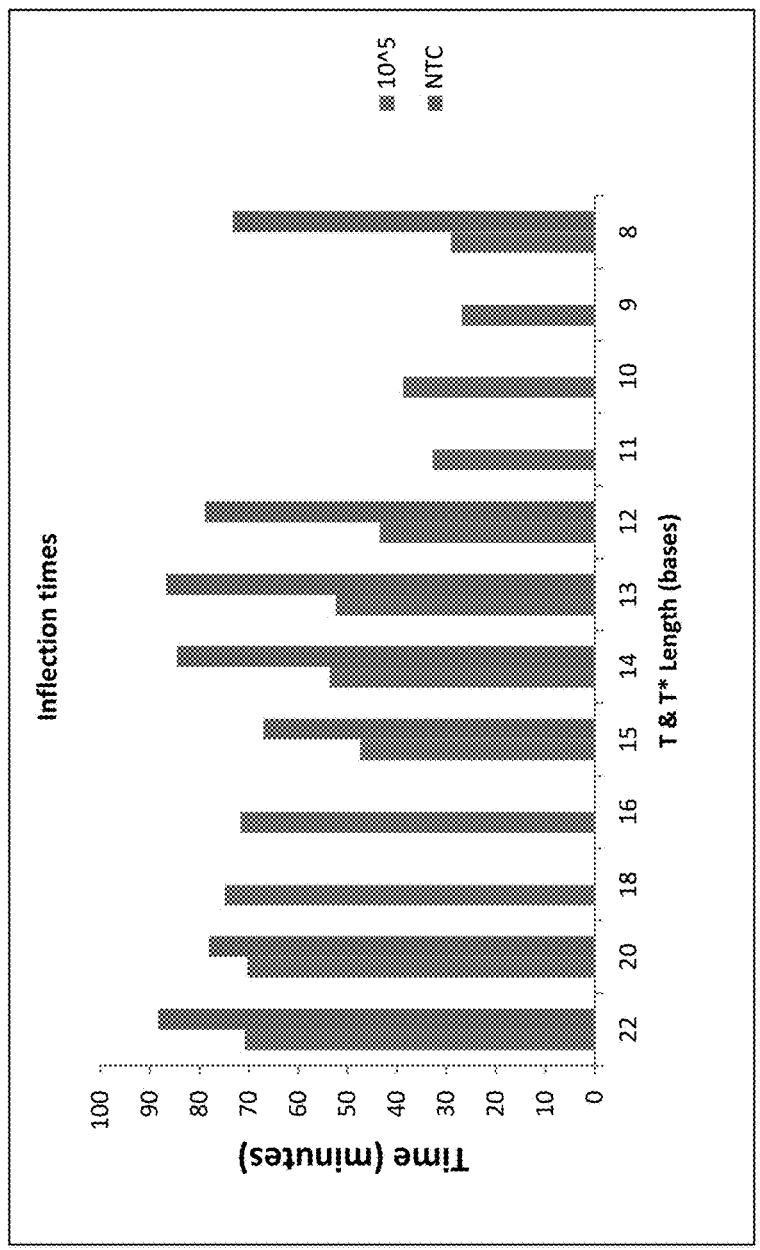
FIG. 2A shows nucleotide sequences of certain primers used with methods provided herein.

FIG. 2B is a graph depicting results from reactions performed according to a method provided herein.

Figure 3B:
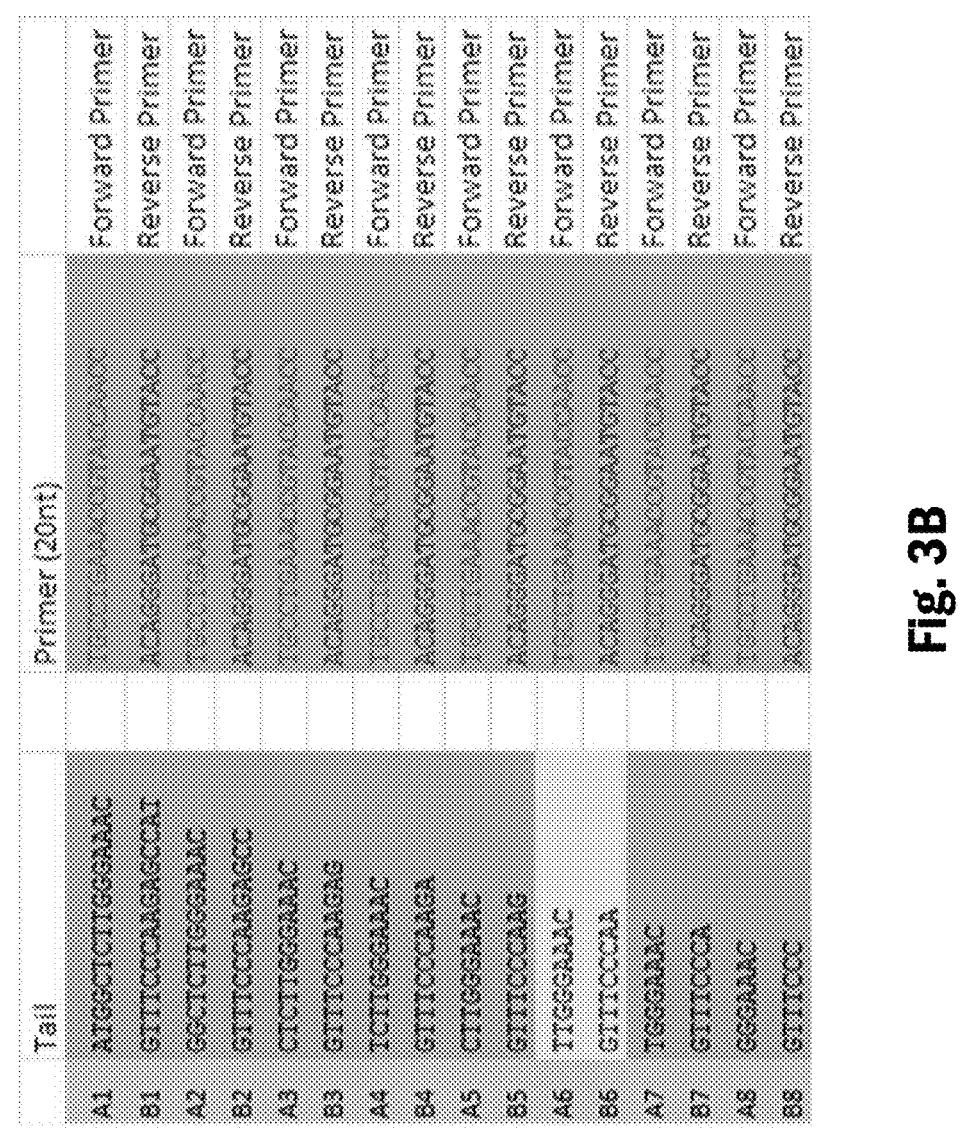

FIGS. 3A and 3B show nucleotide sequences of certain primers used with methods provided herein.

FIG. 3A includes the following nucleotide sequences:
(SEQ ID NO: 34)
C5: ATGGCTCTTGGGAAACTGAAACCGTACCAACC;

(SEQ ID NO: 35)
D5: GTTTCCCAAGAGCCATGGATGCGGAATGTACC;

(SEQ ID NO: 36)
C6: GGCTCTTGGGAAACTGAAACCGTACCAACC;

(SEQ ID NO: 37)
D6: GTTTCCCAAGAGCCGGATGCGGAATGTACC;

(SEQ ID NO: 38)
C7: CTCTTGGGAAACTGAAACCGTACCAACC;

(SEQ ID NO: 39)
D7: GTTTCCCAAGAGGGATGCGGAATGTACC;

(SEQ ID NO: 40)
C8: TCTTGGGAAACTGAAACCGTACCAACC;

(SEQ ID NO: 41)
D8: GTTTCCCAAGAGGATGCGGAATGTACC;

(SEQ ID NO: 42)
C9: CTTGGGAAACTGAAACCGTACCAACC;

(SEQ. ID NO: 43)
D9: GTTTCCCAAGGGATGCGGAATGTACC;

(SEQ ID NO: 44)
C10: TTGGGAAACTGAAACCGTACCAACC;

(SEQ ID NO: 45)
D10: GTTTCCCAAGGATGCGGAATGTACC;

(SEQ ID NO: 46)
C11: TGGGAAACTGAAACCGTACCAACC;

(SEQ ID NO: 47)
D11: GTTTCCCAGGATGCGGAATGTACC;

(SEQ ID NO: 48)
C12: GGGAAACTGAAACCGTACCAACC;
and (SEQ ID NO: 49)
D12: GTTTCCCGGATGCGGAATGTACC.

FIG. 3B includes the following nucleotide sequences:
(SEQ ID NO: 50)
A1: ATGGCTCTTGGGAAACTGCCTGAAACCGTACCAACC;

(SEQ ID NO: 51)
B1: GTTTCCCAAGAGCCATACAGGGATGCGGAATGTACC;

(SEQ ID NO: 52)
A2: GGCTCTTGGGAAACTGCCTGAAACCGTACCAACC;

(SEQ ID NO: 53)
B2: GTTTCCCAAGAGCCACAGGGATGCGGAATGTACC;

(SEQ ID NO: 54)
A3: CTCTTGGGAAACTGCCTGAAACCGTACCAACC;

(SEQ ID NO: 55)
B3: GTTTCCCAAGAGACAGGGATGCGGAATGTACC;

(SEQ ID NO: 56)
A4: TCTTGGGAAACTGCCTGAAACCGTACCAACC;

-continued

B4: GTTTCCCAAGAACAGGGATGCGGAATGTACC; (SEQ ID NO: 57)

A5: CTTGGGAAACTGCCTGAAACCGTACCAACC; (SEQ ID NO: 58)

B5: GTTTCCCAAGACAGGGATGCGGAATGTACC; (SEQ ID NO: 59)

A6: TTGGGAAACTGCCTGAAACCGTACCAACC; (SEQ ID NO: 60)

B6: GTTTCCCAAACAGGGATGCGGAATGTACC; (SEQ ID NO: 61)

A7: TGGGAAACTGCCTGAAACCGTACCAACC; (SEQ ID NO: 62)

B7: GTTTCCCAACAGGGATGCGGAATGTACC; (SEQ ID NO: 63)

A8: GGGAAACTGCCTGAAACCGTACCAACC; and (SEQ ID NO: 64)

B8: GTTTCCCACAGGGATGCGGAATGTACC. (SEQ ID NO: 65)

FIGS. 3C and 3D are graphs depicting results from reactions performed according to a method provided herein.

Figure 4:
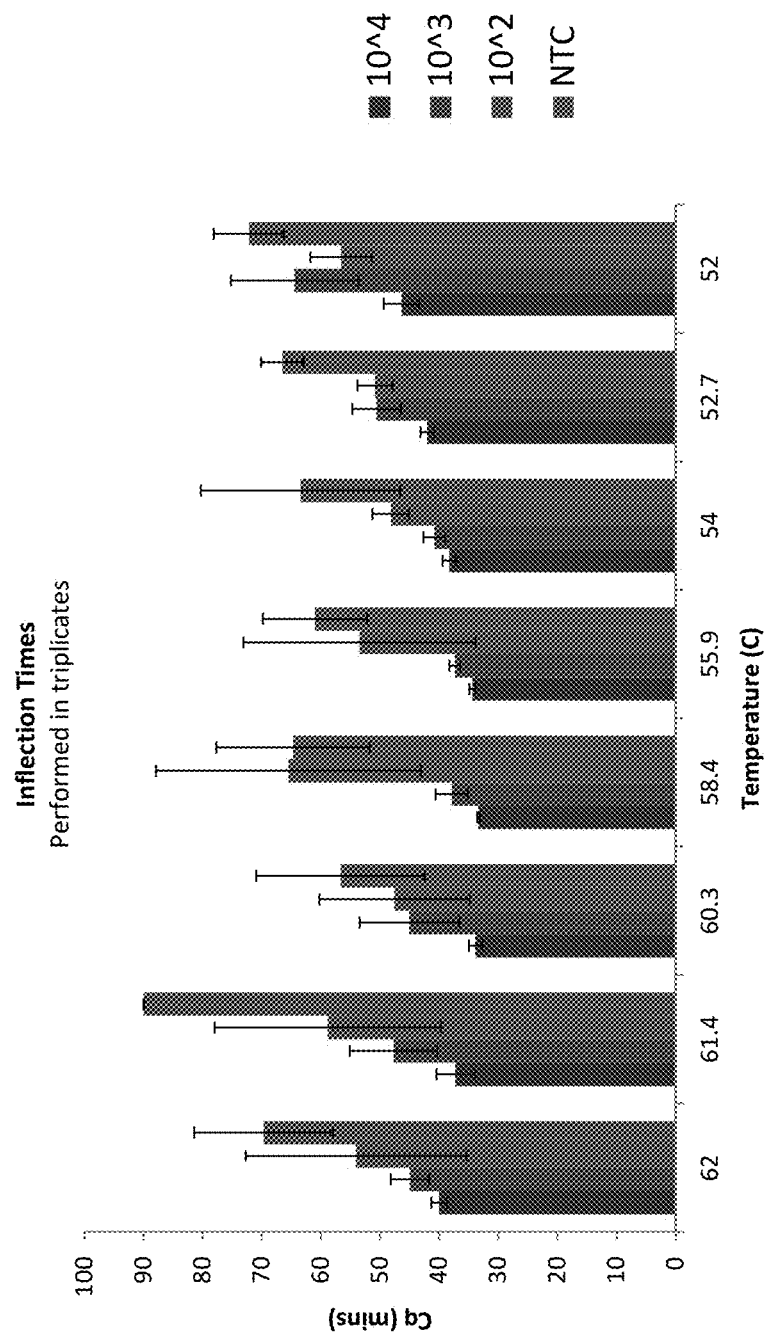

FIG. 4 is a graph depicting results from reactions performed according to a method provided herein.

Figure 5:
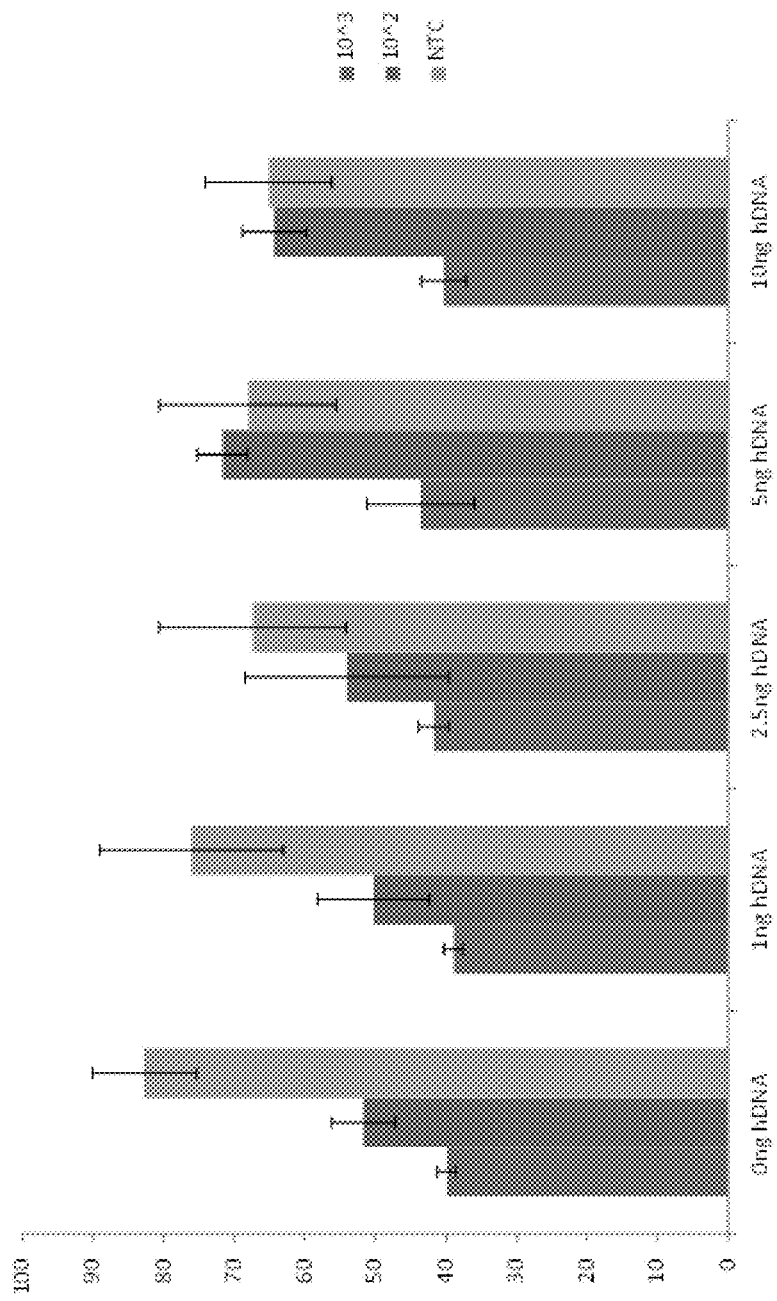

FIG. 5 is a graph depicting results from reactions performed according to a method provided herein.

Figure 6:
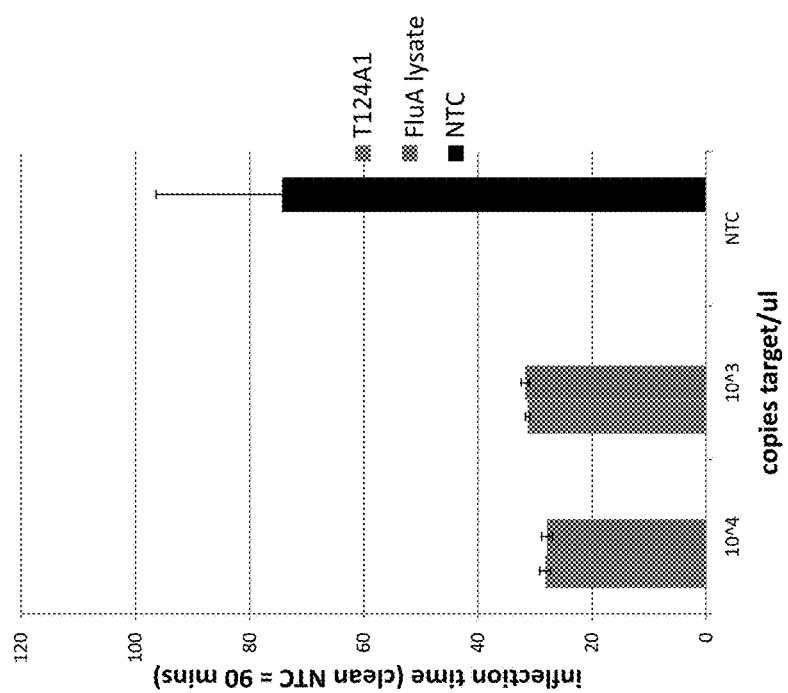

FIG. 6 is a graph depicting results from reactions performed according to a method provided herein.

Figure 7:
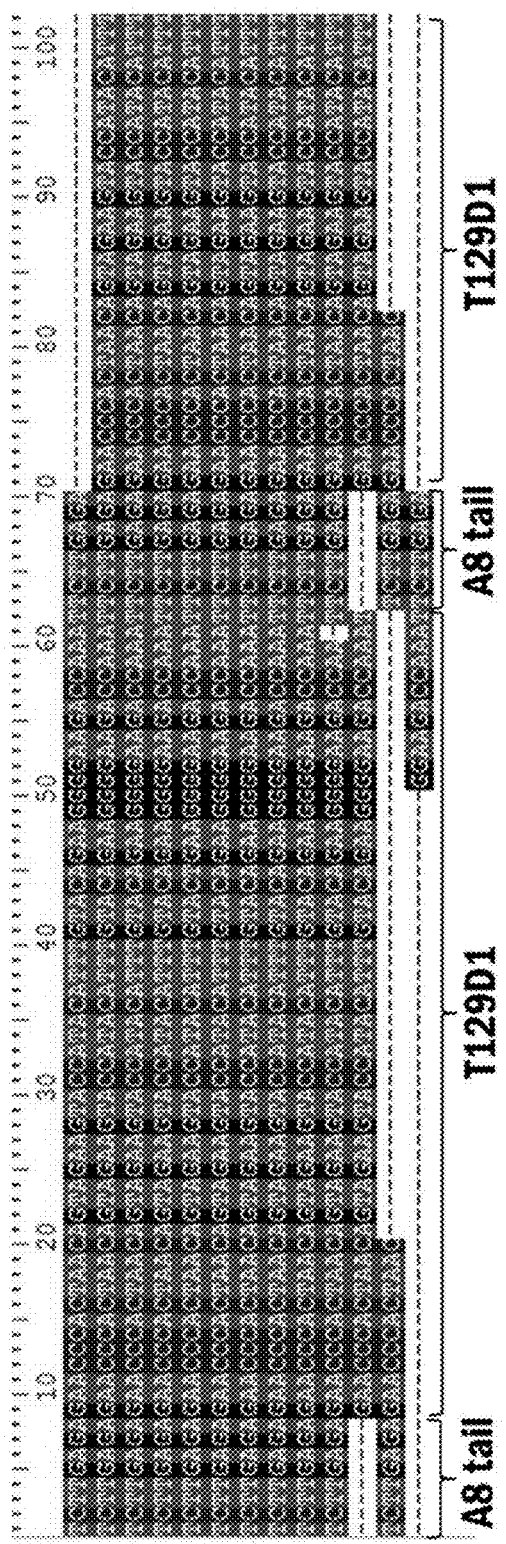

FIG. 7 is a sequence alignment depicting the nucleotide sequences of products generated in reactions performed according to a method provided herein. FIG. 7 includes the following nucleotide sequences (in order from the top sequence in the alignment to the bottom sequence in the alignment):

SEQ ID NO: 66:
TCTTGAGAGAACCCACTAACAGTAGAAGTACCATACATTTGTACAGAAGG

GGAAGACCAAATTCTTGAGA;

SEQ ID NO: 67:
TCTTGAGAGAACCCACTAACAGTAGAAGTACCATACATTTGTACAGAAGG

GGAAGACCAAATTCTTGAGAGAACCCACTAACAGTAGAAGTACCATACAT

TT;

SEQ ID NO: 68:
TCTTGAGAGAACCCACTAACAGTAGAAGTACCATACATTTGTACAGAAGG

GGAAGACCAAATTCTTGAGAGAACCCACTAACAGTAGAAGTACCATACAT

TT;

SEQ ID NO: 69:
TCTTGAGAGAACCCACTAACAGTAGAAGTACCATACATTTGTACAGAAGG

GGAAGACCAAATTCTTGAGAGAACCCACTAACAGTAGAAGTACCATACAT

TT;

SEQ ID NO: 70:
TCTTGAGAGAACCCACTAACAGTAGAAGTACCATACATTTGTACTGAAGG

GGAAGACCAAATTCTTGAGAGAACCCACTAACAGTAGAAGTACCATACAT

TT;

-continued

SEQ ID NO: 71:
TCTTGAGAGAACCCACTAACAGTAGAAGTACCATACATTTGTACAGAAGG

GGAAGACCAAATTCTTGAGAGAACCCACTAACAGTAGAAGTACCATACAT

TT;

SEQ ID NO: 72:
TCTTGAGAGAACCCACTAACAGTAGAAGTACCATACATTTGTACAGAAGG

GGAAGACCAAATTCTTGAGAGAACCCACTAACAGTAGAAGTACCATACAT

TT;

SEQ ID NO: 73:
TCTTGAGAGAACCCACTAACAGTAGAAGTACCATACATTTGTACAGAAGG

GGAAGACCAAATTCTTGAGAGAACCCACTAACAGTAGAAGTACCATACAT

TT;

SEQ ID NO: 74:
TCTTGAGAGAACCCACTAACAGTAGAAGTACCATACATTTGTACAGAAGG

GGAAGACCAAATTCTTGAGAGAACCCACTAACAGTAGAAGTACCATACAT

TT;

SEQ ID NO: 75:
TCTTGAGAGAACCCACTAACAGTAGAAGTACCATACATTTGTACAGAAGG

GGAAGACCAATTCTTGAGAGAACCCACTAACAGTAGAAGTACCATACATT

T;

SEQ ID NO: 76:
GAACCCACTAACAGTAGAAGTACCATACATTTGTACAGAAGGGGAAGACC

AAATGAACCCACTAACAGTAGAAGTACCATACATTT;

SEQ ID NO: 77:
TCTTGAGAGAACCCACTAACTCTTGAGAGAACCCACTAAC; and

SEQ ID NO: 78:
GGAAGACCAAATTCTTGAGA.

Figure 8A:
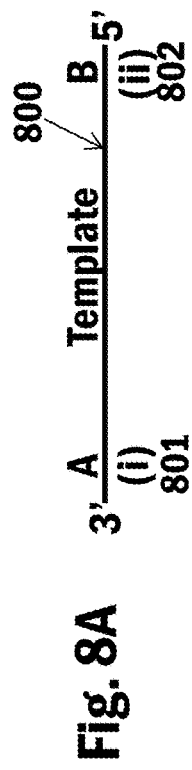
Figure 8B:
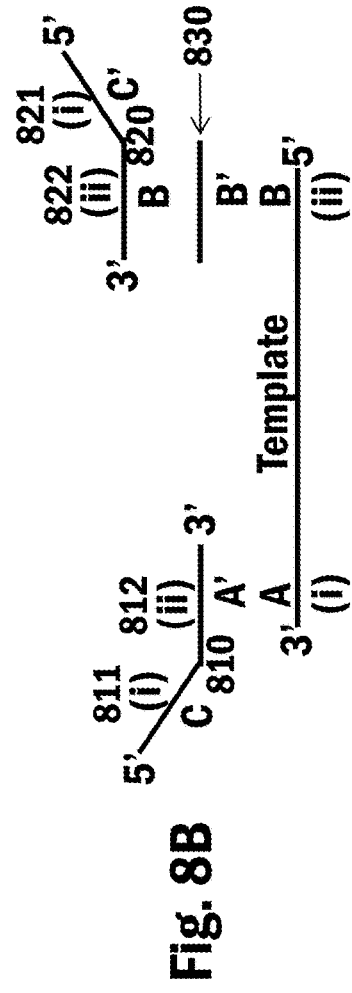
Figure 8C:
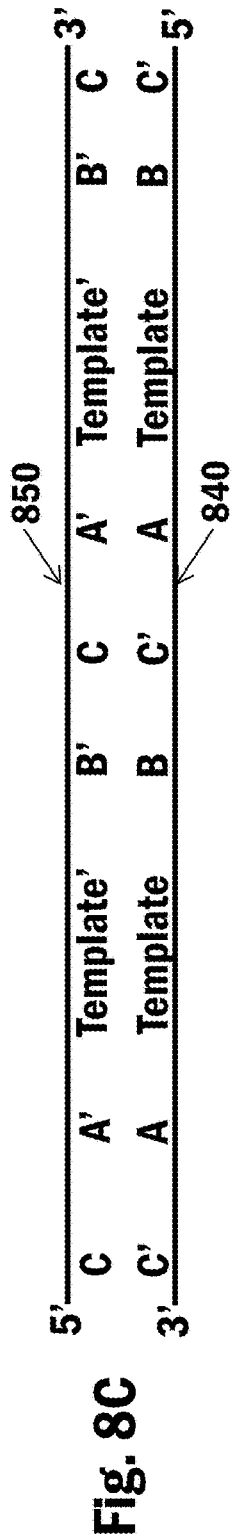

FIGS. 8A-8C are general schematics of features of embodiments of molecules provided herein. It is noted that the drawings and elements therein are not necessarily drawn to shape or scale. For example, the shape or scale of elements of the drawings may be simplified or modified for ease or clarity of presentation. It should further be understood that the drawings and elements therein are for exemplary illustrative purposes only, and not be construed as limiting in any way.

DETAILED DESCRIPTION

While the invention includes various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims.

In some embodiments, provided herein are methods and compositions relating to the amplification of nucleic acids and the generation of concatemers.

In methods provided herein, generation of nucleic acid concatemers also amplifies the number of copies of the nucleic acid template/particular nucleic acid in the concatemer. Accordingly, references herein to methods and compositions for the generation of concatemers also apply to the amplification of nucleic acids.

As used herein, a "polynucleotide" refers to a polymeric chain containing two or more nucleotides. "Polynucleotides" includes primers, oligonucleotides, nucleic acid strands, etc. A polynucleotide may contain standard or non-standard nucleotides. Typically, a polynucleotide contains a 5' phosphate at one terminus ("5' terminus") and a 3' hydroxyl group at the other terminus ("3' terminus) of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide.

The term "downstream" as used herein in the context of a polynucleotide containing a 5' terminal nucleotide and a 3' terminal nucleotide refers to a position in the polynucleotide which is closer to the 3' terminal nucleotide than a reference position in the polynucleotide. For example, in a primer having the sequence: 5' ATAAGC 3', the "G" is downstream from the"T" and all of the "A"s.

The term "upstream" as used herein in the context of a polynucleotide containing a 5' terminal nucleotide and a 3' terminal nucleotide, refers to a position in the polynucleotide which is closer to the 5' terminal nucleotide than a reference position in the polynucleotide. For example, in a primer having the sequence: 5' ATAAGC 3', the "T" is upstream from the "G", the "C", and the two "A"s closest to the "G".

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded.

As used herein, a "concatemer" refers to a nucleic acid molecule which contains within it two or more copies of a particular nucleic acid, wherein the copies are linked in series. Within the concatemer, the copies of the particular nucleic acid may be linked directly to each other, or they may be indirectly linked (e.g. there may be nucleotides between the copies of the particular nucleic acid). In an example, the particular nucleic acid may be that of a double-stranded nucleic acid template, such that a concatemer may contain two or more copies of the double-stranded nucleic acid template. In another example, the particular nucleic acid may be that of a polynucleotide template, such that a concatemer may contain two or more copies of the polynucleotide template.

As used herein, a "target" nucleic acid or molecule refers to a nucleic acid of interest. A target nucleic acid/molecule may be of any type, including single-stranded or double stranded DNA or RNA (e.g. mRNA).

As used herein, "complementary" sequences refer to two nucleotide sequences which, when aligned anti-parallel to each other, contain multiple individual nucleotide bases which can pair with each other according to standard base-pairing rules (e.g. A-T, G-C, or A-U), such that molecules containing the sequences can specifically anneal to each other. It is not necessary for every nucleotide base in two sequences to be capable of pairing with each other for the sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences can pair with each other when the sequences are optimally aligned for complementation. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer can pair with nucleotide bases in the longer polynucleotide when the primer is aligned anti-parallel to a particular region of the longer polynucleotide. Additionally, "complementary" sequences may contain one or more nucleotide analogs or nucleobase analogs.

As used herein, the term "isolated" as applied to proteins, nucleic acids, or other biomolecules refers to a molecule that has been purified or separated from a component of its naturally-occurring environment (e.g. a protein purified from a cell in which it was naturally produced). An "isolated" molecule may be in contact with other molecules (for example, as part of a reaction mixture). As used herein, "isolated" molecules also include recombinantly-produced proteins or nucleic acids which have an amino acid or nucleotide sequence which occurs naturally. "Isolated" nucleic acids include polypeptide-encoding nucleic acid molecules contained in cells that ordinarily express the polypeptide where, for example, the nucleic acid molecule is at a chromosomal location different from that of natural cells. In some embodiments, "isolated" polypeptides are purified to at least 50%, 60%, 70%, 80%, 90%, 95%, 98%, or 100% homogeneity as evidenced by SDS-PAGE of the polypeptides followed by Coomassie blue, silver, or other protein staining method.

As used herein, a nucleic acid molecule which is described as containing the "sequence" of a template or other nucleic acid may also be considered to contain the template or other nucleic acid itself (e.g. a molecule which is described as containing the sequence of a template may also be described as containing the template), unless the context clearly dictates otherwise.

As used herein, when a first polynucleotide is described as "annealed", "annealing" or the like to a second polynucleotide, the entirety of the first polynucleotide or any portion thereof may anneal to the second polynucleotide, and vice versa.

As used herein, a reference to "treating" a given object to a condition or other object or the like refers to directly or indirectly exposing the given object to the recited condition or other object. Thus, while a "treating" step may involve a distinct related action (e.g. adding an enzyme to a vessel, shaking a vessel, etc.), not every "treating" step requires a distinct related action. For example, a reaction involving one or more reagents can be set up in a vessel, and once the reaction has been initiated, multiple events or steps may occur in the vessel without further human or mechanical intervention with the contents of the vessel. One or more of these multiple events or steps in the vessel may be described as "treating" an object in the vessel, even if no separate intervention with the contents of the vessel occurs after the initiation of the reaction.

Figure 1A:
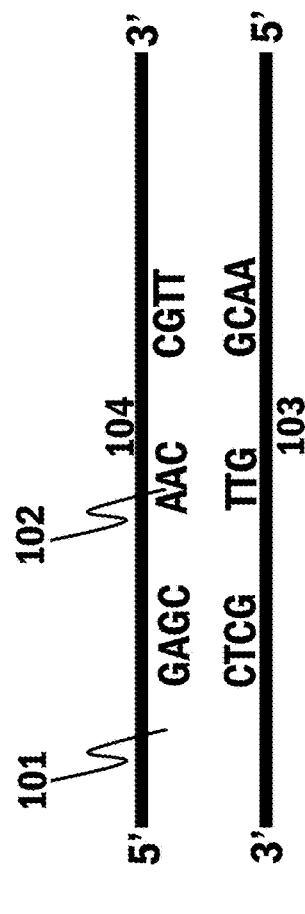

Embodiments of methods and compositions provided herein may be described with reference to FIG. 1. A primary nucleic acid 101 may be provided (FIG. 1A). The primary nucleic acid 101 may contain the sequence of a nucleic acid template 102. The nucleic acid template 102 may be a double-stranded nucleic acid containing a first strand 103 and a second strand 104. In FIG. 1, the first strand 103 of the double-stranded nucleic acid template has an exemplary nucleotide sequence in the 5' to 3' direction of: AACGGT-TGCTC (SEQ ID NO: 1). The first strand 103 also contains a 5' terminal nucleotide (the 5'-most A) and a 3' terminal nucleotide (the 3'-most C). The second strand 104 has an exemplary nucleotide sequence in the 5' to 3' direction of:

GAGCAACCGTT (SEQ ID NO: 2). The second strand 104 also contains a 5' terminal nucleotide (the 5'-most G) and a 3' terminal nucleotide (the 3'-most T).

Figure 1B:
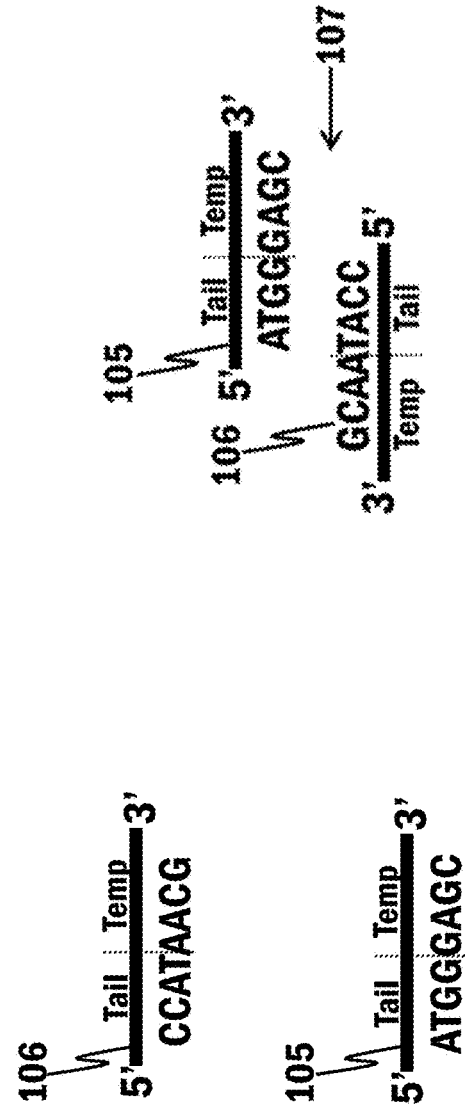
Figure 1E:
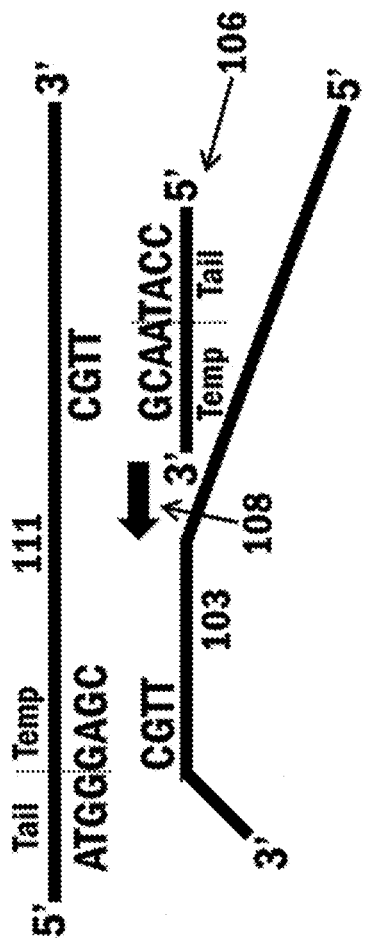

A first primer 105 and a second primer 106 may also be provided (FIG. 1B). In FIG. 1, the first primer 105 has an exemplary nucleotide sequence in the 5' to 3' direction of: ATGGGAGC (SEQ ID NO: 3). The first primer also contains a 5' terminal nucleotide (the 5'-most A) and a 3' terminal nucleotide (the 3'-most C). The second primer 106 has an exemplary nucleotide sequence in the 5' to 3' direction of: CCATAACG (SEQ ID NO: 4). The second primer also contains a 5' terminal nucleotide (the 5'-most C) and a 3' terminal nucleotide (the 3'-most G). Although nucleic acid template 102 of FIG. 1 is 11 nucleotides in length and has an exemplary nucleotide sequence, these are exemplary, and not to be considered as limiting.

The first primer 105 may comprise two regions: i) a tail region and ii) a template-binding region ("temp" region). The tail region of the first primer 105 may contain three components: a) the 5' terminal nucleotide of the primer, b) an innermost nucleotide, wherein the innermost nucleotide is downstream from the 5' terminal nucleotide, and c) a middle section between the 5' terminal nucleotide and the innermost nucleotide, comprising one or more nucleotides. In FIG. 1, the tail region of the first primer 105 has an exemplary nucleotide sequence in the 5' to 3' direction of: ATGG, of which the 5' terminal nucleotide of the primer is the A, the middle section is the middle TG, and the innermost nucleotide is the 3'-most G. The template-binding region of the first primer 105 may contain three components: a) the 3' terminal nucleotide of the primer, b) an innermost nucleotide, wherein the innermost nucleotide is upstream from the 3' terminal nucleotide, and c) a middle section between the 3' terminal nucleotide and the innermost nucleotide, comprising one or more nucleotides. In FIG. 1, the template-binding region of the first primer 105 has an exemplary nucleotide sequence in the 5' to 3' direction of: GAGC, of which the 3' terminal nucleotide of the primer is the C, the middle section is the middle AG, and the innermost nucleotide is the 5'-most G.

The second primer 106 may comprise two regions: i) a tail region and ii) a template-binding region. The tail region of the first primer 106 may contain three components: a) the 5' terminal nucleotide of the primer, b) an innermost nucleotide, wherein the innermost nucleotide is downstream from the 5' terminal nucleotide, and c) a middle section between the 5' terminal nucleotide and the innermost nucleotide, comprising one or more nucleotides. In FIG. 1, the tail region of the second primer 106 has an exemplary nucleotide sequence in the 5' to 3' direction of: CCAT, of which the 5' terminal nucleotide of the primer is the 5'-most C, the middle section is the middle CA, and the innermost nucleotide is the T. The template-binding region of the second primer 106 may contain three components: a) the 3' terminal nucleotide of the primer, b) an innermost nucleotide, wherein the innermost nucleotide is upstream from the 3' terminal nucleotide, and c) a middle section between the 3' terminal nucleotide and the innermost nucleotide, comprising one or more nucleotides. In FIG. 1, the template-binding region of the second primer 106 has an exemplary nucleotide sequence in the 5' to 3' direction of: AACG, of which the 3' terminal nucleotide of the primer is the G, the middle section is the middle AC, and the innermost nucleotide is the 5'-most A.

In some embodiments, the tail region of the second primer may contain a nucleotide sequence which is complementary to the nucleotide sequence of the tail region of the first primer, if the sequences of the primers are aligned such that the 5' terminal nucleotide of the second primer is aligned with the innermost nucleotide of the tail region of the first primer and the 5' terminal nucleotide of the first primer is aligned with the innermost nucleotide of the tail region of the second primer. For example, in FIG. 1, the tail region of the second primer 106 has a nucleotide sequence in the 5' to 3' direction of CCAT, and the tail region of the first primer 105 has a nucleotide sequence in the 5' to 3' direction of ATGG. These sequences are complementary when the 5' terminal nucleotide of the second primer (C) is aligned with the innermost nucleotide of the tail region of the first primer (G) and the 5' terminal nucleotide of the first primer (A) is aligned with the innermost nucleotide of the tail region of the second primer (T) 107 (FIG. 1B).

It should be noted that although the tail region of the second primer may contain a nucleotide sequence which is complementary to the nucleotide sequence of the tail region of the first primer, typically, products formed by the annealing of the first primer to the second primer are not desirable or useful for methods or compositions provided herein. Accordingly, in some embodiments, steps may be taken to minimize the formation of first primer-second primer annealed products. Such steps may include, for example, not pre-incubating a first primer and a second primer under conditions where the primers may interact for an extended period of time before initiating a method provided herein.

The primary nucleic acid 101 may be treated with a first copy of the first primer 105a and a polymerase 108 under conditions such that the template-binding region of the first copy of the first primer 105a anneals to the first strand of the nucleic acid template 103 (FIG. 1C) and an extension product of the first copy of the first primer 111 is formed (FIG. 1D). The polymerase 108 may catalyze the formation of the extension product of the first copy of the first primer 111. The polymerase may have strand displacement activity. During the synthesis of the extension product of the first copy of the first primer 111, the polymerase may displace the second strand of the nucleic acid template 104 from the first strand of the nucleic acid template 103. Typically, the extension product is generated from the 3' end of the first copy of the first primer 105a. During the generation of the extension product of the first copy of the first primer 111, the first copy of the first primer 105a may be covalently linked to the synthesized extension product, such that the first copy of the first primer becomes part of the molecule described herein as the "extension product of the first copy of the first primer". The extension product of the first copy of the first primer 111 is complementary to the first strand of the nucleic acid template 103. In some embodiments, when the first copy of the first primer 105a anneals to the first strand of the nucleic acid template 103, the template-binding region but not the tail region of the first copy of the first primer 105a anneals to the first strand of the nucleic acid template.

In some embodiments, conditions such that the template-binding region of the first copy of the first primer 105a anneals to the first strand of the nucleic acid template 103 and an extension product of the first copy of the first primer 111 is formed may include any condition sufficient to support polymerase-based nucleic acid synthesis. Example conditions for polymerase-based nucleic acid synthesis are known in the art and are provided, for example, in Molecular Cloning: A Laboratory Manual, M. R. Green and J. Sambrook, Cold Spring Harbor Laboratory Press (2012), which is herein incorporated by reference in its entirety. In embodiments, the template-binding region of the first primer or second primer may support template-dependent extension of the primer by a nucleic acid polymerase, which may extend the primer from the primer's 3' end.

Figure 1F:
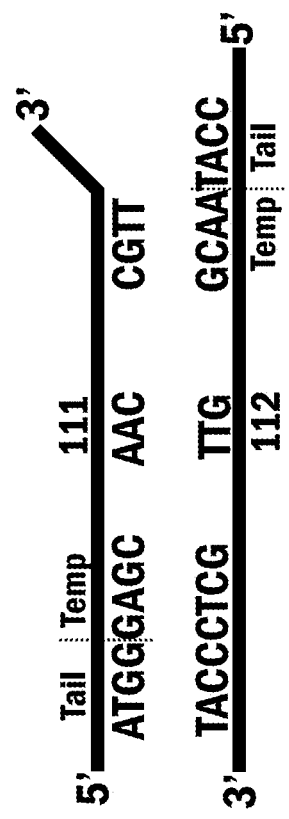
Figure 1G:
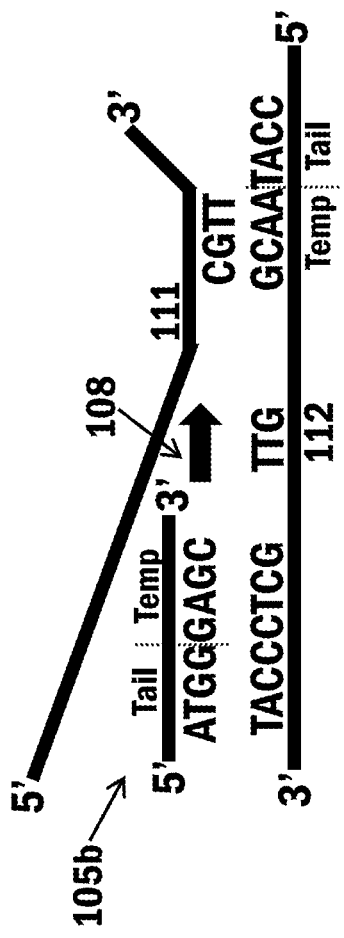

The extension product of the first copy of the first primer 111 may be treated with the second primer 106 and a polymerase 108 under conditions such that the template-binding region of the second primer 106 anneals to the extension product of the first copy of the first primer 111 (FIG. 1E) and an extension product of the second primer 112 is formed (FIG. 1F). The polymerase 108 may catalyze the formation of the extension product of the second primer 106. The polymerase may have strand displacement activity. The polymerase may be the same type of polymerase as is used to generate an extension product of the first copy of the first primer 111, or it may be different. During the synthesis of the extension product of the second primer 112, the polymerase may displace the first strand of the nucleic acid template 103 from the extension product of the first copy of the first primer 111. Typically, the extension product is generated from the 3' end of the second primer 106. During the generation of the extension product of the second primer 112, the second primer 106 may be covalently linked to the synthesized extension product, such that the second primer becomes part of the molecule described herein as the "extension product of the second primer". The extension product of the second primer 112 is complementary to the extension product of the first copy of the first primer 111. In some embodiments, when the second primer 106 anneals to the extension product of the first copy of the first primer 111, the template-binding region but not the tail region of the second primer 106 anneals to the extension product of the first copy of the first primer 111. The extension product of the second primer 112 contains a 5' terminal nucleotide, a 3' terminal nucleotide, and a 3' terminal region. The final nucleotide of the 3' terminal region (T) is the 3' terminal nucleotide of the extension product of the second primer (T), and the 3' terminal region contains the same nucleotide sequence as the nucleotide sequence of the tail region of the second primer read in the 5' to 3' direction (CCAT).

In some embodiments, conditions such that the template-binding region of the second primer 106 anneals to the extension product of the first copy of the first primer 111 and an extension product of the second primer 112 is formed may include any condition sufficient to support polymerase-based nucleic acid synthesis, including any condition discussed elsewhere herein. The conditions may be the same as used to generate an extension product of the first copy of the first primer 111, or they may be different.

Figure 1H:
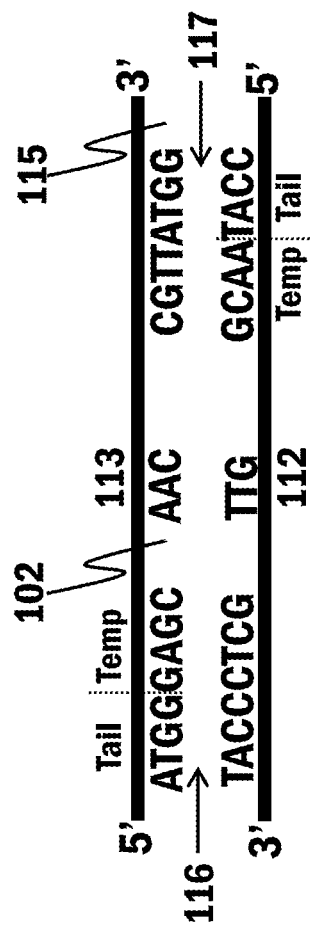

The extension product of the second primer 112 may be treated with a second copy of the first primer 105b and a polymerase 108 under conditions such that the template-binding region of the second copy of the first primer 105b anneals to the extension product of the second primer 112 (FIG. 1G) and an extension product of the second copy of the first primer 113 is formed (FIG. 1H). The polymerase 108 may catalyze the formation of the extension product of the second copy of the first primer 113. The polymerase may have strand displacement activity. The polymerase may be the same type of polymerase as is used to generate an extension product of the first copy of the first primer 111 or an extension product of the second primer 112, or it may be different. During the synthesis of the extension product of the second copy of the first primer 113, the polymerase may displace the extension product of the first copy of the first primer 111 from the extension product of the second primer 112. Typically, the extension product is generated from the 3' end of the second copy of the first primer 105b. During the generation of the extension product of the second copy of the first primer 113, the second copy of the first primer 105b may be covalently linked to the synthesized extension product, such that the second copy of the first primer becomes part of the molecule described herein as the "extension product of the second copy of the first primer". The extension product of the second copy of the first primer 113 is complementary to the extension product of the second primer 112. In some embodiments, when the second copy of the first primer 105b anneals to the extension product of the second primer 112, both the template-binding region and the tail region of the second copy of the first primer 105b anneals to the extension product of the second primer 112. The extension product of the second copy of the first primer 113 contains a 5' terminal nucleotide, a 3' terminal nucleotide, and a 3' terminal region. The final nucleotide of the 3' terminal region (G) is the 3' terminal nucleotide of the extension product of the second primer (G), and the 3' terminal region contains the same nucleotide sequence as the nucleotide sequence of the tail region of the first primer read in the 5' to 3' direction (ATGG).

In some embodiments, conditions such that the template-binding region of the second copy of the first primer 105b anneals to the extension product of the second primer 112 and an extension product of the second copy of the first primer 113 is formed may include any condition sufficient to support polymerase-based nucleic acid synthesis, including any condition discussed elsewhere herein. The conditions may be the same as used to generate an extension product of the first copy of the first primer 111 or an extension product of the second primer 112, or they may be different.

Generation of the extension product of the second copy of the first primer 113 may result in the generation of a molecule comprising the extension product of the second copy of the first primer 113 and the extension product of the second primer 112, which may be referred to herein as the "secondary nucleic acid" 115. Within the secondary nucleic acid 115, the extension product of the second copy of the first primer 113 may be annealed to the extension product of the second primer 112. In addition, the secondary nucleic acid 115 contains the sequence of the nucleic acid template 102. The secondary nucleic acid 115 has a greater nucleotide length than the nucleic acid template 102 alone, as in addition to the sequence of the nucleic acid template 102, it may include the sequence of the tail regions of the first primer and the second primer, and complementary sequences thereof. Specifically, a secondary nucleic acid 115 may have a first end region 116 and a second end region 117. The first end region 116 may comprise the 3' terminal region of the extension product of the second primer 112, and the complement thereof. The second end region 117 may comprise the 3' terminal region of the extension product of the second copy of the first primer 113, and the complement thereof.

A first copy 115a and a second copy 115b of the secondary nucleic acid 115 may be formed or provided (FIG. 1I). The first copy 115a and second copy 115b of the secondary nucleic acid 115 may be generated by any process whereby a nucleic acid having the general structure of the secondary nucleic acid 115 may be generated, including any process discussed elsewhere herein. For example, the full process as described above for generating a secondary nucleic acid 115 from a primary nucleic acid 101 may be repeated two times, in order to generate the first copy 115a and the second copy 115b of the secondary nucleic acid. In another example, the first copy 115a and the second copy 115b of the secondary nucleic acid may be generated from a single copy of an extension product of a first copy of first primer 111. In this example, two copies 112a, 112b of an extension product of the second primer may be generated from the single copy of the extension product of a first copy of a first primer 111, which may occur if a first copy of the extension product of the second primer 112a is displaced from the single copy of the extension product of the first copy of the first primer 111, thereby permitting the generation of a second copy of the extension product of the second primer 112b from the single copy of the extension product of a first copy of a first primer 111. Then, for example, an extension product of the second copy of the first primer 113a, 113b may be generated from each copy of the extension product of the second primer 112a, 112b, respectively. Additional procedures for the generation of a first copy 115a and a second copy 115b of the secondary nucleic acid may also be performed and used with methods provided herein.

The first copy 115a and second copy 115b of the secondary nucleic acid may be treated under conditions such that the 3' terminal region of the extension product of the second copy of the first primer of the first copy of the secondary nucleic acid 113a anneals to the 3' terminal region of the extension product of the second primer of the second copy of the secondary nucleic acid 112b, to produce a cross-over structure 118 comprising these strands (FIG. 1J) (for simplicity, strands 113b and 112a are not shown). The cross-over structure 118 may be further treated with a polymerase under conditions such that extension products of both component strands 112b, 113a are formed, the extension products which may be referred to herein as a "first concatemer strand" 121 and a "second concatemer strand" 122, respectively. The first concatemer strand 121 and the second concatemer strand 122 may be annealed together, and may be collectively referred to as a concatemer 120 (FIG. 1K). The concatemer 120 may contain two or more copies of the nucleic acid template 102. Within the concatemer 120, some or all of the two or more copies of the nucleic acid template 102 may be separated from each other by the sequences of the tail regions of the first primer 105 and second primer 106, where the sequences of the tail regions are annealed to each other. For example, in the concatemer 120 of FIG. 1K, the first copy of the first strand of the double-stranded nucleic acid template is separated from the second copy of the first strand of the double-stranded nucleic acid template by the sequence, in 5'-3' order: CCAT. CCAT is also the sequence, in 5'-3' order, of the tail region of the second primer 106. Similarly, in the concatemer 120 of FIG. 1K, the first copy of the second strand of the double-stranded nucleic acid template is separated from the second copy of the second strand of the double-stranded nucleic acid template by the sequence, in 5'-3' order: ATGG. ATGG is also the sequence, in 5'-3' order, of the tail region of the first primer 105. Within the concatemer, the CCAT of the first concatemer strand is annealed to the ATGG of the second concatemer strand.

In some embodiments, conditions such that a cross-over structure 118 or extension products of the strands of a cross-over structure are formed may include any condition sufficient to support polymerase-based nucleic acid synthesis, including any condition discussed elsewhere herein. The conditions may be the same as used to generate an extension product of the first copy of the first primer 111, an extension product of the second primer 112, or an extension product of the second copy of the first primer 111, or they may be different.

In some embodiments, concatemers provided herein may further increase in length according to the process generally outlined in FIG. 1I-1K. For example, two of the concatemer molecules 120 as shown in FIG. 1K may be treated such that they form a cross-over structure similar to that shown in FIG. 1J (except with longer strands), followed by generation of a larger concatemer molecule containing four copies of the nucleic acid template 102. In another example, a secondary nucleic acid 115 and a concatemer 120 may form a cross-over structure, followed by generation of a larger concatemer molecule containing three copies of the nucleic acid template 102. In some embodiments, in methods provided herein, multiple different concatemers of multiple different lengths may be simultaneously generated.

In embodiments, methods and compositions provided herein may be described with reference to FIG. 8. A polynucleotide template 800 (FIG. 8A) may be a target for amplification. The polynucleotide template 800 is a single nucleotide strand. The polynucleotide template strand may exist as a free, single-stranded molecule, or it may exist as part of a double-stranded molecule, in which the polynucleotide template strand is annealed to a complementary strand thereof. The polynucleotide template 800 may be DNA or RNA.

The polynucleotide template 800 may contain at least a first portion 801 (also indicated with an "(i)") and a second portion 802 (also indicated with an "(ii)"). The first portion 801 and second portion 802 may each contain any number of nucleotides, such as less than 1000, 500, 400, 300, 200, 100, 90, 80, 70, 60, 50, 40, 30, 20, 15, 10, 9, 8, 7, 6, 5, 4, or 3 nucleotides each or at least 1000, 500, 400, 300, 200, 100, 90, 80, 70, 60, 50, 40, 30, 20, 15, 10, 9, 8, 7, 6, 5, 4, or 3 nucleotides each. The first portion 801 and second portion 802 may contain the same or a different number of nucleotides. In some embodiments, the polynucleotide template 800 may contain other portions in addition to the first portion 801 and second portion 802. In other embodiments, the first portion 801 and second portion 802 may constitute the entirety of the polynucleotide template 800. The polynucleotide template 800 may have the length of a nucleic acid template described elsewhere herein. The polynucleotide template 800 may be a portion of a primary nucleic acid. The polynucleotide template may be present in a sample obtained from a subject.

The polynucleotide template 800 may be incubated in a reaction mixture containing a first primer 810 and a second primer 820 (FIG. 8B). Typically, the reaction mixture contains multiple copies of each primer, such as, for example, at least 4, 5, 6, 10, 15, 20, 50, 100, 1000, 10,000, 100,000, or 1 million copies or more of each of the primers. The first primer 810 may have a first region 811 (also indicated with an "(i)") and a second region 812 (also indicated with an "(ii)"). The first region of the first primer 811 may have a 5' end, and the second region of the first primer 812 may have a 3' end. The first region of the first primer may have a nucleotide sequence which is different from the nucleotide sequence of the second region of the first primer. The second primer 820 may have a first region 821 (also indicated with a "(i)") and a second region 822 (also indicated with a "(ii)"). The first region of the second primer 821 may have a 5' end, and the second region of the second primer 822 may have a 3' end. The first region of the second primer may have a nucleotide sequence which is different from the nucleotide sequence of the second region of the second primer.

The second region of the first primer 812 may have a nucleotide sequence which is complementary to the nucleotide sequence of the first portion of the polynucleotide template 801. In FIG. 8, nucleotide sequence of the first portion of the polynucleotide template 801 is represented by the letter A, and the nucleotide sequence of the second region of the first primer 812 is represented by the letter A', where A and A' are complementary to each other. The second region of the second primer 822 may have a nucleotide sequence which is complementary to a partner nucleotide sequence 830, wherein the partner nucleotide sequence 830 is complementary to the nucleotide sequence of the second portion of the polynucleotide template 802. In FIG. 8, the nucleotide sequence of the second portion of the polynucleotide template 802 is represented by the letter B, the nucleotide sequence of the partner nucleotide sequence 830 is represented by the letter B', and the nucleotide sequence of the second region of the second primer 822 is represented by the letter B, where B and B' are complementary to each other. In other words, as indicated by FIG. 8, the nucleotide sequence of the second portion of the polynucleotide template 802 (B) may be the same as the nucleotide sequence of the second region of the second primer 822 (B). With compositions and methods provided herein, a partner nucleotide sequence 830 may be generated, for example, as part of an extension product from the 3' end of the first primer. In embodiments, the first region of the first primer 811 may be complementary to the first region of the second primer 821. In FIG. 8, the nucleotide sequence of the first region of the first primer is represented by the letter C, and the nucleotide sequence of the first region of the second primer is represented by the letter C', where C and C' are complementary to each other.

In embodiments, the first primer and second primer of FIG. 8 may have any of the characteristics of the first primer and second primer described elsewhere herein (e.g. as in FIG. 1), respectively. Also, in embodiments, the first region of the first primer of FIG. 8 may have any of the characteristics of the tail region of a first primer described elsewhere herein. In embodiments, the second region of the first primer of FIG. 8 may have any of the characteristics of the template binding region of a first primer described elsewhere herein. In embodiments, the first region of the second primer of FIG. 8 may have any of the characteristics of the tail region of a second primer described elsewhere herein. In embodiments, the second region of the second primer of FIG. 8 may have any of the characteristics, of the template binding region of a second primer described elsewhere herein.

In embodiments, a reaction mixture containing a polynucleotide template 800 and at least two copies of a first primer 810 and at least two copies of a second primer 820 may contain one or more other components which may support polymerase-based nucleic acid synthesis as described elsewhere herein (e.g. polymerases, nucleotides, buffers, water, etc.). Similarly, a reaction mixture containing a polynucleotide template 800 and at least two copies of a first primer 810 and at least two copies of a second primer 820 may be incubated at any of the reaction conditions described elsewhere herein for supporting the amplification of a nucleic acid template or the generation of concatemers.

In embodiments, upon incubation of a polynucleotide template 800 and at least two copies of a first primer 810 and at least two copies of a second primer 820 in a reaction mixture as described herein, one or more concatemer strands may be formed (FIG. 8C). In embodiments, a formed concatemer strand 840 may have a 5' end and a 3' end, and may have a sequence containing the general structure in the 5' to 3' direction of: C'-T-C'-T-X-C', wherein C' is the nucleotide sequence of the first region of the second primer, T is the sequence of the polynucleotide template or an analogous sequence thereof, and X is any number and sequence of nucleotides. Thus, as indicated by the general structure of the concatemer strand, a concatemer strand may contain at least two copies of the sequence of the polynucleotide template or an analogous sequence thereof, where the copies of the sequence of the polynucleotide template are separated by at least the sequence of the first region of the second primer. In embodiments, T may be an analogous sequence of the polynucleotide template. As used herein, an "analogous sequence" of a polynucleotide template refers to a sequence which contains a similar sequence as the polynucleotide template, but which contains one or more analogous nucleotides to a nucleotide in the polynucleotide template. Thus, for example, if the polynucleotide template contains an RNA sequence, an analogous sequence thereof may be a DNA version of the same sequence (i.e. the uracils in the RNA sequence are thymines in the analogous DNA sequence), or vice-versa. Continuing with the example, if the polynucleotide template contains an RNA sequence of 5' UACCUG 3', an analogous sequence is the DNA sequence of 5' TACCTG 3'.

In embodiments, in a sequence containing the general structure in the 5' to 3' direction of: C'-T-C'-T-X-C', X is zero nucleotides (i.e. the T and C sequence on either side of the X are directly linked). In other embodiments, X is less than 10,000, 5000, 4000, 3000, 2000, 1000, 500, 400, 300, 200, 100, 90, 80, 70, 60, 50, 40, 30, 20, 15, 10, 9, 8, 7, 6, 5, 4, or 3 nucleotides. The nucleotides (if any) in X may have any sequence. In embodiments, X contains a sequence having the general structure in the 5' to 3' direction of $[(C'-T)_N]$ wherein C' is the nucleotide sequence of the first region of the second primer, T is the sequence of the polynucleotide template or analogous sequence thereof, and N is any integer less than 1000, 500, 200, 100, 50, or 10, such as an integer between 1 and 500, 1 and 200, 1 and 100, 1 and 50, or 1 and 10. For example, if "N" is 3 when X contains a sequence having the general structure in the 5' to 3' direction of $[(C'-T)_N]$, there are 3 sequential repeats of (C'-T) in the X position of the structure C'-T-C'-T-X-C', such that the corresponding structure could be written as: C'-T-C'-T-<u>C'-T-C'-T-C'-T</u>-C', where the underlined C's and Ts are the C'-T repeats of the formula $[(C'-T)_3]$. Thus, for example, according to compositions and methods provided herein, concatemer strands may be formed which contain tens or hundreds of copies of the polynucleotide template. In embodiments, a concatemer strand as provided in FIG. 8 may have any of the characteristics of a concatemer strand described elsewhere herein. Also, in some embodiments, during the generation of a concatemer strand, at one or more positions of a C' or T in a sequence having the general structure C'-T-C'-T-X-C', a small number of nucleotides (e.g. 15 or less, 10 or less, 5 or less, or 3 or less) may be inserted between a C' and T. Also, in some embodiments, during the generation of a concatemer strand, at one or more positions of a C' or T in a sequence having the general structure C'-T-C'-T-X-C' or a small number of nucleotides (e.g. 15 or less, 10 or less, 5 or less, or 3 or less) may be deleted from a C' or T sequence. Thus, concatemer strands generated according to methods provided herein may include strands which have a general structure as provided herein, but which may have a small number of nucleotides added or removed at one or more junction points between different sequence components of the concatemer strand (i.e. junctions between template sequence and primer sequence/T and C'). Also, in embodiments, a concatemer strand as provided herein may contain additional nucleotides (e.g. up to 3, 5, 10, 20, 50, 100, 500, 1000 or more additional nucleotides) at the 5' or 3' end of a molecule containing a concatemer having a sequence with the general structure C'-T-C'-T-X-C'. In embodiments, a C' of the general structure C'-T-C'-T-X-C' may have any of the characteristics (e.g. length, sequence) of the tail region of a second primer described elsewhere herein. In embodiments, a T of the general structure C'-T-C'-T-X-C' may have any of the characteristics (e.g. length, sequence) of a polynucleotide template strand described elsewhere herein.

In embodiments, a concatemer strand 840 generated according to method provided herein may be part of a single-stranded molecule. In other embodiments, a concatemer strand 840 generated according to method provided herein may be part of a double-stranded concatemer, in which the concatemer strand 840 is annealed to a strand which is complementary to the concatemer strand 850. While FIG. 8C depicts concatemer strands having a sequence having the general structure in the 5' to 3' direction of: C'-T-C'-T-X-C' (strand 840) or C-T'-C-T'-X'-C (strand 850), wherein X is 0 nucleotides, a concatemer strand generated according to the schematic of FIG. 8 may have any of the characteristics of a concatemer strand described above or elsewhere herein. Also, as relating to FIG. 8C, sequences A and B are part of the template strand, and thus are not separately notated in the general structure C'-T-C'-T-X-C' or C-T'-C-T'-X'-C.

Concatemers generated according to methods and compositions provided herein may be of any length of nucleotides. In some embodiments, concatemer molecules generated herein may be at least 30, 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, 20,000, or 25,000 nucleotides in length. In some embodiments, concatemer molecules generated herein may be no more than 30, 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, 20,000, or 25,000 nucleotides in length. In some embodiments, concatemer molecules generated herein may have a length selected from a range having a minimum value of 30, 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, or 20,000 nucleotides in length, and a maximum value of 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, 20,000, or 25,000 nucleotides in length. In some embodiments, at least some concatemers generated according to a method or composition provided herein have characteristics described above. In some embodiments, at least 10%, 20%, 30%, 40%, 50%, 60%, 70%, 80%, 90%, or 95% of concatemers generated according to a method or composition provided herein have characteristics described above.

Concatemers generated according to methods and compositions provided herein may contain any number of copies of a nucleic acid template or particular nucleic acid. In some embodiments, concatemer molecules generated herein may contain at least 2, 3, 4, 5, 6, 7, 8, 9, 10, 11, 12, 13, 14, 15, 16, 17, 18, 19, 20, 25, 30, 35, 40, 45, 50, 60, 70, 80, 90, or 100 copies of a nucleic acid template or particular nucleic acid. In some embodiments, concatemer molecules generated herein may contain no more than 2, 3, 4, 5, 6, 7, 8, 9, 10, 11, 12, 13, 14, 15, 16, 17, 18, 19, 20, 25, 30, 35, 40, 45, 50, 60, 70, 80, 90, or 100 copies of a nucleic acid template or particular nucleic acid. In some embodiments, concatemer molecules generated herein may have a number of copies of a nucleic acid template or particular nucleic acid selected from a range having a minimum value of 2, 3, 4, 5, 6, 7, 8, 9, 10, 11, 12, 13, 14, 15, 16, 17, 18, 19, 20, 25, 30, 35, 40, 45, 50, 60, 70, 80, or 90 copies, and a maximum value of 3, 4, 5, 6, 7, 8, 9, 10, 11, 12, 13, 14, 15, 16, 17, 18, 19, 20, 25, 30, 35, 40, 45, 50, 60, 70, 80, 90, or 100 copies. In some embodiments, at least some concatemers generated according to a method or composition provided herein have characteristics described above. In some embodiments, at least 10%, 20%, 30%, 40%, 50%, 60%, 70%, 80%, 90%, or 95% of concatemers generated according to a method or composition provided herein have characteristics described above.

Progress of a method provided herein may be monitored in multiple different ways. In embodiments, a reaction may be assayed for a nucleic acid amplification product (e.g. for the amount of the product or the rate of its generation). In other embodiments, a reaction may be assayed for the activity of a polymerase along a nucleic acid template (e.g. for movement of a polymerase along a template strand). Thus, in some embodiments, events of a method provided herein may observed due to the accumulation of product from a method (which may be during or after completion of steps of the method), or due to detectable events occurring during the steps of a method.

The presence of amplified nucleic acids can be assayed, for example, by detection of reaction products (amplified nucleic acids or reaction by-products) or by detection of probes associated with the reaction progress.

In some embodiments, reaction products may be identified by staining the products with a dye. In some embodiments, a dye may have greater fluorescence when bound to a nucleic acid than when not bound to a nucleic acid. In embodiments, a dye may intercalate with a double-stranded nucleic acid or it may bind to an external region of a nucleic acid. Nucleic acid dyes that may be used with methods and compositions provided herein include, for example, cyanine dyes, PicoGreen®, OliGreen®, RiboGreen®, SYBR® dyes, SYBR® Gold, SYBR® Green I, SYBR® Green II, ethidium bromide, dihydroethidium, BlueView™, TOTO® dyes, TO-PRO® dyes, POPO® dyes, YOYO® dyes, BOBO® dyes, JOJO® dyes, LOLO® dyes, SYTOX® dyes, SYTO® dyes, propidium iodide, hexidium iodide, methylene blue, DAPI, acridine orange, quinacrine, acridine dimers, 9-amino-6-chloro-2-methoxyacridine, bisbenzimide dyes, Hoechst dyes, 7-aminoactinomycin D, actinomycin D, hydroxystilbamidine, pyronin Y, Diamond™ dye, GelRed™, GelGreen™ and LDS 751.

In some embodiments, reaction products may be identified by analysis of turbidity of amplification reactions. For example, in embodiments, increased turbidity may be correlated with formation of reaction products and reaction by-products (e.g. pyrophosphate complexed with magnesium).

In some embodiments, reaction products may be identified by separating a reaction performed according to a method herein by gel electrophoresis, followed by staining of the gel with a dye for nucleic acids. The dye may be any nucleic acid dye disclosed herein or otherwise known in the art.

In some embodiments, any method or composition known in the art for the detection of nucleic acids or for the generation of nucleic acids may be used with methods and compositions provided herein.

In some embodiments, a nucleic acid probe which contains a nucleotide sequence complementary to a portion of a nucleic acid template strand (or a strand having a similar or identical sequence) and which contains one or both of a fluorescent reporter (fluorophore) and a quencher are included in a reaction provided herein.

In an example, a nucleic acid probe may contain a fluorescent reporter at its 5' or 3' terminus, and a quencher at the other terminus. The probe may further have a nucleotide sequence containing, in order, at least a first, second, and third region, where the first and third regions are complementary to each other, and where at least a portion of the second region is complementary to a portion of a strand of the nucleic acid template (the probe "detection sequence"). In some embodiments, the length of the second region may be greater than the length of the first or third regions. In some embodiments, the length of the second region may be between 10 and 40 nucleotides, and the length of first and third regions may be between 4 and 10 nucleotides. The probe may have at least two different conformations: (A) a conformation where the probe is not annealed to its detection sequence and where the first and third regions are annealed to each other; this conformation may be a "stem-loop" structure, where the first and third regions form the stem and the second region forms the loop, and (B) a conformation where the probe is annealed to its detection sequence; in this conformation, the second region or a portion thereof is annealed to its detection sequence and the first and third regions are not annealed to each other. In conformation (A) of the probe, the fluorescent reporter and quencher (which are located at opposite termini of the probe/at the outer ends of the first and third regions) may be in close proximity to each other (both being at the end of the stem structure formed by the annealing of the first and third regions), such that the fluorescent reporter is quenched. In conformation (B) of the probe, the fluorescent reporter and quencher may not be in close proximity to each other, such that the fluorescent reporter is not quenched. The probe may be used to monitor accumulation of a selected reaction product, for example, under reaction conditions where the probe may either form a stem-loop structure or anneal to its detection sequence. In some embodiments, if the detection sequence is present, the probe may anneal to the detection sequence, and the probe may fluoresce in response to light of a wavelength of the fluorophore's excitation spectrum. In contrast, if the detection sequence is not present, the probe may form a stem-loop structure, and not fluoresce in response to light of a wavelength of the fluorophore's excitation spectrum.

In another example, a nucleic acid probe may contain a fluorescent reporter at its 5' or 3' terminus, and it may be annealed to a nucleic acid primer containing a quencher. The nucleic acid primer containing a quencher may contain the quencher at a position in the primer such that when the nucleic acid probe is annealed to the primer, the fluorescent reporter is quenched. The probe may, be used to monitor accumulation of a selected reaction product, for example, under reaction conditions where the probe may either anneal to the primer or anneal to its detection sequence in the reaction product. In some embodiments, if the detection sequence is present, the probe may anneal to the detection sequence, and the probe may fluoresce in response to light of a wavelength of the fluorophore's excitation spectrum (thus indicating the presence of the reaction product). In contrast, if the detection sequence is not present, the probe may remain paired with the primer, and not fluoresce in response to light of a wavelength of the fluorophore's excitation spectrum.

In probes containing a fluorescent reporter and quencher pair, the fluorescent reporter and quencher may be selected so that the quencher can effectively quench the reporter. In some embodiments, a fluorescent reporter is paired with a quencher where the emission maximum of the fluorescent reporter is similar to the absorption maximum of the quencher. Fluorophores that may be used as the fluorescent reporter include, for example, CAL Fluor Gold, CAL Fluor Orange, Quasar 570, CAL Fluor Red 590, CAL Fluor Red 610, CAL Fluor Red 610, CAL Fluor Red 635, Quasar 670 (Biosearch Technologies), VIC, NED (Life Technologies), Cy3, Cy5, Cy5.5 (GE Healthcare Life Sciences), Oyster 556, Oyster 645 (Integrated DNA Technologies), LC red 610, LC red 610, LC red 640, LC red 670, LC red 705 (Roche Applies Science), Texas red, FAM, TET, HEX, JOE, TMR, and ROX. Quenchers that may be used include, for example, DDQ-I, DDQ-II (Eurogentec), Eclipse (Epoch Biosciences), Iowa Black FQ, Iowa Black RQ (Integrated DNA Technologies), BHQ-1, BHQ-2, BHQ-3 (Biosearch Technologies), QSY-7, QSY-21 (Molecular Probes), and Dabcyl.

In some embodiments, a reaction performed according to a method provided herein may be monitored in an apparatus containing a light source and an optical sensor. In some situations, the reaction may be positioned in the path of light from the light source, and light absorbed by the sample (e.g. in the case of a turbid reaction), scattered by the sample (e.g. in the case of a turbid reaction), or emitted by the sample (e.g. in the case of a reaction containing a fluorescent molecule) may be measured. In some embodiments, a method provided herein may be performed or monitored in a device or module therein as disclosed in U.S. patent application Ser. No. 13/769,779, filed Feb. 18, 2013, which is herein incorporated by reference in its entirety.

Using methods provided herein, specific amplification products of a nucleic acid template of interest may be identified within, for example, 30 seconds, 1 minute, 3 minutes, 5 minutes, 10 minutes, 15 minutes, 20 minutes, 30 minutes, 45 minutes, 60 minutes, 90 minutes, 120 minutes, 180 minutes, or 240 minutes of initiation of an amplification reaction. In other examples, using methods provided herein, amplification reactions which are positive for a nucleic acid template of interest may be identified when as few as 10, 50, 100, 500, 1000, 5000, 10,000, 50,000, 100,000, 500,000, or 1,000,000 copies of the template are generated. In other examples, using methods provided herein, the presence of a nucleic acid template of interest in a sample containing as few as 1, 2, 3, 4, 5, 10, 15, 20, 25, 30, 40, 50, 100, 200, 500, 1000, 5000, or 10,000 copies of the template of interest at the start of the method may be identified.

In embodiments, methods provided herein may be used to assay a sample for a target nucleic acid of interest. In certain embodiments, the presence or quantity of a target nucleic acid of interest in a sample may be determined by a method involving determining an inflection time for nucleic acid amplification in a reaction. An inflection time/inflection point is a time or a point where an amplification reaction is determined as being positive for a nucleic acid template. An inflection time/point may be identified by one or more indicators, such as for example, the time post-initiation of a reaction when a selected quantity of nucleic acid has been generated in the reaction, the time when the rate of amplification in a reaction changes from a baseline phase to an exponential phase, or the time when the rate of amplification in a reaction changes from an exponential phase to a plateau phase, etc. In embodiments, an inflection time/point may be identified based on a change in fluorescence or absorbance of a reaction, or upon the fluorescence or absorbance of a reaction reaching a selected value. In certain embodiments, the presence or quantity of a target nucleic acid of interest in a sample may be determined by a method involving comparison of an inflection time for nucleic acid amplification of a reaction of which has an unknown amount of target nucleic acid of interest versus one or both of: i) a reaction which is known to lack the target nucleic acid of interest (i.e. a negative control) or ii) a reaction which is known to contain the target nucleic acid of interest (i.e. a positive control). In embodiments, both a reaction which contains the target nucleic acid of interest and a reaction which does not contain the target nucleic acid may be measured for a selected inflection time. In embodiments, the presence of a target nucleic acid of interest in a sample may be determined based on a method which involves evaluation of the difference in time between inflection of a reaction containing a sample which may or may not contain a target nucleic acid of interest, and a time of inflection of one or more reactions with known target nucleic acid of interest status (e.g. which are known to contain or not contain the target nucleic acid of interest). For example, a sample may be identified as containing a target nucleic acid of interest if the inflection time of the reaction according to a method provided herein is at least 3, 5, 10, 15, 20, 30, 40, 50, 60, 90, 120, or 180 minutes earlier than a corresponding reaction which is known to not contain the target nucleic acid of interest. In another example, a sample may be identified as containing a target nucleic acid of interest if the inflection time of the reaction according to a method provided herein is no more than 3, 5, 10, 15, 20, 30, 40, 50, 60, 90, 120, or 180 minutes later than a corresponding reaction which is known to contain the target nucleic acid of interest.

Methods provided herein may be performed for any length of time. Typically, the method will be performed for a length of time sufficient to monitor, for example, the rate of nucleic acid replication, the occurrence of polymerase activity, or the accumulation of amplification product. In some embodiments, a method provided herein may be performed for a total of less than 10 seconds, 30 seconds, 1 minute, 5 minutes, 10 minutes, 20 minutes, 30 minutes, 45 minutes, 1 hour, 2 hours, 3 hours, 4 hours, 6 hours, 8 hours, 12 hours, 16 hours, or 24 hours, by which time the rate of nucleic acid replication, the occurrence of polymerase activity, or the accumulation of amplification product is measured.

Methods provided herein may be terminated in various ways. In one embodiment, steps of a method may end upon the reduction in concentration or complete consumption of one or more reagents involved in one or more steps of the method (e.g. dNTPs). In another embodiment, steps of a method may end upon inactivation of one or more enzymes involved in one or more steps of the method (e.g. polymerases). Enzymes may be inactivated by various ways. For example, enzymes may gradually lose enzymatic activity over time due to random events that affect the structure of the enzyme, or enzymes may be exposed to a condition to accelerate the inactivation of the enzyme activity (e.g. high heat, extreme pH, etc.).

In some embodiments, a primary nucleic acid may be single stranded or double-stranded. A single stranded primary nucleic acid may also be referred to herein as a "primary polynucleotide". A primary nucleic acid may be linear or circular. A primary nucleic acid may comprise a nucleic acid template. In some embodiments, the entirety of a primary nucleic acid may be a nucleic acid template. In other embodiments, a primary nucleic acid may contain one or more nucleotides which are not part of a nucleic acid template (e.g. the primary nucleic acid may be of a greater length than a nucleic acid template contained within the primary nucleic acid). In some embodiments, a primary nucleic acid may contain two or more copies of a nucleic acid template. A primary nucleic acid may contain DNA, RNA, or a mixture thereof. A double-stranded linear primary nucleic acid may have blunt ends or sticky ends ("sticky ends" refer to ends having an overhanging strand having one or more unpaired nucleotides).

A primary nucleic acid may be of any length of nucleotides. For example, a primary nucleic acid may be at least 2, 3, 4, 5, 6, 7, 8, 9, 10, 12, 14, 16, 18, 20, 25, 30, 35, 40, 45, 50, 60, 70, 80, 90, 100, 150, 200, 250, 300, 350, 400, 500, 750, 1000, or 1500 nucleotides in length. In another example, a primary nucleic acid may be between 2 and 100,000, between 5 and 100,000, between 10 and 100,000, between 15 and 100,000, between 20 and 100,000, between 25 and 100,000, between 30 and 100,000, between 50 and 100,000, between 70 and 100,000, between 100 and 100,000, between 200 and 100,000, between 2 and 10,000, between 5 and 10,000, between 10 and 10,000, between 15 and 10,000, between 20 and 10,000, between 25 and 10,000, between 30 and 10,000, between 50 and 10,000, between 70 and 10,000, between 100 and 10,000, between 200 and 10,000, between 2 and 5,000, between 5 and 5,000, between 10 and 5,000, between 15 and 5,000, between 20 and 5,000, between 25 and 5,000, between 30 and 5,000, between 50 and 5,000, between 70 and 5,000, between 100 and 5,000, between 200 and 5,000, between 2 and 3,000, between 5 and 3,000, between 10 and 3,000, between 15 and 3,000, between 20 and 3,000, between 25 and 3,000, between 30 and 3,000, between 50 and 3,000, between 70 and 3,000, between 100 and 3,000, between 200 and 3,000, between 2 and 1,000, between 5 and 1,000, between 10 and 1,000, between 15 and 1,000, between 20 and 1,000, between 25 and 1,000, between 30 and 1,000, between 50 and 1,000, between 70 and 1,000, between 100 and 1,000, between 200 and 1,000, between 2 and 500, between 5 and 500, between 10 and 500, between 15 and 500, between 20 and 500, between 25 and 500, between 30 and 500, between 50 and 500, between 70 and 500, between 100 and 500, or between 200 and 500 nucleotide bases in length.

In some embodiments, a nucleic acid template may be single stranded or double-stranded. A single strand of a nucleic acid template may be referred to herein as a "polynucleotide template". A "polynucleotide template" as referred to herein is not precluded from binding to a complementary sequence thereof. In other words, a "polynucleotide template" may be, for example, the entirety of a single-stranded nucleic acid template, or it may be one strand of a double-stranded nucleic acid template. A nucleic acid template may be contained in a primary nucleic acid molecule. In some embodiments, a nucleic acid template may constitute the entirety of a primary nucleic acid molecule. In other embodiments, a nucleic acid template may be contained in a primary nucleic acid which contains one or more nucleotides which are not part of the nucleic acid template (e.g. the nucleic acid template may be of a shorter length than the primary nucleic acid which contains the nucleic acid template).

A nucleic acid template may be of any length of nucleotides. For example, a nucleic acid template may be at least 2, 3, 4, 5, 6, 7, 8, 9, 10, 12, 14, 16, 18, 20, 25, 30, 35, 40, 45, 50, 60, 70, 80, 90, 100, 150, 200, 250, 300, 350, 400, 500, 750, 1000, or 1500 nucleotides in length. In another example, a nucleic acid template may be between 2 and 100,000, between 5 and 100,000, between 10 and 100,000, between 15 and 100,000, between 20 and 100,000, between 25 and 100,000, between 30 and 100,000, between 50 and 100,000, between 70 and 100,000, between 100 and 100,000, between 200 and 100,000, between 2 and 10,000, between 5 and 10,000, between 10 and 10,000, between 15 and 10,000, between 20 and 10,000, between 25 and 10,000, between 30 and 10,000, between 50 and 10,000, between 70 and 10,000, between 100 and 10,000, between 200 and 10,000, between 2 and 5,000, between 5 and 5,000, between 10 and 5,000, between 15 and 5,000, between 20 and 5,000, between 25 and 5,000, between 30 and 5,000, between 50 and 5,000, between 70 and 5,000, between 100 and 5,000, between 200 and 5,000, between 2 and 3,000, between 5 and 3,000, between 10 and 3,000, between 15 and 3,000, between 20 and 3,000, between 25 and 3,000, between 30 and 3,000, between 50 and 3,000, between 70 and 3,000, between 100 and 3,000, between 200 and 3,000, between 2 and 1,000, between 5 and 1,000, between 10 and 1,000, between 15 and 1,000, between 20 and 1,000, between 25 and 1,000, between 30 and 1,000, between 50 and 1,000, between 70 and 1,000, between 100 and 1,000, between 200 and 1,000, between 2 and 500, between 5 and 500, between 10 and 500, between 15 and 500, between 20 and 500, between 25 and 500, between 30 and 500, between 50 and 500, between 70 and 500, between 100 and 500, or between 200 and 500 nucleotide bases in length.

A "primer" as used herein may refer to a polynucleotide which is i) capable of hybridizing to an original nucleic acid strand and ii) acting as a point of initiation for the synthesis of a new nucleic acid strand, wherein the new nucleic acid strand is an extension product of the primer and is complementary to the original strand. A primer may have a free —OH group at its 3' terminus, which may serve as the origin of synthesis for the extension product.

A primer may contain standard nucleotides [e.g. standard DNA deoxyribonucleotides (deoxyadenosine monophosphate, deoxyguanosine monophosphate, thymidine monophosphate, deoxycytidine monophosphate) or standard RNA ribonucleotides (adenosine monophosphate, guanosine monophosphate, uridine monophosphate, cytidine monophosphate)], alternative nucleotides (e.g. inosine), modified nucleotides, nucleotide analogs, or a combination thereof. For example, an oligonucleotide primer may include peptide nucleic acids, morpholinos (e.g. phosphorodiamidate morpholino oligos), locked nucleic acids [see, for example, Kaur, H, et. al, Biochemistry 45 (23), 7347-55 (2006)], glycol nucleic acids, or threose nucleic acids. A primer may have a backbone, including, for example, phosphodiester linkages, phosphorothioate linkages (a non-bridging O is replaced with sulfur), or peptide linkages (as part of a peptide nucleic acid). Alternative nucleotides, modified nucleotides, and nucleotide analogs may be referred to collectively herein as "non-standard nucleotides."

The presence of a non-standard nucleotide in a primer may affect various properties of the primer. In some embodiments, inclusion of a non-standard nucleotide in a primer may increase or decrease the thermodynamic stability of a primer to a complementary sequence thereof. For example, a primer having increased thermodynamic stability may contain a locked nucleic acid. A primer having decreased thermodynamic stability may contain, for example, inosine (described by Auer et al., Nucl. Acids Res. 24; 5021-5025 (1996)) or a negatively charged chemical group, such as a carboxylic acid.

A first primer or a second primer provided herein may be of any length. The first primer and second primer may contain the same number of nucleotides, or a different number of nucleotides. In some embodiments, a first or second primer may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length. In some embodiments, a first or second primer may be no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length. In some embodiments, a first or second primer may have a length selected from a range having a minimum value of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, or 1000 nucleotides in length, and a maximum value of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length.

The tail region of a first primer or a second primer provided herein may be of any length. Typically, the tail regions of a first primer and a second primer directed to the same template contain the same number of nucleotides. In some embodiments, the tail region of a first or second primer may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length. In some embodiments, the tail region of a first or second primer may be no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length. In some embodiments, the tail region of a first or second primer may have a length selected from a range having a minimum value of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, or 1000 nucleotides in length, and a maximum value of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length.

The template-binding region of a first primer or a second primer provided herein may be of any length. The template-binding regions of a first primer and a second primer directed to the same template may contain the same number of nucleotides, or a different number of nucleotides. In some embodiments, the template-binding region of a first or second primer may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length. In some embodiments, the template-binding region of a first or second primer may be no more than 2, 3, 4, 5, 6, 7, 8, 9, 10, 11, 12, 13, 14, 15, 16, 17, 18, 19, 20, 21; 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length. In some embodiments, the template-binding region of a first or second primer may have a length selected from a range having a minimum value of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, or 1000 nucleotides in length, and a maximum value of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length.

In some embodiments, a primer may be of any length and contain any nucleotide sequence which permits sufficiently stable and specific annealing of the primer to its complement at the temperature being used for a method or step thereof involving the primer. The exact length desired of a primer may depend on a variety of factors, including the temperature of a reaction, the chemical composition of the primer, and the reaction involving the primer. In some embodiments, the template-binding region of a primer may be of any length and contain any nucleotide sequence which permits sufficiently stable and specific annealing of the template-binding region of the primer to its complement at the temperature being used for a method or step thereof involving the primer. The exact length desired of the template-binding region of a primer may depend on a variety of factors, including the temperature of a reaction, the chemical composition of the template-binding region of the primer, and the reaction involving the primer. The inclusion of one or more non-standard nucleotides in the primer may change the desired length of the primer for use in a method provided herein, as compared to the length of a corresponding primer lacking a non-standard nucleotide. For example, if with a method provided herein it is desired to have a primer with a certain melting temperature ("Tm"), in some embodiments, a primer with the selected Tm may be of a shorter length if the primer contains at least some non-standard nucleotides, as compared to if the primer contains only standard nucleotides. Generally, "melting temperature" of a nucleotide sequence refers to the temperature at which 50% of nucleic acids having the nucleotide sequence are based paired to a complementary sequence thereof (i.e. are in a double-stranded molecule), and 50% of nucleic acids having the nucleotide sequence are in single-stranded form.

A primer provided herein may be prepared by any suitable method. For example, a primer may be chemically synthesized. In another example, a naturally occurring nucleic acid may be isolated, cleaved (e.g. with restriction enzymes), and/or modified to generate or to become part of a primer described herein.

In some embodiments, a label may be attached to a primer. Labels include, for example, binding ligands (e.g. digoxin or biotin), enzymes, fluorescent molecules/fluorophores, luminescent molecules, quencher molecules, or radioisotopes. In other embodiments, a base of an oligonucleotide may be replaced with a fluorescent analog, such as 2-aminopurine (see, for example, Proc. Acad. Sci. USA, 91, 6644-6648 (1994), which is herein incorporated by reference in its entirety).

In some embodiments, conditions such that: i) a template-binding region of a first copy of a first primer anneals to a strand of a nucleic acid template, ii) a template-binding region of a second primer anneals to an extension product of a first copy of a first primer, iii) a template-binding region of a second copy of a first primer anneals to an extension product of a second primer, or iv) a 3' terminal region of an extension product of a second copy of a first primer of a first copy of a secondary nucleic acid anneals to a 3' terminal region of an extension product of a second primer of a second copy of a secondary nucleic acid, to produce a cross-over structure comprising these strands, may each include (i.e. any of i), ii), iii), or iv) may include) incubating the nucleic acids at a temperature such that the strands of double-stranded nucleic acid molecules "breathe" (i.e. undergo brief periods of localized rupture of hydrogen bonds connecting base pairs) to a degree sufficient to facilitate the entry of a primer or different nucleic acid strand between the strands of a double-stranded molecule, and sufficient to permit the annealing of the primer or different nucleic acid strand to one of the strands of the opened double-stranded nucleic acid molecule. In some embodiments, methods or steps thereof may be performed or incubated at a temperature of at least 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, or 95 C. In some embodiments, methods or steps thereof may be performed or incubated at a temperature of no greater than 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, or 95 C. In some embodiments, methods or steps thereof may be performed or incubated at a temperature between 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, or 90 C and 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90 or 95 C.

In some embodiments, for a method or steps thereof provided herein, the step or method is performed at a temperature below the melting temperature (Tm) of the relevant potentially paired nucleotide strands, or regions thereof (e.g. the template-binding region of the first primer to the first strand of a nucleic acid template, the template-binding region of the second primer to the extension product of the first copy of the first primer, the first primer to the extension product of the second primer, the 3' terminal region of the extension product of the second primer to its complement, the 3' terminal region of the extension product of the first copy of the first primer to its complement, etc.). In some embodiments, for a method or steps thereof provided herein, the step or method is performed at a temperature above the Tm of the relevant potentially paired nucleotide strands, or regions thereof (e.g. the template-binding region of the first primer to the first strand of a nucleic acid template, the template-binding region of the second primer to the extension product of the first copy of the first primer, the first primer to the extension product of the second primer, the 3' terminal region of the extension product of the second primer to its complement, the 3' terminal region of the extension product of the first copy of the first primer to its complement, etc.). In some embodiments, for a method or steps thereof provided herein, the step or method is performed at a temperature at or within +/− 1, 2, 3, 4, 5, 6, 7, 8, 9, 10, 11, 12; 13, 14, 15, 20, or 25 C of the Tm of the relevant potentially paired nucleotide strands, or regions thereof (e.g. the template-binding region of the first primer to the first strand of a nucleic acid template, the template-binding region of the second primer to the extension product of the first copy of the first primer, the first primer to the extension product of the second primer, the 3' terminal region of the extension product of the second primer to its complement, the 3' terminal region of the extension product of the first copy of the first primer to its complement, etc.).

In some embodiments, a nucleic acid polymerase is included with a method or composition provided herein. A polymerase may generate an extension product of a primer. The primer and extension product thereof may be complementary to a template nucleic acid strand. Generally, a nucleic acid polymerase will initiate synthesis of an extension product of a primer at the 3' end of the primer. In some embodiments, a DNA polymerase is included with a method or composition provided herein. As used herein, a "DNA polymerase" refers to a nucleic acid polymerase which has primary or exclusive polymerase activity on DNA templates. In some embodiments, a reverse transcriptase is included with a method or composition provided herein. As used herein, a "reverse transcriptase" refers to a nucleic acid polymerase which can synthesize a DNA strand from an RNA template. In some embodiments, an RNA polymerase may be included with a method or composition provided herein. As used herein, a "RNA polymerase" refers to a nucleic acid polymerase which can synthesize an RNA strand from a DNA or RNA template.

In some embodiments, a polymerase provided herein may have strand displacement activity. Polymerases having strand displacement activity include, for example, exo-Bca DNA polymerase, phi29 DNA polymerase, Klenow Fragment of E. coli DNA Polymerase I, Vent$_R$ DNA polymerase, Deep Vent$_R$ DNA polymerase, 9° N$_m$ DNA polymerase, Bst 2.0 DNA polymerase, and Large Fragment of Bst DNA Polymerase. Other polymerases having strand displacement activity may also be used.

Modified versions of polymerases may also be used with the methods and compositions provided herein, provided that the modified polymerase has sequence-dependent nucleic acid synthesis activity. A modified version of a polymerase ("modified polymerase") may have, for example, 100 or fewer, 70 or fewer, 50 or fewer, 40 or fewer, 30 or fewer, 20 or fewer, 10 or fewer, 5 or fewer, 4 or fewer, 3 or fewer, 2 or fewer, or 1 different amino acid from the sequence of the parent version of the polymerase. In some embodiments, a modified polymerase may contain no more than 1000, 700, 500, 400, 300, 200, 100, 50, 40, 30, 20, 10, or 5 greater or fewer amino acids than the parent polymerase. In some embodiments, a modified polymerase may comprise a fragment of a parent polymerase. In some embodiments, a modified polymerase may comprise a chimeric polypeptide with a portion derived from a polymerase and a portion derived from a non-polymerase protein. In some embodiments, a modified polymerase may have, for example, increased catalytic activity, increased stability, or increased thermostability as compared to the parent polymerase.

In some embodiments, a polymerase provided herein is thermostable. A thermostable polymerase may have, for example, a half-life of at least 5, 10, 15, 20, 30, 40, 50, 60, 90, 120, or 180 minutes at a temperature of up to 25, 30, 35 40, 45, 50, 55, 60, 65, 70, 75, 80, 85, 90, or 95 C. In some embodiments, a modified polymerase may be thermostable.

In some embodiments, methods and steps thereof provided herein include or are performed under conditions sufficient to support polymerase-based nucleic acid synthesis. Example conditions for polymerase-based nucleic acid synthesis are known in the art and are provided, for example, in Green and Sambrook, supra. Non-limiting components for a polymerase-based nucleic acid synthesis reaction may include one or more of: polymerase enzyme (at a concentration between, for example, 0.01 and 10 units enzyme per 50 microliters reaction volume, or any range therein including, for example, between 0.01-1, 0.1-10, 0.1-5, 0.5-10, 0.5-5, 0.5-2, 1-10, or 1-5 units enzyme per 50 microliters reaction volume, where 1 unit of enzyme will incorporate 15 nmol of dNTPs into polymerization product in 30 minutes at 75 C); template (at a concentration of at least, for example, 1, 10, 100, 1,000, 10,000, or 100,000 copies per reaction); primer (at a concentration between, for example, 0.01 and 10 micromolar, or any range therein including, for example, between 0.01-1, 0.1-10, 0.1-5, 0.5-5, or 0.5-2 micromolar); dNTPs (e.g. dATP, dTTP, dGTP, and dCTP, at a concentration between, for example, 50 and 500 micromolar each of dATP, dTTP, dGTP, and dCTP, or any range therein including, for example, between 50-350, 100-500, 100-300, 200-500, or 300-400 micromolar each of dATP, dTTP, dGTP, and dCTP); salt (e.g. KCl or potassium acetate, at a concentration between, for example, 1 and 200 millimolar, or any range therein including, for example, between 1-100, 1-50, 1-20, 1-10, 10-20, 10-50, or 10-200 millimolar); buffer (e.g. Tris-HCl or Tris-acetate, pH 7.8-8.5, at a concentration between, for example, 1 and 100 millimolar, or any range therein including, for example, between 1-50, 1-20, 1-10, 1-5, 10-100, 20-100, or 50-100 millimolar); and magnesium ions (at a concentration between, for example 0.1 and 10 millimolar, or any range therein, including, for example, between 0.1-5, 0.1-1, 0.5-10, 0.5-5, or 0.5-2.5 millimolar). Additional non-limiting components for a polymerase-based nucleic acid synthesis reaction may increase the speed of the reaction, increase the fidelity of the reaction, or increase the stability of enzymes or DNA in the reaction, and may include one or more of gelatin (at a concentration between, for example, 0.0001% and 0.1% w/v), BSA (at a concentration between, for example, 0.01 and 1 microgram per microliter), sucrose (at a concentration between, for example 0.01 molar and 0.8 molar), trehalose (at a concentration between, for example 0.01 molar and 0.8 molar), DMSO (at a concentration between, for example, 0.01 and 10% v/v), betaine (at a concentration between, for example, 0.1 and 10 molar), formamide (at a concentration between, for example, 0.1 and 10% v/v), glycerol (at a concentration between, for example, 0.1 and 20% v/v), polyethylene glycol (at a concentration between, for example, 0.1 and 20% v/v), non-ionic detergents [e.g. NP-40 (at a concentration between, for example, 0.01 and 1% v/v), Tween-20 (at a concentration between, for example, 0.01 and 1% v/v), or Triton X-100 (at a concentration between, for example, 0.01 and 1% v/v)], ammonium ions [e.g. ammonium sulfate (at a concentration between, for example, 1 and 100 millimolar)], and EDTA (at a concentration between, for example, 0.001 and 0.1 millimolar). Other reagents may also be present in a polymerase-based nucleic acid synthesis reaction provided herein. For example, reagents sufficient to synthesize RNA reaction products or reaction products containing non-standard nucleotides may be used. Conditions sufficient to support polymerase-based nucleic acid synthesis may include a variety of temperatures and pH values. For example, the pH of a polymerase-based nucleic acid synthesis reaction may be between, for example pH 6.0 and pH 10.0, such as 6.5, 7, 7.5, 7.8, 7.9, 8, 8.1, 8.2, 8.5, 9, or 9.5. The temperature of a polymerase-based nucleic acid synthesis reaction may be constant or varied. A constant temperature may be between, for example, 10 C and 95 C, such as 20, 25, 30, 35, 37, 40, 42, 45, 50, 55, 60, 65, 70, 75, 80, or 85 C. A varied temperature may be two or more different temperatures between, for example, 10 C and 95 C, such as two or more temperatures selected from 20, 25, 30, 35, 37, 40, 42, 45, 50, 55, 60, 65, 70, 75, 80, or 85 C.

Methods provided herein may be performed at a variety of temperatures. In some embodiments, all steps of a method are performed at the same temperature. Thus, temperature cycling such as in PCR is not necessary with methods disclosed herein. In some embodiments, methods provided herein may be performed at two or more different temperatures. In some embodiments, a reaction mixture containing reagents for a method provided herein is incubated at two or more different temperatures. In some examples, different temperatures may be selected to optimize the rate, accuracy, or other feature of different steps of a method provided herein. For example, a temperature may be selected to increase the enzymatic activity of a polymerase. In some examples, different temperatures may be selected to increase the binding specificity of a primer to a template or to increase the accessibility of a template to a primer (e.g. higher temperatures may promote the separation of duplex template nucleic acids). In some embodiments, all of the steps of a method provided herein are performed at a temperature of no greater than 80, 70, 60, 50, 40, 30, 20 or 10° C. In some embodiments, a method provided herein is performed at a temperature between 20-60, 30-70, 40-80, 20-40, 30-50, 40-60, 50-70, 60-80, 30-40, 35-45, 40-50, 45-55, 50-60, 55-65° C. In certain embodiments, a sample containing a target nucleic acid may be heated to a temperature greater than 40, 50, 60, 70, 80, 90, or 95 C before the initiation of a method provided herein. In certain embodiments, a reaction mixture provided herein may be heated one time to an elevated temperature greater than 40, 50, 60, 70, 75, 80, 85, 90, or 95 C before or after the initiation of a method provided herein. After heating the reaction mixture to the elevated temperature, it may be maintained at a lower temperature as provided elsewhere herein (e.g. at a temperature between 40-70 C) for the remainder of the performance of the method. In embodiments, if a reaction mixture or sample is heated to an elevated temperature before the initiation of a method provided herein, a nucleic acid polymerase may be added to the reaction mixture or sample after the reaction mixture or sample has been heated to the elevated temperature, and the reaction mixture or sample has been returned to a lower temperature as provided herein. Methods disclosed herein may be performed with or without a thermocycler.

As one consideration, the temperature used for a method or step thereof provided herein may be selected to be appropriate for the enzyme(s) being used in the step of the method. In some embodiments, for methods in which a polymerase is used, the temperature(s) of the reaction is selected such that it does not significantly impair the activity of the polymerase (e.g. the temperature of the reaction may be selected such that polymerase has a half-life of at least 24, 12, 6, 4, 3, 2, 1, 0.75, 0.5, 0.25, or 0.1 hours). Alternatively, methods may be performed at a temperature that impairs the activity of the enzyme(s) being used in the method (e.g. the temperature of the reaction may be selected such that an enzyme in the reaction has a half-life of no more than 24, 12, 6, 4, 3, 2, 1, 0.75, 0.5, 0.25, or 0.1 hours). In some embodiments, if a method is performed at a temperature or other condition (e.g. pH) that impairs the activity of one or more enzyme(s), additional enzyme may be added to the reaction at one or more intervals after the initiation of the method to supplement the activity of the impaired enzyme(s).

In some embodiments, one or more steps of a method provided herein occur in the same reaction vessel (e.g. tube, tip, container, etc.). In some embodiments, all of the steps of a method occur in the same reaction vessel.

Reagents for methods provided herein can all be provided together at the start of a reaction, or they may be added sequentially, where after one, two, or more steps new reagents are added to a reaction. In some circumstances, new reagents (e.g. enzymes, primers) may be added to a reaction vessel during the course of the reaction, to increase the amount of reagents available to act on substrates or to replace the function of reagents that have become inactivated (e.g. enzymes). New reagents may be added to a reaction at one or more selected time intervals after the initiation of a reaction of a method provided herein (for example, at 1, 3, 5, 7, 10, 15, 20, 30, 45, or 60 minutes after the initiation of a reaction).

In some embodiments, one or more steps of a method provided herein may occur simultaneously. For example, after the generation of a single copy of an extension product of a first copy of the first primer, multiple copies of an extension product of a second primer may be sequentially generated from that single copy of an extension product of a first copy of the first primer. As copies of the extension product of a second primer are sequentially generated from the single copy of the extension product of a first copy of the first primer, the individual copies of the extension product of a second primer may, for example, serve as a template for the formation of an extension product of a second copy of the first primer, be a component of a secondary nucleic acid, be a component of a cross-over structure, or may be an initiation point for the formation of an extension product of an extension product of a second primer/first concatemer strand. In another example, two copies of a secondary nucleic acid may form a cross-over structure at the same time that an extension product of a first copy of a first primer is generated from a first strand of a nucleic acid template. In another example, one copy of an extension product of a first copy of a first primer is generated from a first strand of a nucleic acid template at the same time that an extension product of the second primer is generated from a different copy of the extension product of a first copy of a first primer. Other steps provided herein may also occur simultaneously. In addition, in methods and compositions provided herein involving a double-stranded nucleic acid template, either strand of the nucleic acid template may be considered a "first strand", and either primer of a primer pair provided herein may be considered a "first primer". Accordingly, in some examples, both strands of a double-stranded nucleic acid may be simultaneously used as "first strand" of a nucleic acid according to a method provided herein, with opposite primers of the primer pair serving as the "first primer" for the different "first strands". Also, various structures generated according to methods provided herein may optionally enter different pathways of methods provided herein. For example, in embodiments, a first secondary nucleic acid may pair with a second secondary nucleic acid to form a cross-over structure as described elsewhere herein. In other embodiments, a first secondary nucleic acid may be invaded by a first primer, and the extension product of the second primer may serve as a template for the generation of a new extension product of the first primer. In order to generate the new extension product of the first primer, the extension product of the first primer which is part of the secondary nucleic acid is displaced. In another example, in embodiments, a first concatemer may pair with another concatemer to form a cross-over structure. In other embodiments, a first concatemer may be invaded by a first primer, and the first concatemer strand may serve as a template for the generation of a new second concatemer strand. In order to generate the new first concatemer strand, the first concatemer strand which is part of the concatemer is displaced. Other similar events may also occur during methods provided herein.

Reactions and compositions provided herein may contain multiple copies of first primers, second primers, primary nucleic acids, secondary nucleic acids, extension products of a first copy of the first primer, extension products of a second copy of the first primer, extension products of the second primer, cross-over structures, concatemers, and the like. Accordingly, methods provided herein may include processes wherein multiple steps provided herein occur simultaneously, and such steps may occur with multiple copies of the relevant molecules.

In some embodiments, two or more sets of first and second primers are provided in a method or composition provided herein, where each set contains a first primer and a second primer, and where different primer sets are complementary to different nucleic acid templates. The template-binding region of both the first and second primers in a set may be complementary to different strands of the same double-stranded nucleic acid template. Typically, the tail regions of the first and second primers in a given set have different, non-complementary sequences from the tail regions of the first and second primer of other primer sets to be used in the same method or composition, so that the primer tails from the different primer sets are not complementary. This may be desirable in order to prevent the formation of hybrid cross-over structures containing strands derived from different nucleic acid templates. Alternatively, tail regions of the first and second primers in two or more different primer sets may have complementary sequences, in order to create hybrid cross-over structures and concatemers containing strands derived from different nucleic acid templates. Inclusion of two or more primer sets in a method or composition provided herein may support the simultaneous amplification of multiple different nucleic acid templates in the same reaction vessel. This may be useful, for example, for amplifying multiple templates of interest in a sample, or for assaying for the presence of multiple different templates in a sample. In some embodiments, 1, 2, 3, 4, 5, 6, 7, 8, 9, 10, 15, 20, 25, 30, 40, 50, 60, 70, 100, 200, 500 or more sets of first and second primers are provided in a method provided herein, in order to amplify or assay for the presence of 1, 2, 3, 4, 5, 6, 7, 8, 9, 10, 15, 20, 25, 30, 40, 50, 60, 70, 100, 200, 500 or more different nucleic acid templates.

In some embodiments, in a method provided herein, a nucleic acid template may be amplified rapidly. For example, in some embodiments, a nucleic acid template may be amplified at least 500-fold within 0.1, 0.5, 1, 3, 5, 10, 15, 20, 30, 40, 50, 60, 90, 120, or 180 minutes of starting the method. In another example, in some embodiments, a nucleic acid template may be amplified at least 10,000-fold within 0.1, 0.5, 1, 3, 5, 10, 15, 20, 30, 40, 50, 60, 90, 120, or 180 minutes of starting the method. In another example, in some embodiments, a nucleic acid template may be amplified at least 5, 10, 25, 50, 100, 250, 500, 1,000, 5,000, 10,000, 50,000, 100,000, 500,000, or 1,000,000-fold over the original amount of the nucleic acid template present in a reaction mixture at the start of the method within 0.1 minute, 0.5 minute, 1 minute, 3 minutes, 5 minutes, 10 minutes, 15 minutes, 20 minutes, 30 minutes, 40 minutes, 50 minutes, 60 minutes, 90 minutes, 2 hours, 3 hours, 4 hours, 6 hours, 8 hours, 12 hours, 16 hours, or 24 hours of initiation of the method. In some embodiments, when a method is initiated, all of the reagents for the first step of the method are in a vessel containing the reaction mixture for the method. In some embodiments, when a method is initiated, all of the reagents for all of the steps of the method are in a vessel containing the reaction mixture for the method.

In some embodiments, in a method provided herein, a nucleic acid template may be amplified at greater than a linear rate. In some embodiments, in a method provided herein, a nucleic acid template may be amplified exponentially. In some embodiments, in a method provided herein, a nucleic acid template may at least double in number every 1, 2, 3, 5, 10, 15, 20, 25, 30, 45, 60, 90, 120, 180, or 240 minutes after the initiation of the method. In some embodiments, a nucleic acid template may amplified at least 5, 10, 25, 50, 100, 250, 500, 1,000, 5,000, 10,000, 50,000, 100, 000, 500,000, 1,000,000, or 10,000,000-fold over the original amount of the nucleic acid template present in the reaction at the start of the method.

The presence of multiple copies of a nucleic acid template in a concatemer generated according to a method provided herein may contribute to the rapid amplification of nucleic acid templates according to methods provided herein. In particular, since multiple copies of a strand of a nucleic acid template may be present in a single concatemer strand, the loading of a single polymerase onto a single concatemer strand may result in the generation of multiple copies of a strand of the nucleic acid template as the polymerase moves along the concatemer strand. In some situations, the time required for nucleic acid polymerases to encounter and load onto nucleic acid strands may significantly impact the overall speed of an amplification reaction. For example, if each nucleic acid strand that a polymerase encounters during a replication reaction only contains a single copy of a strand of a nucleic acid template, a polymerase may need to encounter and load onto a new template strand after each copy of the strand of the template is generated. In contrast, with a concatemer, after the polymerase encounters and loads on a concatemer strand, it may synthesize multiple copies of a strand of the template without needing to leave the concatemer strand or encounter and load onto another strand.

In some embodiments, provided herein are methods and compositions for the generation of a double-stranded DNA concatemer from a single-stranded or double-stranded RNA template. The method may be performed as described herein, except that a reverse transcriptase enzyme (e.g. AMV reverse transcriptase, M-MLV reverse transcriptase, Superscript II™ reverse transcriptase, Superscript III™ reverse transcriptase, or ThermoScript™ reverse transcriptase) is also included with the methods provided herein. The first copy of the first primer may anneal to the RNA template, and the reverse transcriptase enzyme may generate the extension product of the first copy of the first primer, which is formed as a DNA strand by the process of reverse transcription. Methods and conditions for reverse transcription of RNA are known in the art and are disclosed, for example, in RNA: A Laboratory Manual, D. Rio et al., Cold Spring Harbor Laboratory Press (2011), which is herein incorporated by reference in its entirety. After the generation (from an RNA strand) of the extension product of the first copy of the first primer (which is a DNA strand) by a reverse transcriptase enzyme, the rest of the steps for the generation of a concatemer may be the same as described elsewhere herein.

In some embodiments, methods and compositions provided herein may include one or more "bumping primers". Bumping primers may be used with methods and compositions provided herein to, for example, increase the rate or specificity of generation of reaction products by, for example, increasing the rate at which a second strand of nucleic acid template is displaced from a first strand of nucleic acid template, increasing the rate at which a first strand of a nucleic acid template is displaced from a first primer extension product, or increasing the rate at which a first primer extension product is displaced from a second primer extension product. As used herein a "bumping primer" refers to a primer which is complementary to a sequence on a first strand or second strand of a nucleic acid template which is downstream from a sequence on the same strand to which the template-binding region of a first primer or second primer binds. Thus, when a bumping primer is annealed to the same nucleic acid strand that a first primer or second primer is annealed to, the 3' terminus of the bumping primer is oriented towards the 5' terminus of the first primer or second primer (i.e. the 5' terminal nucleotide and tail region of the first primer or second primer). When incubated with a nucleic acid polymerase and under conditions to support the generation of primer extension products, an extension product of a bumping primer may be formed by the polymerase, from the 3' terminus of the bumping primer. Since the 3' terminus of the bumping primer is oriented toward the 5' terminus of the first primer or second primer, as the extension product of the bumping primer increases in length, it may eventually encounter the 5' terminus of the first primer or second primer as the extension product. The polymerase may then displace the first primer or second primer from the strand, as well as any extension product of the first primer or second primer. Accordingly, bumping primers may accelerate reactions provided herein.

In some embodiments, provided herein is a vessel containing one or more enzymes, primers, or other reagents provided herein. Vessels may include any structure capable of supporting or containing a liquid or solid material and may include, tubes, containers, tips, etc. In some embodiments, a wall of a vessel may permit the transmission of light through the wall. A vessel may be optically clear. A vessel may contain, for example, any one or more of an isolated nucleic acid polymerase, an isolated DNA polymerase, an isolated reverse transcriptase, a first primer, a second primer, a nucleic acid dye, or a nucleic acid probe, as described elsewhere herein. Any number of copies of any of the contents of a vessel may be provided (e.g. a first copy, a second copy, a third copy, etc.) The contents of a vessel may be in fluid communication. In some embodiments, a vessel may further contain a nucleic acid template. In some embodiments, a vessel may further contain nucleotides, buffers, salts, water, or other reagents provided herein for the amplification of nucleic acids. In some embodiments, a vessel may contain two or more sets of primers, wherein each primer set comprises a first and second primer, and the different primer sets are complementary to different nucleic acid templates.

Two or more reagents useful for a method provided herein may be packaged and provided as a kit. For example, a kit may include any two or more of: a nucleic acid template, a first primer, a second primer, a nucleic acid polymerase, a DNA polymerase, a reverse transcriptase, buffers, a nucleic acid dyes, a nucleic acid probe, or dNTPs, as described elsewhere herein. Within the kit, the two or more reagents may be packaged in separate vessels or the same vessel. In some embodiments, a kit may further contain nucleotides, buffers, salts, water, or other reagents provided herein for the amplification of nucleic acids.

In embodiments, a first primer and second primer as provided herein may be provided together as a primer set. The primer set may be provided as a stand-alone kit or composition, or the primer set may be provided in a kit with one or more other reagents for performing a method provided herein.

In some embodiments, a nucleic acid ligase may be included with a method or composition provided herein. Ligases catalyze the formation of phosphodiester bonds between nucleotides, typically between the 5' phosphate of one nucleotide, and the 3' hydroxyl group of another nucleotide. A reaction provided herein may amplify a target nucleic acid at a greater rate with the inclusion of a ligase in the reaction, as compared to the reaction without the inclusion of a ligase. A ligase may, for example, increase the size or number of concatemers present in a reaction provided herein.

Nucleic acid ligases include *E. coli* DNA ligase, Taq DNA ligase, T3 DNA ligase, T4 DNA ligase, T7 DNA ligase, Ampligase™, T4 RNA ligase 1, and T4 RNA ligase 2.

In order to catalyze the ligation reaction, certain ligases require ATP (e.g. T4 DNA ligase) or NAD+ (*E. coli* DNA ligase). In some embodiments, a ligase may ligate nucleic acids having blunt ends. In some embodiments, a ligase may ligate nucleic acids having sticky ends. In some embodiments, a ligase may ligate nucleic acids having both blunt and sticky ends.

Modified versions ligases may also be used with the methods and compositions provided herein, provided that the modified ligase has the ability to catalyze the formation of phosphodiester bonds between nucleotides. A modified version of a ligase ("modified ligase") may have, for example, 100 or fewer, 70 or fewer, 50 or fewer, 40 or fewer, 30 or fewer, 20 or fewer, 10 or fewer, 5 or fewer, 4 or fewer, 3 or fewer, 2 or fewer, or 1 different amino acid from the sequence of the parent, naturally occurring version of the ligase. In some embodiments, a modified ligase may contain no more than 1000, 700, 500, 400, 300, 200, 100, 50, 40, 30, 20, 10, or 5 greater or fewer amino acids than the parent ligase. In some embodiments, a modified ligase may comprise a fragment of a parent ligase. In some embodiments, a modified ligase may comprise a chimeric polypeptide with a portion derived from a ligase and a portion derived from a non-ligase protein. In some embodiments, a modified ligase may have, for example, increased catalytic activity, increased stability, or increased thermostability as compared to the parent ligase.

In some embodiments, a ligase provided herein is thermostable. A thermostable ligase may have, for example, a half-life of at least 5, 10, 15, 20, 30, 40, 50, 60, 90, 120, or 180 minutes at a temperature of at up to 25, 30, 35 40, 45, 50, 55, 60, 65, 70, 75, 80, 85, 90, or 95 C. In some embodiments, a modified ligase may be thermostable.

In some embodiments, a ligase included with methods and compositions provided herein may be a modified ligase referred to herein as "p50-Tth", which has the amino acid sequence:

```
                                            (SEQ ID NO: 79)
MGHHHHHHHHHHSSGHIEGRASADGPYLQILEQPKQRGFRFRYVCEGPSH

GGLPGASSEKNKKSYPQVKICNYVGPAKVIVQLVTNGKNIHLHAHSLVGK

HCEDGICTVTAGPKDMVVGFANLGILHVTKKKVFETLEARMTEACIRGYN

PGLLVHPDLAYLQAEGGGDRQLGDREKELIRQAALQQTKEMDLSVVRLMF

TAFLPDSTGSFTRRLEPVVSDAIYDSKAPNASNLKIVRMDRTAGCVTGGE

EIYLLCDKVQKDDIQIRFYEEEENGGVWEGFGDFSPTDVHRQFAIVFKTP

KYKDINITKPASVFVQLRRKSDLETSEPKPFLYYPEIKDKEEVQRKRQKG

SSGTSGGGSGGGMTLEEARKRVNELRDLIRYHNYRYYVLADPEISDAEYD

RLLRELKELEERFPELKSPDSPTLQVGARPLEATFRPVRHPTRMYSLDNA

FNLDELKAFEERIERALGRKGPFAYTVEHKVDGLSVNLYYEEGVLVYGAT

RGDGEVGEEVTQNLLTIPTIPRRLKGVPERLEVRGEVYMPIEAFLRLNEE
```

-continued

LEERGERIFKNPRNAAAGSLRQKDPRITAKRGLRATFYALGLGLEEVERE

GVATQFALLHWLKEKGFPVEHGYARAVGAEGVEAVYQDWLKKRRALPFEA

DGVVVKLDELALWRELGYTARAPRFAIAYKFPAEEKETRLLDVVFQVGRT

GRVTPVGILEPVFLEGSEVSRVTLHNESYIEELDIRIGDWVLVHKAGGVI

PEVLRVLKERRTGEERPIRWPETCPECGHRLLKEGKVHRCPNPLCPAKRF

EAIRHFASRKAMDIQGLGEKLIERLLEKGLVKDVADLYRLRKEDLVGLER

MGEKSAQNLLRQIEESKKRGLERLLYALGLPGVGEVLARNLAARFGNMDR

LLEASLEELLEVEEVGELTARAILETLKDPAFRDLVRRLKEAGVEMEAKE

KGGEALKGLTFVITGELSRPREEVKALLRRLGAKVTDSVSRKTSYLVVGE

NPGSKLEKARALGVPTLTEEELYRLLEARTGKKAEELV.

Ligase p50-Tth has thermostable blunt-end ligation activity at temperatures of at least 60 C. Ligase p50-Tth is a chimeric protein which comprises a His10-containing leader sequence, a p50 sequence from the human NF-kappa-B protein accession number NP_003989 amino acids 40-366 (indicated in italics), a flexible glycine rich sequence, and a Tth DNA ligase sequence, from *Thermus Thermophilus* HB8, accession YP_144363 (indicated with underlining). In some embodiments, a modified version of p50-Tth ligase may be used with methods and compositions provided herein (e.g. with 100 or fewer, 70 or fewer, 50 or fewer, 40 or fewer, 30 or fewer, 20 or fewer, 10 or fewer, 5 or fewer, 4 or fewer, 3 or fewer, 2 or fewer, or 1 different amino acids from p50-Tth ligase). In embodiments, a ligase used with a composition or method provided herein may be a ligase described in U.S. Provisional Patent Application No. 61/802,124, filed Mar. 15, 2013 or PCT Application No. PCT/US14/30003, filed Mar. 15, 2014, both of which are herein incorporated by reference in their entirety for all purposes.

The various methods and compositions provided herein for the amplification of a nucleic acid template/the generation of a concatemer containing at least two copies of the template can fulfill many of the functions that have previously been carried out by other methods and compositions for isothermal and thermocycler-dependent nucleic acid amplification. A nucleic acid template for amplification according to methods provided herein may also be referred to herein as a "target nucleic acid" or the like. Methods and compositions provided herein may be used, for example, for isolation and cloning of nucleic acids of interest, gene expression analysis, diagnostic identification of nucleic acids, synthesis of novel nucleic acids, nucleic acid probe synthesis and labeling, forensic identification of a subject, allele identification from a subject, genetic screening, nucleic acid sequencing, and related applications. A target nucleic acid molecule may be of any type, including single-stranded or double stranded and DNA or RNA (e.g. mRNA). A target nucleic acid may be of any type or function (e.g. a protein-coding sequence, a regulatory sequence, an intron, etc.). A target nucleic acid may be the entirety of a gene, or a portion thereof.

In some embodiments, a method or composition provided herein may be used to detect the amount of a target nucleic acid in a sample (including the presence or absence of the target), to measure the amount of an amplification product of a target formed from a sample in a selected period of time, or to determine the amount of time necessary to generate a certain number of copies of a template from a sample. Samples which may be used with methods and compositions provided herein are described elsewhere herein, and may include, for example, a bodily fluid, a secretion, or a tissue of a subject. In embodiments, a sample may be processed prior to use of the sample in an assay to amplify a target nucleic acid in the sample according to a method provided herein. Processing of the sample may include any processing step as described elsewhere herein, and may include, for example, sonication or chemical lysing steps.

In some embodiments, a method provided herein may be performed to simultaneously assay for at least 2, 3, 4, 5, 6, 7, 8, 9, 10, 12, 15, 20, 25, 30, 35, 40, 45, 50, 75, 100, or more different target nucleic acids in the same reaction vessel. Typically, for each target nucleic acid of interest, a first primer and a second primer are provided, each being complementary to a strand of the nucleic acid target, or a complement thereof. The amplification of the different target nucleic acids in the same vessel may be monitored, for example, by the use of nucleic acid probes having sequence specificity for detection sequences in the different target nucleic acids, and different fluorophores.

In some embodiments, a method or composition provided herein may be used to detect the presence or absence of a particular nucleotide of interest in a target nucleic acid (e.g. in the case of a mutation or SNP). For example, a first or second primer may be selected which selectively binds to a region in a target nucleic acid which includes or is adjacent to the nucleotide of interest. The primer may be designed such that it selectively either: i) binds to the region when the region contains the nucleotide of interest, or ii) does not bind to the region when the region contains the nucleotide of interest. A method as described herein may be performed with the selected primer, and the outcome of the amplification reaction may provide information regarding the presence or absence of the nucleotide of interest in the target nucleic acid. For example, if the template-binding region of a first primer is designed to have a nucleotide sequence which is complementary to a sequence in the target nucleic acid which includes a particular nucleotide of interest (e.g. a mutation), successful amplification of the target nucleic acid with the selected primer from a sample may indicate that the sample contains a target nucleic acid having the particular nucleotide of interest. In some embodiments, a primer used for analysis of a nucleotide of interest in a target nucleic acid may contain a critical nucleotide (i.e. a nucleotide which corresponds to the same position of a nucleotide of interest in the target nucleic acid) at the 3' terminus of the primer. In such a case, the annealing of the 3' terminal nucleotide of the primer may be dependent on the presence of the nucleotide of interest in the target nucleic acid. If the 3' terminal nucleotide of the primer does not anneal with a nucleotide in the target nucleic acid (e.g. due to a mismatch between the nucleotides), the mismatch may significantly impair a nucleic acid polymerase from synthesizing an extension product from the primer. Accordingly, in some embodiments, a primer having a 3' terminal nucleotide which corresponds to a nucleotide of interest may be useful for determining the presence or absence of a particular nucleotide in a target nucleic acid. In such embodiments, in some situations the critical nucleotide at the 3' terminus of the primer may be selected to be complementary the nucleotide of interest in the target nucleic acid, and in some other situations the critical nucleotide at the 3' terminus of the primer may be selected to be non-complementary the nucleotide of interest in the target nucleic acid. The nucleotide of interest may represent, for example, a wild-type form, a mutant form, or a polymorphism of a target nucleic acid.

Methods and compositions provided herein may be used to amplify a nucleic acid from any sample which may contain nucleic acids. Examples of samples may include various fluid samples. In some instances, the sample may be a bodily fluid sample from a subject. The sample may include one or more fluid component. In some instances, solid or semi-solid samples may be provided. The sample may include tissue collected from the subject. The sample may include a bodily fluid, secretion, or tissue of a subject. The sample may be a biological sample. The biological sample may be a bodily fluid, a secretion, or a tissue sample. Examples of biological samples may include but are not limited to, blood, serum, saliva, urine, gastric and digestive fluid, tears, stool, semen, vaginal fluid, interstitial fluids derived from tumorous tissue, ocular fluids, sweat, mucus, earwax, oil, glandular secretions, breath, spinal fluid, hair, fingernails, skin cells, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk or other excretions. The sample may be provided from a human or animal. Samples may be from a plant, microorganism (e.g. virus, bacteria), or other biological material.

In some embodiments, methods and compositions provided herein may be performed at or used at point of service locations (e.g. a subject's home or work, grocery stores, drug stores, clinics, schools, etc.). Methods and compositions provided herein may permit the rapid amplification of nucleic acids in a sample from a subject, in order to aid in the diagnosis or treatment of a subject. For example, methods and compositions provided here may be used test a sample from a subject for the presence of nucleic acid from a pathogen, such a virus (e.g. influenza) or bacteria (e.g. *streptococcus*).

The assays and methods disclosed herein may be performed on a device, or on a system, for processing a sample. The assays and methods disclosed herein can be readily incorporated into and used in a device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be a sample processing device. A device may be a sample processing device. A sample processing device may be configured to facilitate collection of a sample, prepare a sample for a clinical test, or perform a method with one or more reagents, as disclosed herein. A sample processing device may be configured to obtain data from a sample. A sample processing device may be configured to transmit data obtained from a sample. A sample processing device may be configured to analyze data from a sample. A sample processing device may be configured to communicate with another device, or a laboratory, or an individual affiliated with a laboratory, to analyze data obtained from a sample.

A sample processing device may be configured to be placed in or on a subject. A sample processing device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. A sample processing device may receive a sample from the subject through a housing of the device. The sample collection may occur at a sample collection site, or elsewhere. The sample may be provided to the device at a sample collection site.

In some embodiments, a sample processing device may be configured to accept or hold a cartridge. In some embodiments, a sample processing device may comprise a cartridge. The cartridge may be removable from the sample processing device. In some embodiments, a sample may be provided to the cartridge of the sample processing device. Alternatively, a sample may be provided to another portion of a sample processing device. The cartridge and/or device may comprise a sample collection unit that may be configured to accept a sample.

A cartridge may include a sample, and may include reagents for use in processing or testing a sample, disposables for use in processing or testing a sample, or other materials. A cartridge may contain reagents disclosed herein for the performing a method disclosed herein. Following placement of a cartridge on, or insertion of a cartridge into, a sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a sample handling system in a similar manner. One or more components of the cartridge may be transferred in an automated fashion to other portions of the sample processing device, and vice versa.

A device, such as a sample processing device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing.

A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have a portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

A sample processing device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification; precipitation, incubation, pipetting, transport, chromatography, cell lysis, cytometry, pulverization, grinding, activation, ultrasonication, micro column processing, processing with magnetic beads; processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing device may be configured to run one or more assays on a sample, and to obtain data from the sample. A sample processing device may perform methods provided herein, as well as additional assays. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example, one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, less than about 5 µL, less than about 1 µL, less than about 0.5 µL, less than about 0.1 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

A sample processing device may be configured to perform a plurality of assays on a sample. In some embodiments, a sample processing device may be configured to perform a method provided herein and one, two, or more additional assays. In embodiments, a sample processing device may be configured to perform a plurality of assays on a single sample. In embodiments, a sample processing device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, less than about 5 µL, less than about 1 µL, less than about 0.5 µL, less than about 0.1 µL, or other small volume. A sample processing device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

A sample processing device may be configured to detect one or more signals relating to the sample. A sample processing device may be configured to identify one or more properties of the sample. For instance, the sample processing device may be configured to detect the presence or concentration of one analyte (e.g. a target nucleic acid) or a plurality of analytes or a disease condition in the sample (e.g., in or through a bodily fluid, secretion, tissue, or other sample). Alternatively, the sample processing device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing steps may be performed, with or without the sample. Examples of steps, tests, or assays that may be prepared or run by the device may include, but are not limited to immunoassay, nucleic acid assay (e.g. methods provided herein), receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, a sample processing device may be configured to transmit data obtained from a sample. In embodiments, a sample processing device may be configured to communicate over a network. A sample processing device may include a communication module that may interface with the network. A sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device, or an intermediary device may be required to connect a sample processing device to a network. A sample processing device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

A sample processing device may provide data regarding a sample to, e.g., a health care professional, a health care professional location, such as a laboratory, or an affiliate thereof. One or more of a laboratory, health care professional, or subject may have a network device able to receive or access data provided by the sample processing device. A sample processing device may be configured to provide data regarding a sample to a database. A sample processing device may be configured to provide data regarding a sample to an electronic medical records system, to a laboratory information system, to a laboratory automation system, or other system or software. A sample processing device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by a sample processing device, or analysis of such data, or reports, may be provided to a database, an electronic medical records system, to a laboratory information system, to a laboratory automation system, or other system or software.

Description and disclosure of examples of reagents, assays, methods, kits, devices, and systems which may use, or be used with, methods, compositions, or other reagents disclosed herein may be found, for example, in U.S. Pat. No. 8,088,593; U.S. Pat. No. 8,380,541; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

This application claims the benefit of, and priority to U.S. Provisional Patent Application No. 61/800,606, filed Mar. 15, 2013, the disclosure of which is hereby incorporated by reference in its entirety for all purposes.

EXAMPLES

The following examples are offered for illustrative purposes only, and are not intended to limit the present disclosure in any way.

Example 1—Amplification of a Template Nucleic Acid with Primers of Variable Tail Region Length A method as provided herein was used to amplify a target nucleic acid. Reactions were prepared to assay for about an 102 nucleotide portion of target nucleic acid T124A1, which is a 464 nucleotide portion of an influenza A virus hemagglutinin (HA3) gene (an RNA molecule). The nucleotide sequence of T124A1 is provided in SEQ ID NO: 89. 12 variants of a first primer ("P1") and 12 variants of a second primer ("P2") were prepared. The sequences of all of the primer variants are provided in FIG. 2A. All of the primers contained a template-binding region 15 nucleotides in length. The sequence of the template-binding region of all of the variants of the first primer was: CAAACCGTAC-CAACC (SEQ ID NO: 80) (in the 5'-3' direction). The sequence of the template-binding region of all of the variants of the second primer was: ATGCGGAATGTACC (SEQ ID NO: 81) (in the 5'-3' direction). The different primer variants contained tail regions ranging from 8 to 22 nucleotides in length, specifically 8, 9, 10, 11, 12, 13, 14, 15, 16, 18, 20, or 22 nucleotides in length. The tail region of the first primer had a base sequence of: CGCCGGATGGCTCT-TGGGAAAC (SEQ ID NO: 82) (in the 5'-3' direction). The base sequence is 22 nucleotides in length; the shorter tail regions of the first primer have the same sequence, minus the appropriate number of nucleotides from the 5' end of the tail region (e.g. the primer with the 18 nucleotide length tail region has a tail region with the same sequence as the base sequence, minus the first 4 nucleotides (CGCC) of the base sequence). The tail region of the second primer had a base sequence of: GTTTCCCAAGAGCCATCCGGCG (SEQ ID NO: 83) (in the 5'-3' direction). The base sequence is 22 nucleotides in length; the shorter tail regions of the first primer have the same sequence, minus the appropriate number of nucleotides from the 3' end of the tail region (e.g. the primer with the 18 nucleotide length tail region has a tail region with the same sequence as the base sequence, minus the last 4 nucleotides (GGCG) of the base sequence).

150 microliter reaction mixtures were prepared, each containing: 50 mM potassium acetate, 20 mM Tris-acetate, pH 7.9, 10 mM magnesium acetate, 1 mM DTT, 30 µg bovine serum albumin (BSA), 0.8 M betaine, 1.4 mM each of dATP, dTTP, dGTP, and dCTP, 2 uM SYTO® 59 (Life Technologies), 0.8 units/µl Bst DNA polymerase (New England BioLabs), 0.016 units/µl AMV reverse trancriptase enzyme (New England Biolabs), 1 unit/µl murine RNase inhibitor (New England Biolabs), 0.8 µM of a first primer variant, 0.8 µM of a second primer variant, and 100,000 copies T124A1 template per microliter, and incubated at 59 C for 100 minutes in a CFX 96 Touch instrument (Bio-Rad). The inflection points for the assays were determined using a single-threshold method with CFX Manager software (Bio-Rad), and are shown in FIG. 2B. The X-axis provides the length in nucleotides of the tail region of the first and second primer used in the reaction, and the Y-axis provides the inflection time (in minutes) of the assay. For each tail region nucleotide length, two adjacent bars are shown: the left bar is the inflection time for the reaction containing template, and the right bar is the inflection time for the reaction lacking template ["no template control" ("NTC")]. For inflection times over 90 minutes, no bar is shown. As shown in FIG. 2B, under these reaction conditions, primers with tail regions of 8-15 nucleotides, and, more particularly, 8-11 nucleotides supported the fastest inflection times. The no template control reactions eventually show an inflection time; this is due to background non-specific products that are formed over time.

Example 2—Amplification of a Template Nucleic Acid with Primers of Variable Tail Region Length and Variable Template-Binding Region Length A method as provided herein was used to amplify a target nucleic acid. Reactions were prepared to assay for target nucleic acid T124A1, which is described above in Example 1. Two different groups of first primer and second primer pair sets were prepared. In the first group of primer pairs, each of the primers had a template binding region 20 nucleotides in length (the "20 nucleotide template binding region" group). In the second group of primer pairs, each of the primers had a template binding region 16 nucleotides in length (the "16 nucleotide template binding region" group). Within each group, first and second primer pair sets with 8 different tail region lengths were prepared: 7, 8, 9, 10, 11, 12, 14, and 16 nucleotides. FIG. 3 provides the nucleotide sequences of the different primer pair sets for the 16 nucleotide template binding region group (FIG. 3A) and the 20 nucleotide template binding region group (FIG. 3B). In FIGS. 3A and 3B, the "tail" sequence refers to the tail region, and the "primer" region refers to the template-binding region of the primer. The sequences of the primers are shown in the 5'-3' direction.

110 microliter reaction mixtures were prepared, each containing: 50 mM potassium acetate, 20 mM Tris-acetate, pH 7.9, 10 mM magnesium acetate, 1 mM DTT, 30 µg bovine serum albumin (BSA), 0.8 M betaine, 1.4 mM each of dATP, dTTP, dGTP, and dCTP, 2 uM SYTO® 59 (Life Technologies), 0.8 units/µl Bst DNA polymerase (New England BioLabs), 0.016 units/µl AMV reverse transcriptase enzyme (New England Biolabs), 1 unit/µl murine RNase inhibitor (New England Biolabs), 0.8 µM of a first primer variant, 0.8 µM of a second primer variant, and 100,000 copies T124A1 template per microliter, and incubated at 56 C for 100 minutes in a CFX 96 Touch instrument (Bio-Rad). The inflection points for the assays are shown in FIG. 3C (20 nucleotide template binding region group) and 3D (16 nucleotide template binding region group). In both FIGS. 3C and 3D, the X-axis provides the length in nucleotides of the tail region of the first and second primer used in the reaction, and the Y-axis provides the inflection time (in minutes) of the assay. For each tail region nucleotide length, two adjacent bars are shown: the left bar is the inflection time for the reaction containing template, and the right bar is the inflection time for the reaction lacking template. As shown in FIG. 3, under these reaction conditions, reactions containing primers having relatively shorter tail regions showed faster inflection times and greater separation between the inflection time of reactions containing template versus reactions without template. For example, for both the 16 bp and 20 bp primers, reactions containing primers having a tail region length of 7, 8, or 9 nucleotides showed faster inflection times than reactions containing primers having a tail region length of 12, 14, or 16 nucleotides.

Example 3—Amplification of a Template Nucleic Acid at Variable Temperatures

A method as provided herein was used to amplify a target nucleic acid. Reactions were prepared to assay for target nucleic acid T124A1, described above in Example 1. First primer "RLX0892" (sequence: 5' TTGGGAAACCAAAC- CGTACCAACC 3')(SEQ ID NO: 20) and second primer "RLX0893" (sequence: 5' GTTTCCCAAATGCGGAATG- TACC 3')(SEQ ID NO: 32) were used to amplify T124A1. Both of these primers have a 9 nucleotide tail region, RLX0892 has a 15 nucleotide template-binding region and RLX0893 has a 14 nucleotide template-binding region. The tail region of RLX0892 is: 5' TTGGGAAAC 3' (SEQ ID NO: 84) and the tail region of RLX0893 is: 5' GTTTC- CCAA 3' (SEQ ID NO: 85).

80 microliter reaction mixtures were prepared, each containing: 50 mM potassium acetate, 20 mM Tris-acetate, pH 7.9, 10 mM magnesium acetate, 1 mM DTT, 20 µg bovine serum albumin (BSA), 0.8 M betaine, 1.4 mM each of dATP, dTTP, dGTP, and dCTP, 2 uM SYTO® 59 (Life Technologies), 0.8 units/µl Bst DNA polymerase (New England BioLabs), 0.016 units/µl AMV reverse transcriptase enzyme (New England Biolabs), 1 unit/µl murine RNase inhibitor (New England Biolabs), 0.8 µM of first primer RLX0892, 0.8 µM of second primer RLX0893, and 10,000, 1,000, 100 or 0 copies T124A1 template per microliter, and incubated in triplicate at 52, 52.7, 54, 55.9, 58.4, 60.3, 61.4 or 62 C for 100 minutes in a CFX 96 Touch instrument (Bio-Rad). The inflection points for the assays are shown in FIG. 4. The X-axis provides the incubation temperature of the reaction, and the Y-axis provides the inflection time (in minutes) of the assay. For each temperature, 4 adjacent bars are shown, from left to right: 10,000 copies template/microliter, 1000 copies template/microliter, 100 copies template/microliter, or no template control. As shown in FIG. 4, under these reaction conditions, the assays effectively amplified the template at 1000 copies template/microliter across the full range of temperatures from 52-62 C, and at some temperatures, at concentrations of template at least as low as 100 copies template/microliter.

Example 4—Amplification of a Template Nucleic Acid in the Presence of Human Genomic DNA A method as provided herein was used to amplify a target nucleic acid. Reactions were prepared to assay for target nucleic acid T124A1 (described above) in the presence of human DNA. First primer "RLX0892" (described above) and second primer "RLX0893" (described above) were used to amplify T124A1.

160 microliter reaction mixtures were prepared, each containing: 50 mM potassium acetate, 20 mM Tris-acetate, pH 7.9, 10 mM magnesium acetate, 1 mM DTT, 20 µg bovine serum albumin (BSA), 0.8 M betaine, 1.4 mM each of dATP, dTTP, dGTP, and dCTP, 0.4×SYTO® 59 (Life Technologies), 0.8 units/µl Bst DNA polymerase (New England BioLabs), 0.016 units/µl AMV reverse transcriptase enzyme (New England Biolabs), 1 unit/µl murine RNase inhibitor (New England Biolabs), 0.8 µM of first primer RLX0892, 0.8 µM of second primer RLX0893, and 1,000, 100 or 0 copies T124A1 template per microliter, and 0, 1, 2.5, 5, or 10 nanograms human genomic DNA, and incubated at 56 C for 100 minutes in a CFX 96 Touch instrument (Bio-Rad). The inflection points for the assays are shown in FIG. 5. The X-axis provides the quantity of human genomic DNA ("hDNA") in the reaction, and the Y-axis provides the inflection time (in minutes) of the assay. For each quantity of hDNA, 3 adjacent bars are shown, from left to right: 1000 copies template/microliter, 100 copies template/microliter, or no template. As shown in FIG. 5, under these reaction conditions, the assays effectively amplified the template at 1000 copies template/microliter in the presence of at least 10 ng hDNA. Also, the addition of hDNA the reactions caused only a relatively small decrease in NTC inflection times, even at concentrations of 5 or 10 ng hDNA.

Example 5—Amplification of a Template Nucleic Acid from a Viral Lysate Eluate

A method as provided herein was used to amplify a target nucleic acid from two different samples containing the target. Target nucleic acid T124A1 was prepared in two samples: 1) a sample containing isolated T124A1 RNA molecule (as in Example 1), and 2) a sample containing isolated nucleic acids from an influenza A H3N2 viral sample. T124A1 is a portion of the HA3 gene, and therefore is expected to be present in a sample of isolated nucleic acids from influenza A H3N2 virus. Influenza A viral lysate was prepared with a Chemagic viral DNA/RNA kit (PerkinElmer), according to the manufacturer's instructions. The concentration of T124A1 in the two different samples was quantified by qPCR, and the samples were diluted to normalize the concentration of T124A1 in the samples. First primer "RLX0892" and second primer "RLX0893" were used to amplify T124A1.

25 microliter reaction mixtures were prepared, each containing: 50 mM potassium acetate, 20 mM Tris-acetate, pH 7.9, 10 mM magnesium acetate, 1 mM DTT, 20 µg bovine serum albumin (BSA), 0.8 M betaine, 1.4 mM each of dATP, dTTP, dGTP, and dCTP, 2 uM SYTO® 59 (Life Technologies), 0.8 units/µl Bst DNA polymerase (New England BioLabs), 0.016 units/µl AMV reverse trancriptase enzyme (New England Biolabs), 1 unit/µl murine RNase inhibitor (New England Biolabs), 0.8 µM of first primer RLX0892, 0.8 µM of second primer RLX0893, and 10,000, 1000 or 0 copies T124A1 template per microliter, and incubated at 56 C for 100 minutes in a CFX 96 Touch instrument (Bio-Rad). The inflection points for the assays are shown in FIG. 6. The X-axis provides the copies of template/microliter in the reaction, and the Y-axis provides the inflection time (in minutes) of the assay. For each quantity of copies of template/microliter, 2 adjacent bars are shown, from left to right: isolated T124A1, and influenza A viral lysate. The inflection point for the NTC is also shown. As shown in FIG. 6, under these reaction conditions, the assays effectively amplified both isolated T124A1 template, as well as T124A1 template in an influenza A viral lysate.

Example 6—Amplification of a Template Nucleic Acid

A method as provided herein was used to amplify a target nucleic acid. Reactions were prepared to assay for a 54 nucleotide portion of T129D1, which is a 298 nucleotide portion of an influenza B virus hemagglutinin (HA) gene (an RNA molecule). The nucleotide sequence of T129D1 is provided in SEQ ID NO: 90. First primer "A8" (nucleotide sequence: 5' TCTTGAGAGAACCCACTAAC 3') (SEQ ID NO: 86) and second primer "B8" (nucleotide sequence: 5' TCTCAAGAATTTGGTCTTCC 3') (SEQ ID NO: 87) were used to amplify T129D1. In both of these primers, the first 8 nucleotides (from the 5' terminus) are the tail region, and the last 12 nucleotides are the template-binding region. Together, these primers target a 54 nucleotide portion of T129D1.

A 100 microliter reaction mixture was prepared, containing: 50 mM potassium acetate, 20 mM Tris-acetate, pH 7.9, 10 mM magnesium acetate, 1 mM DTT, 20 µg bovine serum albumin (BSA), 0.8 M betaine, 1.4 mM each of dATP, dTTP, dGTP, and dCTP, 0.4×SYTO® 59 (Life Technologies), 0.8 units/µl Bst DNA polymerase (New England BioLabs), 0.016 units/µl AMV reverse trancriptase enzyme (New England Biolabs), 1 unit/µl murine RNase inhibitor (New England Biolabs), 0.8 µM of first primer A8, 0.8 µM of second primer B8, and 100,000 T129D1 template per microliter, and incubated at 58 C for 100 minutes in a CFX 96 Touch instrument (Bio-Rad). After the 100 minutes, a sample was taken from the reaction, and ligated into cloning vectors. Vectors containing reaction products were sequenced using vector-specific primers, directed to toward the cloning site. A portion of the results from multiple example sequencing reactions are shown in FIG. 7. The sequencing results show that concatemers having the expected structure are formed. Specifically, in these examples, in a single strand of the reaction product, multiple copies of the targeted 54 nucleotide sequence from the T129D1 gene are present, separated by the sequence of the tail region of the A8 primer (5' TCTTGAGA 3') (SEQ ID NO: 88). In FIG. 7, only a portion of the second (from left to right) occurrence of the T129D1 is shown; the sequences continue beyond the nucleotides shown in the figure.

Nucleotide and amino acid sequences provided herein are artificial sequences, unless otherwise noted.

While preferred embodiments of the present invention have been shown and described herein, it will be obvious to those skilled in the art that such embodiments are provided by way of example only. The foregoing description is not intended to be exhaustive or to limit the invention to the precise embodiments disclosed, and other modifications and variations may be possible in light of the above teachings without departing from the invention. Any feature, whether preferred or not, may be combined with any other feature, whether preferred or not. It should also be understood that while the invention provided herein has been described herein using a limited number of terms and phrases for purposes of expediency, the invention could also be described using other terms and phrases not provided herein which also accurately describe the invention. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. As used in the description herein and through the claims that follow, a first object described as containing "at least a portion" of a second object may contain the full amount of/the complete second object. As used in the description herein and throughout the claims that follow, the terms "comprise", "include", and "contain" and related tenses are inclusive and open-ended, and do not exclude additional, unrecited elements or method steps. Also, the presence of broadening words and phrases such as "one or more," "at least," "but not limited to" or other like phrases in some instances shall not be read to mean that the narrower case is intended or required in instances where such broadening phrases may be absent. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction by anyone of the patent documents or the patent disclosure, as they appear in the US Patent and Trademark Office patent file or records, but otherwise reserves all copyright rights whatsoever. The following notice shall apply: Copyright 2013-14 Theranos, Inc.

| SEQUENCE LISTING |
| --- |
| SEQ ID NO: 1: AACGGTTGCTC |
| SEQ ID NO: 2: GAGCAACCGTT |
| SEQ ID NO: 3: ATGGGAGC |
| SEQ ID NO: 4: CCATAACG |
| SEQ ID NO: 5: ATGGGAGCAACCGTT |
| SEQ ID NO: 6: CCATAACGGTTGCTCCCAT |
| SEQ ID NO: 7: ATGGGAGCAACCGTTATGG |
| SEQ ID NO: 8: CCATAACGGTTGCTCCCATAACGGITGCTCCCAT |
| SEQ ID NO: 9: ATGGGAGCAACCGTTATGGGAGCAACCGTTATGG |
| SEQ ID NO: 10: CGCCGGATGGCTCTTGGGAAACCAAACCGTACCAACC |
| SEQ ID NO: 11: CCGGATGGCTCTTGGGAAACCAAACCGTACCAACC |
| SEQ ID NO: 12: GGATGGCTCTTGGGAAACCAAACCGTACCAACC |
| SEQ ID NO: 13: ATGGCTCTTGGGAAACCAAACCGTACCAACC |
| SEQ ID NO: 14: TGGCTCTTGGGAAACCAAACCGTACCAACC |
| SEQ ID NO: 15: GGCTCTTGGGAAACCAAACCGTACCAACC |
| SEQ ID NO: 16: GCTCTTGGGAAACCAAACCGTACCAACC |
| SEQ ID NO: 17: CTCTTGGGAAACCAAACCGTACCAACC |
| SEQ ID NO: 18: TCTTGGGAAACCAAACCGTACCAACC |
| SEQ ID NO: 19: CTTGGGAAACCAAACCGTACCAACC |
| SEQ ID NO: 20: TTGGGAAACCAAACCGTACCAACC |
| SEQ ID NO: 21: TGGGAAACCAAACCGTACCAACC |
| SEQ ID NO: 22: GTTTCCCAAGAGCCATCCGGCGATGCGGAATGTACC |
| SEQ ID NO: 23: GTTTVCCAAGAGCCATCCGGATGCGGAATGTACC |
| SEQ ID NO: 24: GTTTCCCAAGAGCCATCCATGCGGAATGTACC |
| SEQ ID NO: 25: GTTTCCCAAGAGCCATATGCGGAATGTACC |
| SEQ ID NO: 26: GTTTCCCAAGAGCCAATGCGGAATGTACC |
| SEQ ID NO: 27: GTTTCCCAAGAGCCATGCGGAATGTACC |
| SEQ ID NO: 28: GTTTCCCAAGAGCATGCGGAATGTACC |
| SEQ ID NO: 29: GTTTCCCAAGAGATGCGGAATGTACC |
| SEQ ID NO: 30: GTTTCCCAAGAATGCGGAATGTACC |
| SEQ ID NO: 31: GTTTCCCAAGATGCGGAATGTACC |
| SEQ ID NO: 32: GTTTCCCAAATGCGGAATGTACC |
| SEQ ID NO: 33: GTTTCCCAATGCGGAATGTACC |
| SEQ ID NO: 34: ATGGCTCTTGGGAAACTGAAACCGTACCAACC |
| SEQ ID NO: 35: GTTTCCCAAGAGCCATGGATGCGGAATGTACC |
| SEQ ID NO: 36: GGCTCTTGGGAAACTGAAACCGTACCAACC |
| SEQ ID NO: 37: GTTTCCCAAGAGCCGGATGCGGAATGTACC |

SEQUENCE LISTING

SEQ ID NO: 38: CTCTTGGGAAACTGAAACCGTACCAACC

SEQ ID NO: 39: GTTTCCCAAGAGGGATGCGGAATGTACC

SEQ ID NO: 40: TCTTGGGAAACTGAAACCGTACCAACC

SEQ ID NO: 41: GTTTCCCAAGAGGATGCGGAATGTACC

SEQ ID NO: 42: CTTGGGAAACTGAAACCGTACCAACC

SEQ ID NO: 43: GTTTCCCAAGGGATGCGGAATGTACC

SEQ ID NO: 44: TTGGGAAACTGAAACCGTACCAACC

SEQ ID NO: 45: GTTTCCCAAGGATGCGGAATGTACC

SEQ ID NO: 46: TGGGAAACTGAAACCGTACCAACC

SEQ ID NO: 47: GTTTCCCAGGATGCGGAATGTACC

SEQ ID NO: 48: GGGAAACTGAAACCGTACCAACC

SEQ ID NO: 49: GTTTCCCGGATGCGGAATGTACC

SEQ ID NO: 50: ATGGCTCTTGGGAAACTGCCTGAAACCGTACCAACC

SEQ ID NO: 51: GTTTCCCAAGAGCCATACAGGGATGCGGAATGTACC

SEQ ID NO: 52: GGCTCTTGGGAAACTGCCTGAAACCGTACCAACC

SEQ ID NO: 53: GTTTCCCAAGAGCCACAGGGATGCGGAATGTACC

SEQ ID NO: 54: CTCTTGGGAAACTGCCTGAAACCGTACCAACC

SEQ ID NO: 55: GTTTCCCAAGAGACAGGGATGCGGAATGTACC

SEQ ID NO: 56: TCYTGGGAAACTGCCTGAAACCGTACCAACC

SEQ ID NO: 57: GTTTCCCAAGAACAGGGATGCGGAATGTACC

SEQ ID NO: 58: CTTGGGAAACTGCCTGAAACCGTACCAACC

SEQ ID NO: 59: GTTTCCCAAGACAGGGATGCGGAATGTACC

SEQ ID NO: 60: TTGGGAAACTGCCTGAAACCGTACCAACC

SEQ ID NO: 61: GTTTCCCAAACAGGGATGCGGAATGTACC

SEQ ID NO: 62: TGGGAAACTGCCTGAAACCGTACCAACC

SEQ ID NO: 63: GTTTCCCAACAGGGATGCGGAATGTACC

SEQ ID NO: 64: GGGAAACTGCCTGAAACCGTACCAACC

SEQ ID NO: 65: GTTTCCCACAGGGATGCGGAATGTACC

SEQ ID NO: 66:
TCTTGAGAGAACCCACTAACAGTAGAAGTACCATACATTTGTACAGAAGGGGAAGA
CCAAATTCTTGAGA

SEQ ID NO: 67:
TCTTGAGAGAACCCACTAACAGTAGAAGTACCATACATTTGTACAGAAGGGGAAGA
CCAAATTCTTGAGAGAACCCACTAACAGTAGAAGTACCATACATTT

SEQ ID NO: 68:
TCTTGAGAGAACCCACTAACAGTAGAAGTACCATACATTTGTACAGAAGGGGAAGA
CCAAATTCTTGAGAGAACCCACTAACAGTAGAAGTACCATACATTT

SEQ ID NO: 69:
TCTTGAGAGAACCCACTAACAGTAGAAGTACCATACATTTGTACAGAAGGGGAAGA
CCAAATTCTTGAGAGAACCCACTAACAGTAGAAGTACCATACATTT

SEQ ID NO: 70:
TCTTGAGAGAACCCACTAACAGTAGAAGTACCATACATTTGTACTGAAGGGGAAGA
CCAAATTCTTGAGAGAACCCACTAACAGTAGAAGTACCATACATTT

SEQUENCE LISTING

SEQ ID NO: 71:
TCTTGAGAGAACCCACTAACAGTAGAAGTACCATACATTTGTACAGAAGGGGAAGA
CCAAATTCTTGAGAGAACCCACTAACAGTAGAAGTACCATACATTT

SEQ ID NO: 72:
TCTTGAGAGAACCCACTAACAGTAGAAGTACCATACATTTGTACAGAAGGGGAAGA
CCAAATTCTTGAGAGAACCCACTAACAGTAGAAGTACCATACATTT

SEQ ID NO: 73:
TCTTGAGAGAACCCACTAACAGTAGAAGTACCATACATTTGTACAGAAGGGGAAGA
CCAAATTCTTGAGAGAACCCACTAACAGTAGAAGTACCATACATTT

SEQ ID NO: 74:
TCTTGAGAGAACCCACTAACAGTAGAAGTACCATACATTTGTACAGAAGGGGAAGA
CCAAATTCTTGAGAGAACCCACTAACAGTAGAAGTACCATACATTT

SEQ ID NO: 75:
TCTTGAGAGAACCCACTAACAGTAGAAGTACCATACATTTGTACAGAAGGGGAAGA
CCAATTCTTGAGAGAACCCACTAACAGTAGAAGTACCATACATTT

SEQ ID NO: 76:
GAACCCACTAACAGTAGAAGTACCATACATTTGTACAGAAGGGGAAGACCAAATGA
ACCCACTAACAGTAGAAGTACCATACATTT

SEQ ID NO: 77: TCTTGAGAGAACCCACTAACTCTTGAGAGAACCCACTAAC

SEQ ID NO: 78: GGAAGACCAAATTCTTGAGA

SEQ ID NO: 79:
MGHHHHHHHHHHSSGHIEGRASADGPYLQILEQPKQRGFRFRYVCEGPSHGGLPGASSE
KNKKSYPQVKICNYVGPAKVIVQLVTNGKNIHLHAHSLVGKHCEDGICTVTAGPKDMV
VGFANLGILHVTKKKVFETLEARMTEACIRGYNPGLLVHPDLAYLQAEGGGDRQLGDR
EKELIRQAALQQTKEMDLSVVRLMFTAFLPDSTGSFTRRLEPVVSDAIYDSKAPNASNL
KIVRMDRTAGCVTGGEEIYLLCDKVQKDDIQIRFYEEEENGGVWEGFGDFSPTDVHRQF
AIVFKTPKYKDINITKPASVFVQLRRKSDLETSEPKPFLYYPEIKDKEEVQRKRQKGSSGT
SGGGSGGGMTLEEARKRVNELRDLIRYHNYRYYVLADPEISDAEYDRLLRELKELEERF
PELKSPDSPTLQVGARPLEATFRPVRHPTRMYSLDNAFNLDELKAFEERIERALGRKGPF
AYTVEHKVDGLSVNLYYEEGVLVYGATRGDGEVGEEVTQNLLTIPTIPRRLKGVPERLE
VRGEVYMPIEAFLRLNEELEERGERIFKNPRNAAAGSLRQKDPRITAKRGLRATFYALGL
GLEEVEREGVATQFALLHWLKEKGFPVEHGYARAVGAEGVEAVYQDWLKKRRALPFE
ADGVVVKLDELALWRELGYTARAPRFAIAYKFPAEEKETRLLDVVFQVGRTGRVTPVG
ILEPVFLEGSEVSRVTLHNESYIEELDIRIGDWVLVHKAGGVIPEVLRVLKERRTGEERPIR
WPETCPECGHRLLKEGKVHRCPNPLCPAKRFEAIRHFASRKAMDIQGLGEKLIERLLEK
GLVKDVADLYRLRKEDLVGLERMGEKSAQNLLRQIEESKKRGLERLLYALGLPGVGEV
LARNLAARFGNMDRLLEASLEELLVEEVGELTARAILETLKDPAFRDLVRRLKEAGVE
MEAKEKGGEALKGLTFVITGELSRPREEVKALLRRLGAKVTDSVSRKTSYLVVGENPGS
KLEKARALGVPTLTEEELYRLLEARTGKKAEELV

SEQ ID NO: 80: CAAACCGTACCAACC

SEQ ID NO: 81: ATGCGGAATGTACC

SEQ ID NO: 82: CGCCGGATGGCTCTTGGGAAAC

SEQ ID NO: 83: GTTTCCCAAGAGCCATCCGGCG

SEQ ID NO: 84: TTGGGAAAC

SEQ ID NO: 85: GTTTCCCAA

SEQ ID NO: 86: TCTTGAGAGAACCCACTAAC

SEQ ID NO: 87: TCTCAAGAATTTGGTCTTCC

SEQ ID NO: 88: TCTTGAGA

SEQ ID NO: 89:
UCAGCAUUUCCCUCAGUUGCCUCCUUGUUUUUUCAAACAGUUUGUUCAUUCCG
AGUCAGUCAGAUCAAUUGUAUGUUGGUUCUCCAGAGCGACAAGAAGCUCCGCAU
UGUAAGACCAGAGAUCUAUUUUAGUGUCUUCAACGUAUUUCUCGAGGUCCUGAA
UUCUCCCUUCUACUUCUGAGAAUUCCUUUUCGAUUUGAUGGAAUUUCUCGUUCG
UCUUCUCGAUUACCCUAUUCAGUUUCCCAUUGAUUUGGUCGAUGGCUGCUUGAG
UGCUUUUAAGAUCUGCUGCUUGUCCUGUGCCCUCGGAAUUUUGAUGCCUGAAACC
GUACCAACCGUCUAUCAUUCCCUCCCAACCAUUUUCUAUGAAACCUGCUAUUGCG
CCGAAUAUGCCUCUAGUUUGUUUCUCUGGUACAUUCCGCAUCCCUGUUGCCAACU
UCAGAGUGUUUUGCUUAACAUACUUGGG

SEQUENCE LISTING

SEQ ID NO: 90:
GUCCUGGUGUUCACCAUAAGGUGUUACUGUGUCUUGGGAGCACCGCGACCUUUCG
CAACAAUGGCUUGGGCUGUCCCAAAGGACAACAACAAAAAUGCAACGAACCCACU
AACAGUAGAAGUACCAUACAUUUGUACAGAAGGGGAAGACCAAAUCACUGUUUG
GGGGUUCCAUUCAGAUGACAAAACCCAAAUGAAGAACCUCUAUGGAGACUCAAA
UCCUCAAAAGUUCACCUCAUCUGCUAAUGGUUUUGCCGACUGAAGGGACACCCCC
AGGGUCCUUGGGGGCAGUCAGGGAG

We claim:

1. A method of generating a concatemer comprising at least two copies of a double stranded nucleic acid template, the method comprising:

incubating in a reaction mixture at least a polymerase, a first template molecule, and a second template molecule, wherein:

the first template molecule comprises a first nucleic acid strand and a second nucleic acid strand, wherein:

the first nucleic acid strand of the first template molecule comprises a nucleotide sequence having the general structure in the 5' to 3' direction of: H'-S-$Y_1$-H', wherein: H' represents the nucleotide sequence of a first homology sequence, S represents the nucleotide sequence of a first strand of the double stranded nucleic acid template, and $Y_1$ represents any number and sequence of nucleotides; and the second nucleic acid strand of the first template molecule comprises a nucleotide sequence having the general structure in the 5' to 3' direction of: H-$Y_1$'-S'-H, wherein: H represents the nucleotide sequence of a second homology sequence, wherein the first homology sequence and second homology sequence are complementary to each other, $Y_1$' represents a nucleotide sequence which is complementary to the nucleotide sequence of $Y_1$, and S' represents the nucleotide sequence of a second strand of the double stranded nucleic acid template, wherein the first strand and second strand of the double stranded nucleic acid template are complementary to each other; and the second template molecule comprises a first nucleic acid strand and a second nucleic acid strand, wherein:

the first nucleic acid strand of the second template molecule comprises a nucleotide sequence having the general structure in the 5' to 3' direction of: H'-S-$Y_2$-H', wherein: H' represents the nucleotide sequence of the first homology sequence, S represents the nucleotide sequence of the first strand of the double stranded nucleic acid template, and $Y_2$ represents any number and sequence of nucleotides; and the second nucleic acid strand of the first template molecule comprises a nucleotide sequence having the general structure in the 5' to 3' direction of: H-$Y_2$'-S'-H, wherein: H represents the nucleotide sequence of the second homology sequence, $Y_2$' represents a nucleotide sequence which is complementary to the nucleotide sequence of $Y_2$, and S' represents the nucleotide sequence of the second strand of the double stranded nucleic acid template; and upon incubation of the first template molecule with the second template molecule in the reaction mixture, at least one concatemer comprising at least two copies of the double stranded nucleic acid template is formed, wherein the concatemer comprises a first concatemer strand and a second concatemer strand, wherein the first concatemer strand comprises a 5' end and a 3' end, and comprises a nucleotide sequence having the general structure in the 5' to 3' direction of: H'-S-$Y_2$-H'-S-$Y_1$-H', wherein each of H', $Y_1$, S, and $Y_2$ represent nucleotide sequences as described above; and wherein the second concatemer strand comprises a 5' end and a 3' end, and comprises a sequence having the general structure in the 5' to 3' direction of: H-$Y_1$'-S'-H-$Y_2$'-S'-H, wherein each of H', $Y_1$, S, and $Y_2$ represent nucleotide sequences as described above.

2. The method of claim 1, wherein at least one of $Y_1$ and $Y_2$ represents 0 nucleotides.

3. The method of claim 2, wherein both of $Y_1$ and $Y_2$ represent 0 nucleotides.

4. The method of claim 1, wherein $Y_1$ contains a sequence having the general structure in the 5' to 3' direction of $[(H'-S)_{N1}]$ wherein H' represents the nucleotide sequence of a first homology sequence, S represents the nucleotide sequence of a first strand of the double stranded nucleic acid template, and N1 is any integer between 0 and 2000.

5. The method of claim 1, wherein $Y_1$ contains a sequence having the general structure in the 5' to 3' direction of $[(H'-S)_{N1}]$ wherein H' represents the nucleotide sequence of a first homology sequence, S represents the nucleotide sequence of a first strand of the double stranded nucleic acid template, and N1 is any integer between 0 and 2000, and wherein $Y_2$ contains a sequence having the general structure in the 5' to 3' direction of $[(H'-S)_{N2}]$ wherein H' represents the nucleotide sequence of a first homology sequence, S represents the nucleotide sequence of a first strand of the double stranded nucleic acid template, and N2 is any integer between 0 and 2000.

6. The method of claim 5, wherein N1 and N2 are different integers.

7. The method of claim 6, wherein N1 is 0, and N2 is an integer between 1 and 2000.

8. The method of claim 1, wherein the first template molecule and second template molecule are both double-stranded DNA molecules.

9. The method of claim 1, wherein the first homology sequence contains between 4 and 25 nucleotides.

10. A method for generating a concatemer comprising two or more copies of a polynucleotide template or an analogous sequence thereof, the method comprising,
(A) treating a primary nucleic acid comprising the polynucleotide template with a first copy of a first primer and a polymerase under conditions such that an extension product of the first copy of the first primer is synthesized which is annealed to the polynucleotide template,
wherein
the first primer comprises a 5' terminal nucleotide, a 3' terminal nucleotide, and two regions:
(i) a tail region comprising
(a) the 5' terminal nucleotide of the primer
(b) an innermost nucleotide, wherein the innermost nucleotide is downstream from the 5' terminal nucleotide
(c) a middle section between the 5' terminal nucleotide and the innermost nucleotide, comprising one or more nucleotides, and
(ii) a template-binding region comprising
(a) the 3' terminal nucleotide of the primer
(b) an innermost nucleotide, wherein the innermost nucleotide is upstream from the 3' terminal nucleotide
(c) a middle section between the 3' terminal nucleotide and the innermost nucleotide, comprising one or more nucleotides, and the template-binding region of the first copy of the first primer anneals to the polynucleotide template,
(B) treating the extension product of the first copy of the first primer of step (A) with a second primer and a polymerase under conditions such that an extension product of the second primer is synthesized which is annealed to the extension product of the first copy of the first primer of step (A),
wherein
the second primer comprises a 5' terminal nucleotide, a 3' terminal nucleotide, and two regions:
(i) a tail region comprising
(a) the 5' terminal nucleotide of the primer
(b) an innermost nucleotide, wherein the innermost nucleotide is downstream from the 5' terminal nucleotide
(c) a middle section between the 5' terminal nucleotide and the innermost nucleotide, comprising one or more nucleotides
(ii) a template-binding region comprising
(a) the 3' terminal nucleotide of the primer
(b) an innermost nucleotide, wherein the innermost nucleotide is upstream from the 3' terminal nucleotide
(c) a middle section between the 3' terminal nucleotide and the innermost nucleotide, comprising one or more nucleotides,
the tail region of the second primer contains a nucleotide sequence which is complementary to the nucleotide sequence of the tail region of the first primer,
the template-binding region of the second primer anneals to the extension product of the first copy of the first primer of step (A), and
the extension product of the second primer contains a 5' terminal nucleotide, a 3' terminal nucleotide, and a 3' terminal region comprising the 3' terminal nucleotide, wherein the 3' terminal region contains the same nucleotide sequence as the nucleotide sequence of the tail region of the second primer read in the 5' to 3' direction, and the final nucleotide of the 3' terminal region is the 3' terminal nucleotide of the extension product of the second primer,
(C) treating the extension product of the second primer of step (B) with a second copy of the first primer and a polymerase under conditions such that an extension product of the second copy of the first primer is synthesized which is annealed to the extension product of the second primer of step (B), to produce a first copy of a secondary nucleic acid comprising the extension product of the second primer of step (B) and the extension product of the second copy of the first primer,
wherein
the extension product of the second copy of the first primer contains a 5' terminal nucleotide, a 3' terminal nucleotide, and a 3' terminal region comprising the 3' terminal nucleotide, wherein the 3' terminal region contains the same nucleotide sequence as the nucleotide sequence of the tail region of the first primer read in the 5' to 3' direction, and the final nucleotide of the 3' terminal region is the 3' terminal nucleotide of the extension product of the second primer
(D) repeating at least step (C) one or more addition times to generate at least a second copy of the secondary nucleic acid comprising the extension product of the second primer of step (B) and the extension product of the second copy of the first primer of step (C),
(E) treating the first copy of the secondary nucleic acid of step (C) and the second copy of the secondary nucleic acid of step (D) under conditions such that the 3' terminal region of the extension product of the second copy of the first primer of the first copy of the secondary nucleic acid anneals to the 3' terminal region of the extension product of the second primer of the second copy of the secondary nucleic acid, to produce a cross-over structure comprising the extension product of the second copy of the first primer of the first copy of the secondary nucleic acid and the extension product of the second primer of the second copy of the secondary nucleic acid,
(F) treating the cross-over structure of step (E) with a polymerase under conditions such that an extension product of the extension product of the second copy of the first primer of the first copy of the secondary nucleic acid is synthesized and an extension product of the extension product of the second primer of the second copy of the secondary nucleic acid is synthesized, to produce a concatemer comprising two copies of the polynucleotide template of step (A), wherein the concatemer comprises the extension product of the extension product of the second copy of the first primer of the first copy of the secondary nucleic acid and the extension product of the extension product of the second primer of the second copy of the secondary nucleic acid.

11. The method claim 10, wherein the nucleic acid polymerase of step (A) is a DNA polymerase.

12. The method of claim 10, wherein the nucleic acid polymerase of step (A) is a reverse transcriptase.

13. The method of claim 10, wherein all steps of the method are performed at a temperature of no greater than 80 C.

14. The method of claim 10, wherein two or more of the steps occur simultaneously.

15. A method for generating a concatemer comprising two or more copies of a polynucleotide template, the method comprising,
   (A) preparing a reaction mixture comprising:
      (i) a nucleic acid comprising the polynucleotide template
      (ii) an isolated nucleic acid polymerase,
      (iii) a first primer comprising a 5' terminal nucleotide, a 3' terminal nucleotide, and two regions:
         (a) a tail region comprising
            (1) the 5' terminal nucleotide of the primer
            (2) an innermost nucleotide, wherein the innermost nucleotide is downstream from the 5' terminal nucleotide
            (3) a middle section between the 5' terminal nucleotide and the innermost nucleotide, comprising one or more nucleotides, and
         (b) a template-binding region comprising
            (1) the 3' terminal nucleotide of the primer
            (2) an innermost nucleotide, wherein the innermost nucleotide is upstream from the 3' terminal nucleotide
            (3) a middle section between the 3' terminal nucleotide and the innermost nucleotide, comprising one or more nucleotides, and
         wherein the template-binding region is complementary to the polynucleotide template,
      (iv) a second primer comprising a 5' terminal nucleotide, a 3' terminal nucleotide, and two regions:
         (a) a tail region comprising
            (1) the 5' terminal nucleotide of the primer
            (2) an innermost nucleotide, wherein the innermost nucleotide is downstream from the 5' terminal nucleotide
            (3) a middle section between the 5' terminal nucleotide and the innermost nucleotide, comprising one or more nucleotides, and
         (b) a template-binding region comprising
            (1) the 3' terminal nucleotide of the primer
            (2) an innermost nucleotide, wherein the innermost nucleotide is upstream from the 3' terminal nucleotide
            (3) a middle section between the 3' terminal nucleotide and the innermost nucleotide, comprising one or more nucleotides, and
         wherein the template-binding region is complementary to a nucleotide sequence complementary to the polynucleotide template, and
         wherein the tail region of the second primer contains a nucleotide sequence which is complementary to the nucleotide sequence of the tail region of the first primer, and
   (B) incubating the reaction mixture at a temperature of no greater than 80 C for at least 3 minutes.

16. The method of claim 15, wherein the polynucleotide template is amplified at least 10-fold within 60 minutes of initiation of the method.

17. The method of claim 15, wherein the tail region of the first primer contains between 4 and 25 nucleotides.

18. The method of claim 15, wherein the polynucleotide template is a double-stranded nucleic acid template.

* * * * *

SEQUENCE LISTING

<160> NUMBER OF SEQ ID NOS: 91

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aacggttgct c                                                           11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gagcaaccgt t                                                           11

<210> SEQ ID NO 3
<211> LENGTH: 8
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3 atgggagc                                                                8

<210> SEQ ID NO 4
<211> LENGTH: 8
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4 ccataacg                                                                8

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgggagcaa ccgtt                                                    15

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccataacggt tgctcccat                                                19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgggagcaa ccgttatgg                                                19

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccataacggt tgctcccata acggttgctc ccat                               34

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgggagcaa ccgttatggg agcaaccgtt atgg                               34

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgccggatgg ctcttgggaa accaaaccgt accaacc                            37

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccggatggct cttgggaaac caaaccgtac caacc    35

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggatggctct tgggaaacca aaccgtacca acc    33

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggctcttg ggaaaccaaa ccgtaccaac c    31

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggctcttgg gaaaccaaac cgtaccaacc    30

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggctcttggg aaaccaaacc gtaccaacc    29

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gctcttggga aaccaaaccg taccaacc    28

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 17
ctcttgggaa accaaaccgt accaacc                                          27

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcttgggaaa ccaaaccgta ccaacc                                           26

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cttgggaaac caaaccgtac caacc                                            25

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttgggaaacc aaaccgtacc aacc                                             24

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgggaaacca aaccgtacca acc                                              23

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtttcccaag agccatccgg cgatgcggaa tgtacc                                36

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 23
gtttcccaag agccatccgg atgcggaatg tacc                                34

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtttcccaag agccatccat gcggaatgta cc                                  32

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtttcccaag agccatatgc ggaatgtacc                                     30

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtttcccaag agccaatgcg gaatgtacc                                      29

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtttcccaag agccatgcgg aatgtacc                                       28

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gtttcccaag agcatgcgga atgtacc                                        27

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 29
gtttcccaag agatgcggaa tgtacc          26

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtttcccaag aatgcggaat gtacc           25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtttcccaag atgcggaatg tacc            24

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtttcccaaa tgcggaatgt acc             23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtttcccaat gcggaatgta cc              22

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atggctcttg ggaaactgaa accgtaccaa cc   32

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtttcccaag agccatggat gcggaatgta cc                                     32

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggctcttggg aaactgaaac cgtaccaacc                                        30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtttcccaag agccggatgc ggaatgtacc                                        30

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctcttgggaa actgaaaccg taccaacc                                          28

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtttcccaag agggatgcgg aatgtacc                                          28

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcttgggaaa ctgaaaccgt accaacc                                           27

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gtttcccaag aggatgcgga atgtacc                                           27

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cttgggaaac tgaaaccgta ccaacc                                            26

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtttcccaag ggatgcggaa tgtacc                                            26

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ttgggaaact gaaaccgtac caacc                                             25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtttcccaag gatgcggaat gtacc                                             25

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgggaaactg aaaccgtacc aacc                                              24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gtttcccagg atgcggaatg tacc                                              24

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gggaaactga aaccgtacca acc                                               23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtttcccgga tgcggaatgt acc                                               23

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
atggctcttg ggaaactgcc tgaaaccgta ccaacc                                 36

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtttcccaag agccatacag ggatgcggaa tgtacc                                 36

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggctcttggg aaactgcctg aaaccgtacc aacc                                   34

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtttcccaag agccacaggg atgcggaatg tacc                                        34

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctcttgggaa actgcctgaa accgtaccaa cc                                          32

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gtttcccaag agacagggat gcggaatgta cc                                          32

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tcttgggaaa ctgcctgaaa ccgtaccaac c                                           31

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtttcccaag aacagggatg cggaatgtac c                                           31

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cttgggaaac tgcctgaaac cgtaccaacc                                             30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 59
gtttcccaag acagggatgc ggaatgtacc                                    30

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttgggaaact gcctgaaacc gtaccaacc                                     29

<210> SEQ ID NO 61
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtttcccaaa cagggatgcg gaatgtacc                                     29

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tgggaaactg cctgaaaccg taccaacc                                      28

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gtttcccaac agggatgcgg aatgtacc                                      28

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gggaaactgc ctgaaaccgt accaacc                                       27

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 65
gtttcccaca gggatgcgga atgtacc                                         27

<210> SEQ ID NO 66
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tcttgagaga acccactaac agtagaagta ccatacattt gtacagaagg ggaagaccaa     60
attcttgaga                                                            70

<210> SEQ ID NO 67
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
tcttgagaga acccactaac agtagaagta ccatacattt gtacagaagg ggaagaccaa     60
attcttgaga gaacccacta acagtagaag taccatacat tt                       102

<210> SEQ ID NO 68
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
tcttgagaga acccactaac agtagaagta ccatacattt gtacagaagg ggaagaccaa     60
attcttgaga gaacccacta acagtagaag taccatacat tt                       102

<210> SEQ ID NO 69
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
tcttgagaga acccactaac agtagaagta ccatacattt gtacagaagg ggaagaccaa     60
attcttgaga gaacccacta acagtagaag taccatacat tt                       102

<210> SEQ ID NO 70
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
tcttgagaga acccactaac agtagaagta ccatacattt gtactgaagg ggaagaccaa     60
attcttgaga gaacccacta acagtagaag taccatacat tt                       102
```

```
<210> SEQ ID NO 71
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
tcttgagaga acccactaac agtagaagta ccatacattt gtacagaagg ggaagaccaa      60
attcttgaga gaacccacta acagtagaag taccatacat tt                       102

<210> SEQ ID NO 72
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
tcttgagaga acccactaac agtagaagta ccatacattt gtacagaagg ggaagaccaa      60
attcttgaga gaacccacta acagtagaag taccatacat tt                       102

<210> SEQ ID NO 73
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
tcttgagaga acccactaac agtagaagta ccatacattt gtacagaagg ggaagaccaa      60
attcttgaga gaacccacta acagtagaag taccatacat tt                       102

<210> SEQ ID NO 74
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
tcttgagaga acccactaac agtagaagta ccatacattt gtacagaagg ggaagaccaa      60
attcttgaga gaacccacta acagtagaag taccatacat tt                       102

<210> SEQ ID NO 75
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
tcttgagaga acccactaac agtagaagta ccatacattt gtacagaagg ggaagaccaa      60
ttcttgagag aacccactaa cagtagaagt accatacatt t                        101

<210> SEQ ID NO 76
<211> LENGTH: 86
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 76
gaacccacta acagtagaag taccatacat ttgtacagaa ggggaagacc aaatgaaccc    60
actaacagta gaagtaccat acattt                                        86

<210> SEQ ID NO 77
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tcttgagaga acccactaac tcttgagaga acccactaac                         40

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ggaagaccaa attcttgaga                                               20

<210> SEQ ID NO 79
<211> LENGTH: 1038
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79
```

Met Gly His His His His His His His His His Ser Ser Gly His
 1               5                  10                  15

Ile Glu Gly Arg Ala Ser Ala Asp Gly Pro Tyr Leu Gln Ile Leu Glu
            20                  25                  30

Gln Pro Lys Gln Arg Gly Phe Arg Phe Arg Tyr Val Cys Glu Gly Pro
        35                  40                  45

Ser His Gly Gly Leu Pro Gly Ala Ser Ser Glu Lys Asn Lys Lys Ser
    50                  55                  60

Tyr Pro Gln Val Lys Ile Cys Asn Tyr Val Gly Pro Ala Lys Val Ile
65                  70                  75                  80

Val Gln Leu Val Thr Asn Gly Lys Asn Ile His Leu His Ala His Ser
                85                  90                  95

Leu Val Gly Lys His Cys Glu Asp Gly Ile Cys Thr Val Thr Ala Gly
            100                 105                 110

Pro Lys Asp Met Val Val Gly Phe Ala Asn Leu Gly Ile Leu His Val
        115                 120                 125

Thr Lys Lys Lys Val Phe Glu Thr Leu Glu Ala Arg Met Thr Glu Ala
    130                 135                 140

Cys Ile Arg Gly Tyr Asn Pro Gly Leu Leu Val His Pro Asp Leu Ala
145                 150                 155                 160

Tyr Leu Gln Ala Glu Gly Gly Gly Asp Arg Gln Leu Gly Asp Arg Glu
                165                 170                 175

```
Lys Glu Leu Ile Arg Gln Ala Ala Leu Gln Gln Thr Lys Glu Met Asp
                180                 185                 190
Leu Ser Val Val Arg Leu Met Phe Thr Ala Phe Leu Pro Asp Ser Thr
            195                 200                 205
Gly Ser Phe Thr Arg Arg Leu Glu Pro Val Val Ser Asp Ala Ile Tyr
        210                 215                 220
Asp Ser Lys Ala Pro Asn Ala Ser Asn Leu Lys Ile Val Arg Met Asp
225                 230                 235                 240
Arg Thr Ala Gly Cys Val Thr Gly Gly Glu Ile Tyr Leu Leu Cys
                245                 250                 255
Asp Lys Val Gln Lys Asp Asp Ile Gln Ile Arg Phe Tyr Glu Glu Glu
                260                 265                 270
Glu Asn Gly Gly Val Trp Glu Gly Phe Gly Asp Phe Ser Pro Thr Asp
                275                 280                 285
Val His Arg Gln Phe Ala Ile Val Phe Lys Thr Pro Lys Tyr Lys Asp
            290                 295                 300
Ile Asn Ile Thr Lys Pro Ala Ser Val Phe Val Gln Leu Arg Arg Lys
305                 310                 315                 320
Ser Asp Leu Glu Thr Ser Glu Pro Lys Pro Phe Leu Tyr Tyr Pro Glu
                325                 330                 335
Ile Lys Asp Lys Glu Glu Val Gln Arg Lys Arg Gln Lys Gly Ser Ser
                340                 345                 350
Gly Thr Ser Gly Gly Gly Ser Gly Gly Met Thr Leu Glu Glu Ala
                355                 360                 365
Arg Lys Arg Val Asn Glu Leu Arg Asp Leu Ile Arg Tyr His Asn Tyr
            370                 375                 380
Arg Tyr Tyr Val Leu Ala Asp Pro Glu Ile Ser Asp Ala Glu Tyr Asp
385                 390                 395                 400
Arg Leu Leu Arg Glu Leu Lys Glu Leu Glu Glu Arg Phe Pro Glu Leu
                405                 410                 415
Lys Ser Pro Asp Ser Pro Thr Leu Gln Val Gly Ala Arg Pro Leu Glu
                420                 425                 430
Ala Thr Phe Arg Pro Val Arg His Pro Thr Arg Met Tyr Ser Leu Asp
            435                 440                 445
Asn Ala Phe Asn Leu Asp Glu Leu Lys Ala Phe Glu Glu Arg Ile Glu
        450                 455                 460
Arg Ala Leu Gly Arg Lys Gly Pro Phe Ala Tyr Thr Val Glu His Lys
465                 470                 475                 480
Val Asp Gly Leu Ser Val Asn Leu Tyr Tyr Glu Glu Gly Val Leu Val
                485                 490                 495
Tyr Gly Ala Thr Arg Gly Asp Gly Glu Val Gly Glu Val Thr Gln
                500                 505                 510
Asn Leu Leu Thr Ile Pro Thr Ile Pro Arg Arg Leu Lys Gly Val Pro
            515                 520                 525
Glu Arg Leu Glu Val Arg Gly Glu Val Tyr Met Pro Ile Glu Ala Phe
                530                 535                 540
Leu Arg Leu Asn Glu Glu Leu Glu Glu Arg Gly Glu Arg Ile Phe Lys
545                 550                 555                 560
Asn Pro Arg Asn Ala Ala Ala Gly Ser Leu Arg Gln Lys Asp Pro Arg
                565                 570                 575
Ile Thr Ala Lys Arg Gly Leu Arg Ala Thr Phe Tyr Ala Leu Gly Leu
                580                 585                 590
```

```
Gly Leu Glu Glu Val Glu Arg Glu Gly Val Ala Thr Gln Phe Ala Leu
            595                 600                 605

Leu His Trp Leu Lys Glu Lys Gly Phe Pro Val Glu His Gly Tyr Ala
        610                 615                 620

Arg Ala Val Gly Ala Glu Gly Val Glu Ala Val Tyr Gln Asp Trp Leu
625                 630                 635                 640

Lys Lys Arg Arg Ala Leu Pro Phe Glu Ala Asp Gly Val Val Val Lys
                645                 650                 655

Leu Asp Glu Leu Ala Leu Trp Arg Glu Leu Gly Tyr Thr Ala Arg Ala
            660                 665                 670

Pro Arg Phe Ala Ile Ala Tyr Lys Phe Pro Ala Glu Glu Lys Glu Thr
        675                 680                 685

Arg Leu Leu Asp Val Val Phe Gln Val Gly Arg Thr Gly Arg Val Thr
690                 695                 700

Pro Val Gly Ile Leu Glu Pro Val Phe Leu Glu Gly Ser Glu Val Ser
705                 710                 715                 720

Arg Val Thr Leu His Asn Glu Ser Tyr Ile Glu Glu Leu Asp Ile Arg
                725                 730                 735

Ile Gly Asp Trp Val Leu Val His Lys Ala Gly Gly Val Ile Pro Glu
            740                 745                 750

Val Leu Arg Val Leu Lys Glu Arg Arg Thr Gly Glu Glu Arg Pro Ile
        755                 760                 765

Arg Trp Pro Glu Thr Cys Pro Glu Cys Gly His Arg Leu Leu Lys Glu
770                 775                 780

Gly Lys Val His Arg Cys Pro Asn Pro Leu Cys Pro Ala Lys Arg Phe
785                 790                 795                 800

Glu Ala Ile Arg His Phe Ala Ser Arg Lys Ala Met Asp Ile Gln Gly
                805                 810                 815

Leu Gly Glu Lys Leu Ile Glu Arg Leu Leu Glu Lys Gly Leu Val Lys
            820                 825                 830

Asp Val Ala Asp Leu Tyr Arg Leu Arg Lys Glu Asp Leu Val Gly Leu
        835                 840                 845

Glu Arg Met Gly Glu Lys Ser Ala Gln Asn Leu Leu Arg Gln Ile Glu
850                 855                 860

Glu Ser Lys Lys Arg Gly Leu Glu Arg Leu Leu Tyr Ala Leu Gly Leu
865                 870                 875                 880

Pro Gly Val Gly Glu Val Leu Ala Arg Asn Leu Ala Ala Arg Phe Gly
                885                 890                 895

Asn Met Asp Arg Leu Leu Glu Ala Ser Leu Glu Glu Leu Leu Glu Val
            900                 905                 910

Glu Glu Val Gly Glu Leu Thr Ala Arg Ala Ile Leu Glu Thr Leu Lys
        915                 920                 925

Asp Pro Ala Phe Arg Asp Leu Val Arg Arg Leu Lys Glu Ala Gly Val
930                 935                 940

Glu Met Glu Ala Lys Glu Lys Gly Gly Glu Ala Leu Lys Gly Leu Thr
945                 950                 955                 960

Phe Val Ile Thr Gly Glu Leu Ser Arg Pro Arg Glu Glu Val Lys Ala
                965                 970                 975

Leu Leu Arg Arg Leu Gly Ala Lys Val Thr Asp Ser Val Ser Arg Lys
            980                 985                 990

Thr Ser Tyr Leu Val Val Gly Glu Asn Pro Gly Ser Lys Leu Glu Lys
        995                 1000                1005
```

-continued

```
Ala Arg Ala Leu Gly Val Pro Thr Leu Thr Glu Glu Glu Leu Tyr
1010                1015                1020

Arg Leu Leu Glu Ala Arg Thr Gly Lys Lys Ala Glu Glu Leu Val
    1025                1030                1035
```

<210> SEQ ID NO 80
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
caaaccgtac caacc                                                          15

<210> SEQ ID NO 81
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
atgcggaatg tacc                                                           14

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cgccggatgg ctcttgggaa ac                                                  22

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gtttcccaag agccatccgg cg                                                  22

<210> SEQ ID NO 84
<211> LENGTH: 9
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84 ttgggaaac                                                                  9

<210> SEQ ID NO 85
<211> LENGTH: 9
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85 gtttcccaa                                                                    9

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tcttgagaga acccactaac                                                       20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tctcaagaat ttggtcttcc                                                       20

<210> SEQ ID NO 88
<211> LENGTH: 8
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88 tcttgaga                                                                     8

<210> SEQ ID NO 89
<211> LENGTH: 464
<212> TYPE: RNA
<213> ORGANISM: Influenza A virus

<400> SEQUENCE: 89
ucagcauuuu cccucaguug ccuccuuguu uuucaaaca guuuguucau uuccgaguca            60
gucagaucaa uuguauguug guucuccaga gcgacaagaa gcuccgcauu guaagaccag          120
agaucuauuu uagugucuuc aacguauuuc ucgagguccu gaauucuccc uucuacuucu          180
gagaauuccu uuucgauuug auggaauuuc ucguucgucu ucucgauuac ccuauucagu          240
uucccauuga uuuggucgau ggcugcuuga gugcuuuuaa gaucgcugc uuguccugu            300 cccucggaau uuugaugccu gaaaccguac caaccgucua ucauucccuc ccaaccauuu          360
ucuaugaaac cugcuauugc gccgaauaug ccucuaguuu guuucucugg uacauuccgc          420
aucccuguug ccaacuucag aguguuugc uuaacauacu uggg                            464

<210> SEQ ID NO 90
<211> LENGTH: 298
<212> TYPE: RNA
<213> ORGANISM: Influenza B virus

<400> SEQUENCE: 90
guccuggugu ucaccauaag guguuacugu gucuugggag caccgcgacc uuucgcaaca 60
auggcuuggg cugucccaaa ggacaacaac aaaaaugcaa cgaacccacu aacaguagaa 120

-continued

```
guaccauaca uuuguacaga aggggaagac caaaucacug uuuggggguu ccauucagau      180
gacaaaaccc aaaugaagaa ccucuaugga gacucaaauc cucaaaaguu caccucaucu      240
gcuaaugguu uugccgacug aagggacacc cccagggucc uugggggcag ucagggag        298

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 91

His His His His His His His His His His
1               5                   10
```